(12) United States Patent
Dai

(10) Patent No.: US 7,977,470 B2
(45) Date of Patent: Jul. 12, 2011

(54) HUMAN RON-RELATED GENE VARIANT ASSOCIATED WITH CANCERS

(75) Inventor: Ken-Shwo Dai, Hsinchu (TW)

(73) Assignee: Visgeneer, Inc., Hsuichu (TW)

( * ) Notice: Subject to any disclaimer, the term of this patent is extended or adjusted under 35 U.S.C. 154(b) by 180 days.

(21) Appl. No.: 12/209,154

(22) Filed: Sep. 11, 2008

(65) Prior Publication Data

US 2009/0148898 A1    Jun. 11, 2009

Related U.S. Application Data

(62) Division of application No. 11/465,308, filed on Aug. 17, 2006, now Pat. No. 7,452,985.

(51) Int. Cl.
| | |
|---|---|
| *C07H 21/04* | (2006.01) |
| *C07H 21/02* | (2006.01) |
| *C12N 15/00* | (2006.01) |
| *C12N 5/00* | (2006.01) |
| *C12N 5/02* | (2006.01) |
| *C12N 15/64* | (2006.01) |

(52) U.S. Cl. ............... 536/23.5; 435/320.1; 435/325; 435/91.4; 536/23.1; 536/24.33

(58) Field of Classification Search .................. None
See application file for complete search history.

(56) References Cited

U.S. PATENT DOCUMENTS

| 2007/0083334 A1* | 4/2007 | Mintz et al. .............. 702/19 |
| 2010/0081129 A1* | 4/2010 | Belouchi et al. .............. 435/6 |

FOREIGN PATENT DOCUMENTS

| EP | 06017649.2 | 1/2007 |
| WO | WO2004023973 | 3/2004 |

OTHER PUBLICATIONS

Angeloni, D., et al., The soluble sema domain of the Ron receptor inhibits macrophage-stimulating protein-induced receptor activation. J. Biol. Chem. 279:3726-32, (2004).

Camp, E.R., et al., Ron, a tyrosine kinase receptor involved in tumor progression and metastasis.Ann Surg Oncol. 12:273-81, (2005).

Collesi, C., et al., A splicing variant of the Ron transcript induces constitutive tyrosine kinase activity and an invasive phenotype. Molecular and Cellular Biology 16:5518-5526, (1996).

Maggiora, P., et al., Overexpression of the Ron gene in human breast carcinoma. Oncogene 16:2927-2933, (1998).

Peace, B.E., et al., Ron receptor signaling augments mammary tumor formation and metastasis in a murine model of breast cancer. Cancer Res. 65:1285-93, (2005).

Wang, M., et al., Identification of a novel splicing product of the Ron receptor tyrosine kinase in human colorectal carcinoma cells. Carcinogenesis 21: 1507-1512 (2000).

Wang, M., et al., Oncogenic and invasive potentials of human macrophage-stimulating protein receptor, the Ron receptor tyrosine kinase. Carcinogenesis 24:1291-300, (2003).

Willet, C., et al., Human Ron receptor protein. Database EMBL, Accession No. AAW82791, Apr. 12, 1999.

Willett, C.G., et al., Differential screening of a human chromosome 3 library identifies hepatocyte growth factor-like/macrophage-stimulating protein and its receptor in injured lung. Possible implications for neuroendocrine cell survival. J Clin Invest. 99:2979-91, (1997).

Xu, X., et al., RNA-mediated gene splicing of the Ronreceptor tyrosine kinase alters oncogenic phenotypes of human colorectal carcinoma cells. Oncogene 23:8464-8474, (2004).

Zhou, Y., et al., Altered expression of the Ron receptor tyrosine kinase in primary human colorectal adenocarcinomas: generation of different splicing Ron variants and their oncogenic potential. Oncogene 22:186-197, (2003).

* cited by examiner

*Primary Examiner* — Anne M. Gussow
(74) *Attorney, Agent, or Firm* — Baker & McKenzie LLP

(57) ABSTRACT

The invention relates to the nucleic acid and polypeptide sequences of three novel human Ron-related gene variants (Ron-V1, Ron-V2, and Ron-V3). The invention also provides a process for producing the polypeptides of the variants, as well as uses for the nucleic acid, polypeptide and antibodies to same in diagnosing human breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

3 Claims, 53 Drawing Sheets

FIG. 1A-1 SEQ ID NO: 1

| | | | | | | |
|---|---|---|---|---|---|---|
| ggatcctcta | gggtcccagc | tcgcctcgat | ggagctcctc | ccgccgctgc | ctcagtcctt | 60 |
| cctgttgctg | ctgctgttgc | ctgccaagcc | cgcggcgggc | gaggactggc | agtgcccgcg | 120 |
| cacccoctac | gcggcctctc | gcgactttga | cgtgaagtac | gtggtgccca | gcttctccgc | 180 |
| cggaggcctg | gtacaggcca | tggtgaccta | cgagggcgac | agaaatgaga | gtgctgtgtt | 240 |
| tgtagccata | cgcaatcgcc | tgcatgtgct | tgggcctgac | ctgaagtctg | tccagagcct | 300 |
| ggccacgggc | cctgctggag | accctggctg | ccagacgtgt | gcagcctgtg | gcccaggacc | 360 |
| ccacggccct | cccggtgaca | cagacacaaa | ggtgctggtg | ctggatcccg | cgctgcctgc | 420 |
| gctggtcagt | tgtggctcca | gcctgcaggg | ccgctgcttc | ctgcatgacc | tagagcccca | 480 |
| agggacagcc | gtgcatctgg | cagcgccagc | ctgcctcttc | tcagcccacc | ataaccggcc | 540 |
| cgatgactgc | cccgactgtg | tggccagccc | attgggcacc | cgtgtaactg | tggttgagca | 600 |
| aggccaggcc | tcctatttct | acgtggcatc | ctcactggac | gcagccgtgg | ctggcagctt | 660 |
| cagcccacgc | tcagtgtcta | tcaggcgtct | caaggctgac | gcctcgggat | tcgcaccggg | 720 |
| ctttgtggcg | ttgtcagtgc | tgcccaagca | tcttgtctcc | tacagtattg | aatacgtgca | 780 |
| cagcttccac | acgggagcct | tcgtatactt | cctgactgta | cagccggcca | gcgtgacaga | 840 |
| tgatcctagt | gccctgcaca | cacgcctggc | acggcttagc | gccactgagc | cagagttggg | 900 |
| tgactatcgg | gagctggtcc | tcgactgcag | atttgctcca | aaacgcaggc | gccgggggggc | 960 |
| cccagaaggc | ggacagccct | accctgtgct | gcaggtggcc | cactccgctc | cagtgggtgc | 1020 |
| ccaacttgcc | actgagctga | gcatcgccga | gggccaggaa | gtactatttg | gggtctttgt | 1080 |
| gactggcaag | gatggtggtc | ctggcgtggg | ccccaactct | gtcgtctgtg | ccttccccat | 1140 |
| tgacctgctg | gacacactaa | ttgatgaggg | tgtggagcgc | tgttgtgaat | ccccagtcca | 1200 |
| tccaggcctc | cggcgaggcc | tcgacttctt | ccagtcgccc | agttttttgcc | ccaacccgcc | 1260 |
| tggcctggaa | gccctcagcc | ccaacaccag | ctgccgccac | ttccctctgc | tggtcagtag | 1320 |
| cagcttctca | cgtgtggacc | tattcaatgg | gctgttggga | ccagtacagg | tcactgcatt | 1380 |
| gtatgtgaca | cgccttgaca | acgtcacagt | ggcacacatg | ggcacaatgg | atgggcgtat | 1440 |
| cctgcaggtg | gagctggtca | ggtcactaaa | ctacttgctg | tatgtgtcca | acttctcact | 1500 |
| gggtgacagt | gggcagcccg | tgcagcggga | tgtcagtcgt | cttggggacc | acctactctt | 1560 |
| tgcctctggg | gaccaggttt | tccaggtacc | tatccgaggc | cctggctgcc | gccacttcct | 1620 |
| gacctgtggg | cgttgcctaa | gggcatggca | tttcatgggc | tgtggctggt | gtgggaacat | 1680 |
| gtgcggccag | cagaaggagt | gtcctggctc | ctggcaacag | gaccactgcc | cacctaagct | 1740 |
| tactgagttc | cacccccaca | gtggacctct | aaggggcagt | acaaggctga | ccctgtgtgg | 1800 |
| ctccaacttc | taccttcacc | cttctggtct | ggtgcctgag | ggaacccatc | aggtcactgt | 1860 |
| gggccaaagt | ccctgccggc | cactgcccaa | ggacagctca | aaactcagac | cagtgccccg | 1920 |
| gaaagacttt | gtagaggagt | ttgagtgtga | actggagccc | ttgggcaccc | aggcagtggg | 1980 |
| gcctaccaac | gtcagcctca | ccgtgactaa | catgccaccg | ggcaagcact | tccgggtaga | 2040 |
| cggcacctcc | gtgctgagag | gcttctcttt | catggagcca | gtgctgatag | cagtgcaacc | 2100 |
| cctcttttggc | ccacgggcag | gaggcacctg | tctcactctt | gaaggccaga | gtctgtctgt | 2160 |
| aggcaccagc | cgggctgtgc | tggtcaatgg | gactgagtgt | ctgctagcac | gggtcagtga | 2220 |

FIG. 1A-2　　　　　　　SEQ ID NO: 1 cont.

```
ggggcagctt ttatgtgcca cacccctgg ggccacggtg gccagtgtcc cccttagcct   2280
gcaggtgggg ggtgcccagg tacctggttc ctggaccttc cagtacagag aagaccctgt   2340
cgtgctaagc atcagccca  actgtggcta catcaactcc cacatcacca tctgtggcca   2400
gcatctaact tcagcatggc acttagtgct gtcattccat gacgggctta gggcagtgga   2460
aagcaggtgt gagaggcagc ttccagagca gcagctgtgc cgccttcctg aatatgtggt   2520
ccgagacccc cagggatggg tggcagggaa tctgagtgcc cgaggggatg gagctgctgg   2580
ctttacactg cctggctttc gcttcctacc cccacccat ccacccagtg ccaacctagt   2640
tccactgaag cctgaggagc atgccattaa gtttgagtat attgggctgg gcgctgtggc   2700
tgactgtgtg ggtatcaacg tgaccgtggg tggtgagagc tgccagcacg agttccgggg   2760
ggacatggtt gtctgccccc tgcccccatc cctgcagctt ggccaggatg gtgcccatt    2820
gcaggtctgc gtagatggtg aatgtcatat cctgggtaga gtggtgcggc cagggccaga   2880
tggggtccca cagagcacgc tccttggtat cctgctgcct tgctgctgc ttgtggctgc    2940
actggcgact gcactggtct tcagctactg gtggcggagg aagcagctag ttcttcctcc   3000
caacctgaat gacctggcat ccctggacca gactgctgga gccacacccc tgcctattct   3060
gtactcgggc tctgactaca gaagtggcct tgcactccct gccattgatg gtctggattc   3120
caccacttgt gtccatggag catccttctc cgatagtgaa gatgaatcct gtgtgccact   3180
gctgcggaaa gagtccatcc agctaaggga cctggactct gcgctcttgg ctgaggtcaa   3240
ggatgtgctg attccccatg agcgggtggt cacccacagt gaccgagtca ttggcaaagg   3300
ccactttgga gttgtctacc acggagaata catagaccag gcccagaatc gaatccaatg   3360
tgccatcaag tcactaagtc gcatcacaga gatgcagcag gtggaggcct tcctgcgaga   3420
ggggctgctc atgcgtggcc tgaaccaccc gaatgtgctg gctctcattg gtatcatgtt   3480
gccacctgag ggcctgcccc atgtgctgct gccctatatg tgccacggtg acctgctcca   3540
gttcatccgc tcacctcagc ggaaccccac cgtgaaggac ctcatcagct ttggcctgca   3600
ggtagcccgc ggcatggagt acctggcaga gcagaagttt gtgcacaggg acctggctgc   3660
gcggaactgc atgctggacg agtcattcac agtcaaggtg gctgactttg gtttggcccg   3720
cgacatcctg gacagggagt actatagtgt tcaacagcat cgccacgctc gcctacctgt   3780
gaagtggatg gcgctggaga gcctgcagac ctatagattt accaccaagt ctgatgtgtg   3840
gtcatttggt gtgctgctgt gggaactgct gacacggggt gccccaccat accgccacat   3900
tgacccttt gaccttaccc acttcctggc ccagggtcgg cgcctgcccc agcctgagta    3960
ttgccctgat tctctgtacc aagtgatgca gcaatgctgg gaggcagacc cagcagtgcg   4020
acccacttc agagtactag tggggaggt ggagcagata gtgtctgcac tgcttgggga    4080
ccattatgtg cagctgccag caacctacat gaacttgggc cccagcacct cgcatgagat   4140
gaatgtgcgt ccagaacagc cgcagttctc acccatgcca gggaatgtac gccggccccg   4200
gccactctca gagcctcctc ggcccacttg acttagttct tgggctggac ctgcttagct   4260
gccttgagct aaccccaagg ctgcctctgg gccatgccag ccagagcag tggccctcca    4320
ccttgttcct gccctttaac tttcagaggc aataggtaaa tgggcccatt aggtccctca   4380
ctccacagag tgagccagtg agggcagtcc tgcaacatgt atttatggag tgcctgctgt   4440
ggaccctgtc ttctgggcac agtggactca gcagtgacca caccaacact gacccttgaa   4500
ccaataaagg aacaaatgac tattaaagca caaaaaaaaa a                       4541
```

FIG. 1B-1  SEQ ID NO: 2

| | | | | | | | | | | | | | | |
|---|---|---|---|---|---|---|---|---|---|---|---|---|---|---|
| Met | Glu | Leu | Leu | Pro 5 | Pro | Leu | Pro | Gln 10 | Ser | Phe | Leu | Leu | Leu 15 | Leu |
| Leu | Pro | Ala | Lys 20 | Pro | Ala | Ala | Gly | Glu 25 | Asp | Trp | Gln | Cys | Pro 30 | Arg | Thr |
| Pro | Tyr | Ala 35 | Ala | Ser | Arg | Asp | Phe 40 | Asp | Val | Lys | Tyr | Val 45 | Val | Pro | Ser |
| Phe | Ser 50 | Ala | Gly | Gly | Leu | Val 55 | Gln | Ala | Met | Val | Thr 60 | Tyr | Glu | Gly | Asp |
| Arg 65 | Asn | Glu | Ser | Ala | Val 70 | Phe | Val | Ala | Ile | Arg 75 | Asn | Arg | Leu | His | Val 80 |
| Leu | Gly | Pro | Asp | Leu 85 | Lys | Ser | Val | Gln | Ser 90 | Leu | Ala | Thr | Gly | Pro 95 | Ala |
| Gly | Asp | Pro | Gly 100 | Cys | Gln | Thr | Cys | Ala 105 | Ala | Cys | Gly | Pro | Gly 110 | Pro | His |
| Gly | Pro | Pro 115 | Gly | Asp | Thr | Asp | Thr 120 | Lys | Val | Leu | Val | Leu 125 | Asp | Pro | Ala |
| Leu | Pro 130 | Ala | Leu | Val | Ser | Cys 135 | Gly | Ser | Ser | Leu | Gln 140 | Gly | Arg | Cys | Phe |
| Leu 145 | His | Asp | Leu | Glu | Pro 150 | Gln | Gly | Thr | Ala | Val 155 | His | Leu | Ala | Ala | Pro 160 |
| Ala | Cys | Leu | Phe | Ser 165 | Ala | His | His | Asn | Arg 170 | Pro | Asp | Asp | Cys | Pro 175 | Asp |
| Cys | Val | Ala | Ser 180 | Pro | Leu | Gly | Thr | Arg 185 | Val | Thr | Val | Val | Glu 190 | Gln | Gly |
| Gln | Ala | Ser 195 | Tyr | Phe | Tyr | Val | Ala 200 | Ser | Ser | Leu | Asp | Ala 205 | Ala | Val | Ala |
| Gly | Ser 210 | Phe | Ser | Pro | Arg | Ser 215 | Val | Ser | Ile | Arg | Arg 220 | Leu | Lys | Ala | Asp |
| Ala 225 | Ser | Gly | Phe | Ala | Pro 230 | Gly | Phe | Val | Ala | Leu 235 | Ser | Val | Leu | Pro | Lys 240 |
| His | Leu | Val | Ser | Tyr 245 | Ser | Ile | Glu | Tyr | Val 250 | His | Ser | Phe | His | Thr 255 | Gly |
| Ala | Phe | Val | Tyr | Phe 260 | Leu | Thr | Val | Gln | Pro 265 | Ala | Ser | Val | Thr 270 | Asp | Asp |
| Pro | Ser | Ala 275 | Leu | His | Thr | Arg | Leu 280 | Ala | Arg | Leu | Ser | Ala 285 | Thr | Glu | Pro |
| Glu | Leu 290 | Gly | Asp | Tyr | Arg | Glu 295 | Leu | Val | Leu | Asp | Cys 300 | Arg | Phe | Ala | Pro |
| Lys 305 | Arg | Arg | Arg | Arg | Gly 310 | Ala | Pro | Glu | Gly | Gly 315 | Gln | Pro | Tyr | Pro | Val 320 |
| Leu | Gln | Val | Ala | His 325 | Ser | Ala | Pro | Val | Gly 330 | Ala | Gln | Leu | Ala | Thr 335 | Glu |
| Leu | Ser | Ile | Ala 340 | Glu | Gly | Gln | Glu | Val 345 | Leu | Phe | Gly | Val | Phe 350 | Val | Thr |
| Gly | Lys | Asp 355 | Gly | Gly | Pro | Gly | Val 360 | Gly | Pro | Asn | Ser | Val 365 | Val | Cys | Ala |
| Phe | Pro 370 | Ile | Asp | Leu | Leu | Asp 375 | Thr | Leu | Ile | Asp | Glu 380 | Gly | Val | Glu | Arg |
| Cys 385 | Cys | Glu | Ser | Pro | Val 390 | His | Pro | Gly | Leu | Arg 395 | Arg | Gly | Leu | Asp | Phe 400 |
| Phe | Gln | Ser | Pro | Ser 405 | Phe | Cys | Pro | Asn | Pro 410 | Pro | Gly | Leu | Glu | Ala 415 | Leu |
| Ser | Pro | Asn | Thr 420 | Ser | Cys | Arg | His | Phe 425 | Pro | Leu | Leu | Val | Ser 430 | Ser | Ser |
| Phe | Ser | Arg 435 | Val | Asp | Leu | Phe | Asn 440 | Gly | Leu | Leu | Gly | Pro 445 | Val | Gln | Val |
| Thr | Ala | Leu 450 | Tyr | Val | Thr | Arg | Leu 455 | Asp | Asn | Val | Thr | Val 460 | Ala | His | Met |
| Gly 465 | Thr | Met | Asp | Gly | Arg 470 | Ile | Leu | Gln | Val | Glu 475 | Leu | Val | Arg | Ser | Leu 480 |

FIG. 1B-2  SEQ ID NO: 2 cont.

```
Asn Tyr Leu Leu Tyr Val Ser Asn Phe Ser Leu Gly Asp Ser Gly Gln
            485             490             495
Pro Val Gln Arg Asp Val Ser Arg Leu Gly Asp His Leu Leu Phe Ala
        500             505             510
Ser Gly Asp Gln Val Phe Gln Val Pro Ile Arg Gly Pro Gly Cys Arg
        515             520             525
His Phe Leu Thr Cys Gly Arg Cys Leu Arg Ala Trp His Phe Met Gly
    530             535             540
Cys Gly Trp Cys Gly Asn Met Cys Gly Gln Gln Lys Glu Cys Pro Gly
545             550             555             560
Ser Trp Gln Gln Asp His Cys Pro Pro Lys Leu Thr Glu Phe His Pro
            565             570             575
His Ser Gly Pro Leu Arg Gly Ser Thr Arg Leu Thr Leu Cys Gly Ser
            580             585             590
Asn Phe Tyr Leu His Pro Ser Gly Leu Val Pro Glu Gly Thr His Gln
            595             600             605
Val Thr Val Gly Gln Ser Pro Cys Arg Pro Leu Pro Lys Asp Ser Ser
    610             615             620
Lys Leu Arg Pro Val Pro Arg Lys Asp Phe Val Glu Glu Phe Glu Cys
625             630             635             640
Glu Leu Glu Pro Leu Gly Thr Gln Ala Val Gly Pro Thr Asn Val Ser
            645             650             655
Leu Thr Val Thr Asn Met Pro Pro Gly Lys His Phe Arg Val Asp Gly
            660             665             670
Thr Ser Val Leu Arg Gly Phe Ser Phe Met Glu Pro Val Leu Ile Ala
        675             680             685
Val Gln Pro Leu Phe Gly Pro Arg Ala Gly Gly Thr Cys Leu Thr Leu
    690             695             700
Glu Gly Gln Ser Leu Ser Val Gly Thr Ser Arg Ala Val Leu Val Asn
705             710             715             720
Gly Thr Glu Cys Leu Leu Ala Arg Val Ser Glu Gly Gln Leu Leu Cys
            725             730             735
Ala Thr Pro Pro Gly Ala Thr Val Ala Ser Val Pro Leu Ser Leu Gln
            740             745             750
Val Gly Gly Ala Gln Val Pro Gly Ser Trp Thr Phe Gln Tyr Arg Glu
        755             760             765
Asp Pro Val Val Leu Ser Ile Ser Pro Asn Cys Gly Tyr Ile Asn Ser
    770             775             780
His Ile Thr Ile Cys Gly Gln His Leu Thr Ser Ala Trp His Leu Val
785             790             795             800
Leu Ser Phe His Asp Gly Leu Arg Ala Val Glu Ser Arg Cys Glu Arg
            805             810             815
Gln Leu Pro Glu Gln Gln Leu Cys Arg Leu Pro Glu Tyr Val Val Arg
        820             825             830
Asp Pro Gln Gly Trp Val Ala Gly Asn Leu Ser Ala Arg Gly Asp Gly
    835             840             845
Ala Ala Gly Phe Thr Leu Pro Gly Phe Arg Phe Leu Pro Pro His
850             855             860
Pro Pro Ser Ala Asn Leu Val Pro Leu Lys Pro Glu Glu His Ala Ile
865             870             875             880
Lys Phe Glu Tyr Ile Gly Leu Gly Ala Val Ala Asp Cys Val Gly Ile
            885             890             895
Asn Val Thr Val Gly Gly Glu Ser Cys Gln His Glu Phe Arg Gly Asp
            900             905             910
Met Val Val Cys Pro Leu Pro Pro Ser Leu Gln Leu Gly Gln Asp Gly
        915             920             925
Ala Pro Leu Gln Val Cys Val Asp Gly Glu Cys His Ile Leu Gly Arg
    930             935             940
Val Val Arg Pro Gly Pro Asp Gly Val Pro Gln Ser Thr Leu Leu Gly
945             950             955             960
```

FIG. 1B-3            SEQ ID NO: 2 cont.

```
Ile Leu Leu Pro Leu Leu Leu Leu Val Ala Ala Leu Ala Thr Ala Leu
            965             970             975
Val Phe Ser Tyr Trp Trp Arg Arg Lys Gln Leu Val Leu Pro Pro Asn
            980             985             990
Leu Asn Asp Leu Ala Ser Leu Asp Gln Thr Ala Gly Ala Thr Pro Leu
            995             1000            1005
Pro Ile Leu Tyr Ser Gly Ser Asp Tyr Arg Ser Gly Leu Ala Leu Pro
            1010            1015            1020
Ala Ile Asp Gly Leu Asp Ser Thr Thr Cys Val His Gly Ala Ser Phe
1025            1030            1035            1040
Ser Asp Ser Glu Asp Glu Ser Cys Val Pro Leu Leu Arg Lys Glu Ser
                1045            1050            1055
Ile Gln Leu Arg Asp Leu Asp Ser Ala Leu Leu Ala Glu Val Lys Asp
                1060            1065            1070
Val Leu Ile Pro His Glu Arg Val Val Thr His Ser Asp Arg Val Ile
            1075            1080            1085
Gly Lys Gly His Phe Gly Val Val Tyr His Gly Glu Tyr Ile Asp Gln
            1090            1095            1100
Ala Gln Asn Arg Ile Gln Cys Ala Ile Lys Ser Leu Ser Arg Ile Thr
1105            1110            1115            1120
Glu Met Gln Gln Val Glu Ala Phe Leu Arg Glu Gly Leu Leu Met Arg
                1125            1130            1135
Gly Leu Asn His Pro Asn Val Leu Ala Leu Ile Gly Ile Met Leu Pro
            1140            1145            1150
Pro Glu Gly Leu Pro His Val Leu Leu Pro Tyr Met Cys His Gly Asp
            1155            1160            1165
Leu Leu Gln Phe Ile Arg Ser Pro Gln Arg Asn Pro Thr Val Lys Asp
            1170            1175            1180
Leu Ile Ser Phe Gly Leu Gln Val Ala Arg Gly Met Glu Tyr Leu Ala
1185            1190            1195            1200
Glu Gln Lys Phe Val His Arg Asp Leu Ala Ala Arg Asn Cys Met Leu
                1205            1210            1215
Asp Glu Ser Phe Thr Val Lys Val Ala Asp Phe Gly Leu Ala Arg Asp
                1220            1225            1230
Ile Leu Asp Arg Glu Tyr Tyr Ser Val Gln Gln His Arg His Ala Arg
            1235            1240            1245
Leu Pro Val Lys Trp Met Ala Leu Glu Ser Leu Gln Thr Tyr Arg Phe
            1250            1255            1260
Thr Thr Lys Ser Asp Val Trp Ser Phe Gly Val Leu Leu Trp Glu Leu
1265            1270            1275            1280
Leu Thr Arg Gly Ala Pro Pro Tyr Arg His Ile Asp Pro Phe Asp Leu
                1285            1290            1295
Thr His Phe Leu Ala Gln Gly Arg Arg Leu Pro Gln Pro Glu Tyr Cys
            1300            1305            1310
Pro Asp Ser Leu Tyr Gln Val Met Gln Gln Cys Trp Glu Ala Asp Pro
            1315            1320            1325
Ala Val Arg Pro Thr Phe Arg Val Leu Val Gly Glu Val Glu Gln Ile
            1330            1335            1340
Val Ser Ala Leu Leu Gly Asp His Tyr Val Gln Leu Pro Ala Thr Tyr
1345            1350            1355            1360
Met Asn Leu Gly Pro Ser Thr Ser His Glu Met Asn Val Arg Pro Glu
                1365            1370            1375
Gln Pro Gln Phe Ser Pro Met Pro Gly Asn Val Arg Arg Pro Arg Pro
                1380            1385            1390
Leu Ser Glu Pro Pro Arg Pro Thr
            1395            1400
```

FIG. 1C-1  Coding Sequence (SEQ ID NO: 1 & 2)

```
atg gag ctc ctc ccg ccg ctg cct cag tcc ttc ctg ttg ctg ctg    48
Met Glu Leu Leu Pro Pro Leu Pro Gln Ser Phe Leu Leu Leu Leu
                5               10              15
ttg cct gcc aag ccc gcg gcg ggc gag gac tgg cag tgc ccg cgc acc   96
Leu Pro Ala Lys Pro Ala Ala Gly Glu Asp Trp Gln Cys Pro Arg Thr
            20              25              30
ccc tac gcg gcc tct cgc gac ttt gac gtg aag tac gtg gtg ccc agc  144
Pro Tyr Ala Ala Ser Arg Asp Phe Asp Val Lys Tyr Val Val Pro Ser
            35              40              45
ttc tcc gcc gga ggc ctg gta cag gcc atg gtg acc tac gag ggc gac  192
Phe Ser Ala Gly Gly Leu Val Gln Ala Met Val Thr Tyr Glu Gly Asp
        50              55              60
aga aat gag agt gct gtg ttt gta gcc ata cgc aat cgc ctg cat gtg  240
Arg Asn Glu Ser Ala Val Phe Val Ala Ile Arg Asn Arg Leu His Val
65              70              75              80
ctt ggg cct gac ctg aag tct gtc cag agc ctg gcc acg ggc cct gct  288
Leu Gly Pro Asp Leu Lys Ser Val Gln Ser Leu Ala Thr Gly Pro Ala
                85              90              95
gga gac cct ggc tgc cag acg tgt gca gcc tgt ggc cca gga ccc cac  336
Gly Asp Pro Gly Cys Gln Thr Cys Ala Ala Cys Gly Pro Gly Pro His
            100             105             110
ggc cct ccc ggt gac aca gac aca aag gtg ctg gtg ctg gat ccc gcg  384
Gly Pro Pro Gly Asp Thr Asp Thr Lys Val Leu Val Leu Asp Pro Ala
            115             120             125
ctg cct gcg ctg gtc agt tgt ggc tcc agc ctg cag ggc cgc tgc ttc  432
Leu Pro Ala Leu Val Ser Cys Gly Ser Ser Leu Gln Gly Arg Cys Phe
        130             135             140
ctg cat gac cta gag ccc caa ggg aca gcc gtg cat ctg gca gcg cca  480
Leu His Asp Leu Glu Pro Gln Gly Thr Ala Val His Leu Ala Ala Pro
145             150             155             160
gcc tgc ctc ttc tca gcc cat aac cgg ccc gat gac tgc ccc gac  528
Ala Cys Leu Phe Ser Ala His His Asn Arg Pro Asp Asp Cys Pro Asp
                165             170             175
tgt gtg gcc agc cca ttg ggc acc cgt gta act gtg gtt gag caa ggc  576
Cys Val Ala Ser Pro Leu Gly Thr Arg Val Thr Val Val Glu Gln Gly
            180             185             190
cag gcc tcc tat ttc tac gtg gca tcc tca ctg gac gca gcc gtg gct  624
Gln Ala Ser Tyr Phe Tyr Val Ala Ser Ser Leu Asp Ala Ala Val Ala
            195             200             205
ggc agc ttc agc cca cgc tca gtg tct atc agg cgt ctc aag gct gac  672
Gly Ser Phe Ser Pro Arg Ser Val Ser Ile Arg Arg Leu Lys Ala Asp
        210             215             220
gcc tcg gga ttc gca ccg ggc ttt gtg gcg ttg tca gtg ctg ccc aag  720
Ala Ser Gly Phe Ala Pro Gly Phe Val Ala Leu Ser Val Leu Pro Lys
225             230             235             240
cat ctt gtc tcc tac agt att gaa tac gtg cac agc ttc cac acg gga  768
His Leu Val Ser Tyr Ser Ile Glu Tyr Val His Ser Phe His Thr Gly
                245             250             255
gcc ttc gta tac ttc ctg act gta cag ccg gcc agc gtg aca gat gat  816
Ala Phe Val Tyr Phe Leu Thr Val Gln Pro Ala Ser Val Thr Asp Asp
            260             265             270
cct agt gcc ctg cac aca cgc ctg gca cgg ctt agc gcc act gag cca  864
Pro Ser Ala Leu His Thr Arg Leu Ala Arg Leu Ser Ala Thr Glu Pro
        275             280             285
gag ttg ggt gac tat cgg gag ctg gtc ctc gac tgc aga ttt gct cca  912
Glu Leu Gly Asp Tyr Arg Glu Leu Val Leu Asp Cys Arg Phe Ala Pro
290             295             300
aaa cgc agg cgc cgg ggg gcc cca gaa ggc gga cag ccc tac cct gtg  960
Lys Arg Arg Arg Arg Gly Ala Pro Glu Gly Gly Gln Pro Tyr Pro Val
305             310             315             320
```

FIG. 1C-2          Coding Sequence (SEQ ID NO: 1 & 2) cont.

| | | | | | | | | | | | | | | | | |
|---|---|---|---|---|---|---|---|---|---|---|---|---|---|---|---|---|
| ctg | cag | gtg | gcc | cac | tcc | gct | cca | gtg | ggt | gcc | caa | ctt | gcc | act | gag | 1008 |
| Leu | Gln | Val | Ala | His | Ser | Ala | Pro | Val | Gly | Ala | Gln | Leu | Ala | Thr | Glu | |
| | | | | 325 | | | | | 330 | | | | | 335 | | |
| ctg | agc | atc | gcc | gag | ggc | cag | gaa | gta | cta | ttt | ggg | gtc | ttt | gtg | act | 1056 |
| Leu | Ser | Ile | Ala | Glu | Gly | Gln | Glu | Val | Leu | Phe | Gly | Val | Phe | Val | Thr | |
| | | | 340 | | | | | 345 | | | | | 350 | | | |
| ggc | aag | gat | ggt | ggt | cct | ggc | gtg | ggc | ccc | aac | tct | gtc | gtc | tgt | gcc | 1104 |
| Gly | Lys | Asp | Gly | Gly | Pro | Gly | Val | Gly | Pro | Asn | Ser | Val | Val | Cys | Ala | |
| | | 355 | | | | | 360 | | | | | 365 | | | | |
| ttc | ccc | att | gac | ctg | ctg | gac | aca | cta | att | gat | gag | ggt | gtg | gag | cgc | 1152 |
| Phe | Pro | Ile | Asp | Leu | Leu | Asp | Thr | Leu | Ile | Asp | Glu | Gly | Val | Glu | Arg | |
| | 370 | | | | | 375 | | | | | 380 | | | | | |
| tgt | tgt | gaa | tcc | cca | gtc | cat | cca | ggc | ctc | cgg | cga | ggc | ctc | gac | ttc | 1200 |
| Cys | Cys | Glu | Ser | Pro | Val | His | Pro | Gly | Leu | Arg | Arg | Gly | Leu | Asp | Phe | |
| 385 | | | | | 390 | | | | | 395 | | | | | 400 | |
| ttc | cag | tcg | ccc | agt | ttt | tgc | ccc | aac | ccg | cct | ggc | ctg | gaa | gcc | ctc | 1248 |
| Phe | Gln | Ser | Pro | Ser | Phe | Cys | Pro | Asn | Pro | Pro | Gly | Leu | Glu | Ala | Leu | |
| | | | | 405 | | | | | 410 | | | | | 415 | | |
| agc | ccc | aac | acc | agc | tgc | cgc | cac | ttc | cct | ctg | ctg | gtc | agt | agc | agc | 1296 |
| Ser | Pro | Asn | Thr | Ser | Cys | Arg | His | Phe | Pro | Leu | Leu | Val | Ser | Ser | Ser | |
| | | | 420 | | | | | 425 | | | | | 430 | | | |
| ttc | tca | cgt | gtg | gac | cta | ttc | aat | ggg | ctg | ttg | gga | cca | gta | cag | gtc | 1344 |
| Phe | Ser | Arg | Val | Asp | Leu | Phe | Asn | Gly | Leu | Leu | Gly | Pro | Val | Gln | Val | |
| | | 435 | | | | | 440 | | | | | 445 | | | | |
| act | gca | ttg | tat | gtg | aca | cgc | ctt | gac | aac | gtc | aca | gtg | gca | cac | atg | 1392 |
| Thr | Ala | Leu | Tyr | Val | Thr | Arg | Leu | Asp | Asn | Val | Thr | Val | Ala | His | Met | |
| | 450 | | | | | 455 | | | | | 460 | | | | | |
| ggc | aca | atg | gat | ggg | cgt | atc | ctg | cag | gtg | gag | ctg | gtc | agg | tca | cta | 1440 |
| Gly | Thr | Met | Asp | Gly | Arg | Ile | Leu | Gln | Val | Glu | Leu | Val | Arg | Ser | Leu | |
| 465 | | | | | 470 | | | | | 475 | | | | | 480 | |
| aac | tac | ttg | ctg | tat | gtg | tcc | aac | ttc | tca | ctg | ggt | gac | agt | ggg | cag | 1488 |
| Asn | Tyr | Leu | Leu | Tyr | Val | Ser | Asn | Phe | Ser | Leu | Gly | Asp | Ser | Gly | Gln | |
| | | | | 485 | | | | | 490 | | | | | 495 | | |
| ccc | gtg | cag | cgg | gat | gtc | agt | cgt | ctt | ggg | gac | cac | cta | ctc | ttt | gcc | 1536 |
| Pro | Val | Gln | Arg | Asp | Val | Ser | Arg | Leu | Gly | Asp | His | Leu | Leu | Phe | Ala | |
| | | | 500 | | | | | 505 | | | | | 510 | | | |
| tct | ggg | gac | cag | gtt | ttc | cag | gta | cct | atc | cga | ggc | cct | ggc | tgc | cgc | 1584 |
| Ser | Gly | Asp | Gln | Val | Phe | Gln | Val | Pro | Ile | Arg | Gly | Pro | Gly | Cys | Arg | |
| | | 515 | | | | | 520 | | | | | 525 | | | | |
| cac | ttc | ctg | acc | tgt | ggg | cgt | tgc | cta | agg | gca | tgg | cat | ttc | atg | ggc | 1632 |
| His | Phe | Leu | Thr | Cys | Gly | Arg | Cys | Leu | Arg | Ala | Trp | His | Phe | Met | Gly | |
| | 530 | | | | | 535 | | | | | 540 | | | | | |
| tgt | ggc | tgg | tgt | ggg | aac | atg | tgc | ggc | cag | cag | aag | gag | tgt | cct | ggc | 1680 |
| Cys | Gly | Trp | Cys | Gly | Asn | Met | Cys | Gly | Gln | Gln | Lys | Glu | Cys | Pro | Gly | |
| 545 | | | | | 550 | | | | | 555 | | | | | 560 | |
| tcc | tgg | caa | cag | gac | cac | tgc | cca | cct | aag | ctt | act | gag | ttc | cac | ccc | 1728 |
| Ser | Trp | Gln | Gln | Asp | His | Cys | Pro | Pro | Lys | Leu | Thr | Glu | Phe | His | Pro | |
| | | | | 565 | | | | | 570 | | | | | 575 | | |
| cac | agt | gga | cct | cta | agg | ggc | agt | aca | agg | ctg | acc | ctg | tgt | ggc | tcc | 1776 |
| His | Ser | Gly | Pro | Leu | Arg | Gly | Ser | Thr | Arg | Leu | Thr | Leu | Cys | Gly | Ser | |
| | | | 580 | | | | | 585 | | | | | 590 | | | |
| aac | ttc | tac | ctt | cac | cct | tct | ggt | ctg | gtg | cct | gag | gga | acc | cat | cag | 1824 |
| Asn | Phe | Tyr | Leu | His | Pro | Ser | Gly | Leu | Val | Pro | Glu | Gly | Thr | His | Gln | |
| | | 595 | | | | | 600 | | | | | 605 | | | | |
| gtc | act | gtg | ggc | caa | agt | ccc | tgc | cgg | cca | ctg | ccc | aag | gac | agc | tca | 1872 |
| Val | Thr | Val | Gly | Gln | Ser | Pro | Cys | Arg | Pro | Leu | Pro | Lys | Asp | Ser | Ser | |
| | 610 | | | | | 615 | | | | | 620 | | | | | |
| aaa | ctc | aga | cca | gtg | ccc | cgg | aaa | gac | ttt | gta | gag | gag | ttt | gag | tgt | 1920 |
| Lys | Leu | Arg | Pro | Val | Pro | Arg | Lys | Asp | Phe | Val | Glu | Glu | Phe | Glu | Cys | |
| 625 | | | | | 630 | | | | | 635 | | | | | 640 | |

FIG. 1C-3  Coding Sequence (SEQ ID NO: 1 & 2) cont.

```
gaa ctg gag ccc ttg ggc acc cag gca gtg ggg cct acc aac gtc agc  1968
Glu Leu Glu Pro Leu Gly Thr Gln Ala Val Gly Pro Thr Asn Val Ser
            645             650                 655
ctc acc gtg act aac atg cca ccg ggc aag cac ttc cgg gta gac ggc  2016
Leu Thr Val Thr Asn Met Pro Pro Gly Lys His Phe Arg Val Asp Gly
        660                 665                 670
acc tcc gtg ctg aga ggc ttc tct ttc atg gag cca gtg ctg ata gca  2064
Thr Ser Val Leu Arg Gly Phe Ser Phe Met Glu Pro Val Leu Ile Ala
        675                 680                 685
gtg caa ccc ctc ttt ggc cca cgg gca gga ggc acc tgt ctc act ctt  2112
Val Gln Pro Leu Phe Gly Pro Arg Ala Gly Gly Thr Cys Leu Thr Leu
    690                 695                 700
gaa ggc cag agt ctg tct gta ggc acc agc cgg gct gtg ctg gtc aat  2160
Glu Gly Gln Ser Leu Ser Val Gly Thr Ser Arg Ala Val Leu Val Asn
705                 710                 715                 720
ggg act gag tgt ctg cta gca cgg gtc agt gag ggg cag ctt tta tgt  2208
Gly Thr Glu Cys Leu Leu Ala Arg Val Ser Glu Gly Gln Leu Leu Cys
                725                 730                 735
gcc aca ccc cct ggg gcc acg gtg gcc agt gtc ccc ctt agc ctg cag  2256
Ala Thr Pro Pro Gly Ala Thr Val Ala Ser Val Pro Leu Ser Leu Gln
            740                 745                 750
gtg ggg ggt gcc cag gta cct ggt tcc tgg acc ttc cag tac aga gaa  2304
Val Gly Gly Ala Gln Val Pro Gly Ser Trp Thr Phe Gln Tyr Arg Glu
        755                 760                 765
gac cct gtc gtg cta agc atc agc ccc aac tgt ggc tac atc aac tcc  2352
Asp Pro Val Val Leu Ser Ile Ser Pro Asn Cys Gly Tyr Ile Asn Ser
        770                 775                 780
cac atc acc atc tgt ggc cag cat cta act tca gca tgg cac tta gtg  2400
His Ile Thr Ile Cys Gly Gln His Leu Thr Ser Ala Trp His Leu Val
785                 790                 795                 800
ctg tca ttc cat gac ggg ctt agg gca gtg gaa agc agg tgt gag agg  2448
Leu Ser Phe His Asp Gly Leu Arg Ala Val Glu Ser Arg Cys Glu Arg
                805                 810                 815
cag ctt cca gag cag cag ctg tgc cgc ctt cct gaa tat gtg gtc cga  2496
Gln Leu Pro Glu Gln Gln Leu Cys Arg Leu Pro Glu Tyr Val Val Arg
            820                 825                 830
gac ccc cag gga tgg gtg gca ggg aat ctg agt gcc cga ggg gat gga  2544
Asp Pro Gln Gly Trp Val Ala Gly Asn Leu Ser Ala Arg Gly Asp Gly
        835                 840                 845
gct gct ggc ttt aca ctg cct ggc ttt cgc ttc cta ccc cca ccc cat  2592
Ala Ala Gly Phe Thr Leu Pro Gly Phe Arg Phe Leu Pro Pro Pro His
        850                 855                 860
cca ccc agt gcc aac cta gtt cca ctg aag cct gag gag cat gcc att  2640
Pro Pro Ser Ala Asn Leu Val Pro Leu Lys Pro Glu Glu His Ala Ile
865                 870                 875                 880
aag ttt gag tat att ggg ctg ggc gct gtg gct gac tgt gtg ggt atc  2688
Lys Phe Glu Tyr Ile Gly Leu Gly Ala Val Ala Asp Cys Val Gly Ile
                885                 890                 895
aac gtg acc gtg ggt ggt gag agc tgc cag cac gag ttc cgg ggg gac  2736
Asn Val Thr Val Gly Gly Glu Ser Cys Gln His Glu Phe Arg Gly Asp
            900                 905                 910
atg gtt gtc tgc ccc ctg ccc cca tcc ctg cag ctt ggc cag gat ggt  2784
Met Val Val Cys Pro Leu Pro Pro Ser Leu Gln Leu Gly Gln Asp Gly
        915                 920                 925
gcc cca ttg cag gtc tgc gta gat ggt gaa tgt cat atc ctg ggt aga  2832
Ala Pro Leu Gln Val Cys Val Asp Gly Glu Cys His Ile Leu Gly Arg
        930                 935                 940
gtg gtg cgg cca ggg cca gat ggg gtc cca cag agc acg ctc ctt ggt  2880
Val Val Arg Pro Gly Pro Asp Gly Val Pro Gln Ser Thr Leu Leu Gly
945                 950                 955                 960
```

FIG. 1C-4  Coding Sequence (SEQ ID NO: 1 & 2) cont.

```
atc ctg ctg cct ttg ctg ctg ctt gtg gct gca ctg gcg act gca ctg  2928
Ile Leu Leu Pro Leu Leu Leu Leu Val Ala Ala Leu Ala Thr Ala Leu
            965                 970                 975
gtc ttc agc tac tgg tgg cgg agg aag cag cta gtt ctt cct ccc aac  2976
Val Phe Ser Tyr Trp Trp Arg Arg Lys Gln Leu Val Leu Pro Pro Asn
            980                 985                 990
ctg aat gac ctg gca tcc ctg gac cag act gct gga gcc aca ccc ctg  3024
Leu Asn Asp Leu Ala Ser Leu Asp Gln Thr Ala Gly Ala Thr Pro Leu
            995                1000                1005
cct att ctg tac tcg ggc tct gac tac aga agt ggc ctt gca ctc cct  3072
Pro Ile Leu Tyr Ser Gly Ser Asp Tyr Arg Ser Gly Leu Ala Leu Pro
   1010                1015                1020
gcc att gat ggt ctg gat tcc acc act tgt gtc cat gga gca tcc ttc  3120
Ala Ile Asp Gly Leu Asp Ser Thr Thr Cys Val His Gly Ala Ser Phe
1025                1030                1035                1040
tcc gat agt gaa gat gaa tcc tgt gtg cca ctg ctg cgg aaa gag tcc  3168
Ser Asp Ser Glu Asp Glu Ser Cys Val Pro Leu Leu Arg Lys Glu Ser
                   1045                1050                1055
atc cag cta agg gac ctg gac tct gcg ctc ttg gct gag gtc aag gat  3216
Ile Gln Leu Arg Asp Leu Asp Ser Ala Leu Leu Ala Glu Val Lys Asp
           1060                1065                1070
gtg ctg att ccc cat gag cgg gtg gtc acc cac agt gac cga gtc att  3264
Val Leu Ile Pro His Glu Arg Val Val Thr His Ser Asp Arg Val Ile
       1075                1080                1085
ggc aaa ggc cac ttt gga gtt gtc tac cac gga gaa tac ata gac cag  3312
Gly Lys Gly His Phe Gly Val Val Tyr His Gly Glu Tyr Ile Asp Gln
   1090                1095                1100
gcc cag aat cga atc caa tgt gcc atc aag tca cta agt cgc atc aca  3360
Ala Gln Asn Arg Ile Gln Cys Ala Ile Lys Ser Leu Ser Arg Ile Thr
1105                1110                1115                1120
gag atg cag cag gtg gag gcc ttc ctg cga gag ggg ctg ctc atg cgt  3408
Glu Met Gln Gln Val Glu Ala Phe Leu Arg Glu Gly Leu Leu Met Arg
                   1125                1130                1135
ggc ctg aac cac ccg aat gtg ctg gct ctc att ggt atc atg ttg cca  3456
Gly Leu Asn His Pro Asn Val Leu Ala Leu Ile Gly Ile Met Leu Pro
           1140                1145                1150
cct gag ggc ctg ccc cat gtg ctg ctg ccc tat atg tgc cac ggt gac  3504
Pro Glu Gly Leu Pro His Val Leu Leu Pro Tyr Met Cys His Gly Asp
       1155                1160                1165
ctg ctc cag ttc atc cgc tca cct cag cgg aac ccc acc gtg aag gac  3552
Leu Leu Gln Phe Ile Arg Ser Pro Gln Arg Asn Pro Thr Val Lys Asp
   1170                1175                1180
ctc atc agc ttt ggc ctg cag gta gcc cgc ggt atg gag tac ctg gca  3600
Leu Ile Ser Phe Gly Leu Gln Val Ala Arg Gly Met Glu Tyr Leu Ala
1185                1190                1195                1200
gag cag aag ttt gtg cac agg gac ctg gct gcg cgg aac tgc atg ctg  3648
Glu Gln Lys Phe Val His Arg Asp Leu Ala Ala Arg Asn Cys Met Leu
                   1205                1210                1215
gac gag tca ttc aca gtc aag gtg gct gac ttt ggt ttg gcc cgc gac  3696
Asp Glu Ser Phe Thr Val Lys Val Ala Asp Phe Gly Leu Ala Arg Asp
           1220                1225                1230
atc ctg gac agg gag tac tat agt gtt caa cag cat cgc cac gct cgc  3744
Ile Leu Asp Arg Glu Tyr Tyr Ser Val Gln Gln His Arg His Ala Arg
       1235                1240                1245
cta cct gtg aag tgg atg gcg ctg gag agc ctg cag acc tat aga ttt  3792
Leu Pro Val Lys Trp Met Ala Leu Glu Ser Leu Gln Thr Tyr Arg Phe
   1250                1255                1260
acc acc aag tct gat gtg tgg tca ttt ggt gtg ctg ctg tgg gaa ctg  3840
Thr Thr Lys Ser Asp Val Trp Ser Phe Gly Val Leu Leu Trp Glu Leu
1265                1270                1275                1280
```

FIG. 1C-5          Coding Sequence (SEQ ID NO: 1 & 2) cont.

```
ctg aca cgg ggt gcc cca cca tac cgc cac att gac cct ttt gac ctt 3888
Leu Thr Arg Gly Ala Pro Pro Tyr Arg His Ile Asp Pro Phe Asp Leu
            1285                    1290                    1295
acc cac ttc ctg gcc cag ggt cgg cgc ctg ccc cag cct gag tat tgc 3936
Thr His Phe Leu Ala Gln Gly Arg Arg Leu Pro Gln Pro Glu Tyr Cys
            1300                    1305                    1310
cct gat tct ctg tac caa gtg atg cag caa tgc tgg gag gca gac cca 3984
Pro Asp Ser Leu Tyr Gln Val Met Gln Gln Cys Trp Glu Ala Asp Pro
            1315                    1320                    1325
gca gtg cga ccc acc ttc aga gta cta gtg ggg gag gtg gag cag ata 4032
Ala Val Arg Pro Thr Phe Arg Val Leu Val Gly Glu Val Glu Gln Ile
    1330                    1335                    1340
gtg tct gca ctg ctt ggg gac cat tat gtg cag ctg cca gca acc tac 4080
Val Ser Ala Leu Leu Gly Asp His Tyr Val Gln Leu Pro Ala Thr Tyr
1345                    1350                    1355                    1360
atg aac ttg ggc ccc agc acc tcg cat gag atg aat gtg cgt cca gaa 4128
Met Asn Leu Gly Pro Ser Thr Ser His Glu Met Asn Val Arg Pro Glu
                1365                    1370                    1375
cag ccg cag ttc tca ccc atg cca ggg aat gta cgc cgg ccc cgg cca 4176
Gln Pro Gln Phe Ser Pro Met Pro Gly Asn Val Arg Arg Pro Arg Pro
            1380                    1385                    1390
ctc tca gag cct cct cgg ccc act                                   4200
Leu Ser Glu Pro Pro Arg Pro Thr
        1395                    1400
```

FIG. 2A-1  SEQ ID NO: 3

| | | | | | | |
|---|---|---|---|---|---|---|
| ggatcctcta | gggtcccagc | tcgcctcgat | ggagctcctc | ccgccgctgc | ctcagtcctt | 60 |
| cctgttgctg | ctgctgttgc | ctgccaagcc | cgcggcgggc | gaggactggc | agtgcccgcg | 120 |
| cacccctac | gcggcctctc | gcgactttga | cgtgaagtac | gtggtgccca | gcttctccgc | 180 |
| cggaggcctg | gtacaggcca | tggtgaccta | cgagggcgac | agaaatgaga | gtgctgtgtt | 240 |
| tgtagccata | cgcaatcgcc | tgcatgtgct | tgggcctgac | ctgaagtctg | tccagagcct | 300 |
| ggccacgggc | cctgctggag | accctggctg | ccagacgtgt | gcagcctgtg | gcccaggacc | 360 |
| ccacggccct | cccggtgaca | cagacacaaa | ggtgctggtg | ctggatcccg | cgctgcctgc | 420 |
| gctggtcagt | tgtggctcca | gcctgcaggg | ccgctgcttc | ctgcatgacc | tagagcccca | 480 |
| agggacagcc | gtgcatctgg | cagcgccagc | ctgcctcttc | tcagcccacc | ataaccggcc | 540 |
| cgatgactgc | cccgactgtg | tggccagccc | attgggcacc | cgtgtaactg | tggttgagca | 600 |
| aggccaggcc | tcctatttct | acgtggcatc | ctcactggac | gcagccgtgg | ctggcagctt | 660 |
| cagcccacgc | tcagtgtcta | tcaggcgtct | caaggctgac | gcctcgggat | tcgcaccggg | 720 |
| ctttgtggcg | ttgtcagtgc | tgcccaagca | tcttgtctcc | tacagtattg | aatacgtgca | 780 |
| cagcttccac | acgggagcct | tcgtatactt | cctgactgta | cagccggcca | gcgtgacaga | 840 |
| tgatcctagt | gccctgcaca | cacgcctggc | acggcttagc | gccactgagc | cagagttggg | 900 |
| tgactatcgg | gagctggtcc | tcgactgcag | atttgctcca | aaacgcaggc | gccggggggc | 960 |
| cccagaaggc | ggacagccct | accctgtgct | gcaggtggcc | cactccgctc | cagtgggtgc | 1020 |
| ccaacttgcc | actgagctga | gcatcgccga | gggccaggaa | gtactatttg | gggtctttgt | 1080 |
| gactggcaag | gatggtggtc | ctggcgtggg | ccccaactct | gtcgtctgtg | ccttccccat | 1140 |
| tgacctgctg | gacacactaa | ttgatgaggg | tgtggagcgc | tgttgtgaat | ccccagtcca | 1200 |
| tccaggcctc | cggcgaggcc | tcgacttctt | ccagtcgccc | agttttttgcc | ccaacccgcc | 1260 |
| tggcctggaa | gccctcagcc | ccaacaccag | ctgccgccac | ttccctctgc | tggtcagtag | 1320 |
| cagcttctca | cgtgtggacc | tattcaatgg | gctgttggga | ccagtacagg | tcactgcatt | 1380 |
| gtatgtgaca | cgccttgaca | acgtcacagt | ggcacacatg | ggcacaatgg | atgggcgtat | 1440 |
| cctgcaggtg | gagctggtca | ggtcactaaa | ctacttgctg | tatgtgtcca | acttctcact | 1500 |
| gggtgacagt | gggcagcccg | tgcagcggga | tgtcagtcgt | cttggggacc | acctactctt | 1560 |
| tgcctctggg | gaccaggttt | tccaggtacc | tatccgaggc | cctggctgcc | gccacttcct | 1620 |
| gacctgtggg | cgttgcctaa | gggcatggca | tttcatgggc | tgtggctggt | gtgggaacat | 1680 |
| gtgcggccag | cagaaggagt | gtcctggctc | ctggcaacag | gaccactgcc | cacctaagct | 1740 |
| tactgagttc | cacccccaca | gtggacctct | aaggggcagt | acaaggctga | ccctgtgtgg | 1800 |
| ctccaacttc | taccttcacc | cttctggtct | ggtgcctgag | ggaacccatc | aggtcactgt | 1860 |
| gggccaaagt | ccctgccggc | cactgcccaa | ggacagctca | aaactcagac | cagtgccccg | 1920 |
| gaaagacttt | gtagaggagt | ttgagtgtga | actggagccc | ttgggcaccc | aggcagtggg | 1980 |
| gcctaccaac | gtcagcctca | ccgtgactaa | catgccaccg | ggcaagcact | tccgggtaga | 2040 |
| cggcacctcc | gtgctgagag | gcttctcttt | catggagcca | gtgctgatag | cagtgcaacc | 2100 |
| cctctttggc | ccacgggcag | gaggcacctg | tctcactctt | gaaggccaga | gtctgtctgt | 2160 |
| aggcaccagc | cgggctgtgc | tggtcaatgg | gactgagtgt | ctgctagcac | gggtcagtga | 2220 |
| ggggcagctt | ttatgtgcca | cacccctgg | ggccacggtg | gccagtgtcc | cccttagcct | 2280 |

FIG. 2A-2  SEQ ID NO: 3 cont.

| | | | | | | |
|---|---|---|---|---|---|---|
| gcaggtgggg | ggtgcccagg | tacctggttc | ctggaccttc | cagtacagag | aagaccctgt | 2340 |
| cgtgctaagc | atcagcccca | actgtggcta | catcaactcc | cacatcacca | tctgtggcca | 2400 |
| gcatctaact | tcagcatggc | acttagtgct | gtcattccat | gacgggctta | gggcagtgga | 2460 |
| aagcaggtgt | gagaggcagc | ttccagagca | gcagctgtgc | cgccttcctg | aatatgtggt | 2520 |
| ccgagacccc | cagggatggg | tggcagggaa | tctgagtgcc | cgaggggatg | gagctgctgg | 2580 |
| ctttacactg | cctggctttc | gcttcctacc | cccaccccat | ccacccagtg | ccaacctagt | 2640 |
| tccactgaag | cctgaggagc | atgccattaa | gtttgagtat | attgggctgg | gcgctgtggc | 2700 |
| tgactgtgtg | ggtatcaacg | tgaccgtggg | tggtgagagc | tgccagcacg | agttccgggg | 2760 |
| ggacatggtt | gtctgccccc | tgcccccatc | cctgcagctt | ggccaggatg | gtgcccatt | 2820 |
| gcaggtctgc | gtagatgcac | tccctgccat | tgatggtctg | gattccacca | cttgtgtcca | 2880 |
| tggagcatcc | ttctccgata | gtgaagatga | atcctgtgtg | ccactgctgc | ggaaagagtc | 2940 |
| catccagcta | agggacctgg | actctgcgct | cttggctgag | gtcaaggatg | tgctgattcc | 3000 |
| ccatgagcgg | gtggtcaccc | acagtgaccg | agtcattggc | aaaggccact | ttggagttgt | 3060 |
| ctaccacgga | gaatacatag | accaggccca | gaatcgaatc | caatgtgcca | tcaagtcact | 3120 |
| aagtcgcatc | acagagatgc | agcaggtgga | ggccttcctg | cgagagggc | tgctcatgcg | 3180 |
| tggcctgaac | cacccgaatg | tgctggctct | cattggtatc | atgttgccac | ctgagggcct | 3240 |
| gccccatgtg | ctgctgccct | atatgtgcca | cggtgacctg | ctccagttca | tccgctcacc | 3300 |
| tcagcggaac | cccaccgtga | aggacctcat | cagctttggc | ctgcaggtag | cccgcggcat | 3360 |
| ggagtacctg | gcagagcaga | agtttgtgca | cagggacctg | gctgcgcgga | actgcatgct | 3420 |
| ggacgagtca | ttcacagtca | aggtggctga | ctttggtttg | gcccgcgaca | tcctggacag | 3480 |
| ggagtactat | agtgttcaac | agcatcgcca | cgctcgccta | cctgtgaagt | ggatggcgct | 3540 |
| ggagagcctg | cagacctata | gatttaccac | caagtctgat | gtggtaccaa | gtgatgcagc | 3600 |
| aatgctggga | ggcagaccca | gcagtgcgac | ccaccttcag | agtactagtg | ggggaggtgg | 3660 |
| agcagatagt | gtctgcactg | cttgggacc | attatgtgca | gctgccagca | acctacatga | 3720 |
| acttgagcta | accccaaggc | tgcctctggg | ccatgccagg | ccagagcagt | ggccctccac | 3780 |
| cttgttcctg | cccttaact | ttcagaggca | ataggtaaat | gggcccatta | ggtccctcac | 3840 |
| tccacagagt | gagccagtga | gggcagtcct | gcaacatgta | tttatggagt | gcctgctgtg | 3900 |
| gaccctgtct | tctgggcaca | gtggactcag | cagtgaccac | accaacactg | acccttgaac | 3960 |
| caataaagga | acaaatgact | attaaagcac | aaaaaaaaaa | | | 4000 |

FIG. 2B-1
SEQ ID NO: 4

```
Met Glu Leu Leu Pro Pro Leu Pro Gln Ser Phe Leu Leu Leu Leu
              5               10                  15
Leu Pro Ala Lys Pro Ala Ala Gly Glu Asp Trp Gln Cys Pro Arg Thr
            20              25              30
Pro Tyr Ala Ala Ser Arg Asp Phe Asp Val Lys Tyr Val Val Pro Ser
            35              40              45
Phe Ser Ala Gly Gly Leu Val Gln Ala Met Val Thr Tyr Glu Gly Asp
    50              55              60
Arg Asn Glu Ser Ala Val Phe Val Ala Ile Arg Asn Arg Leu His Val
65              70              75              80
Leu Gly Pro Asp Leu Lys Ser Val Gln Ser Leu Ala Thr Gly Pro Ala
                85              90              95
Gly Asp Pro Gly Cys Gln Thr Cys Ala Ala Cys Gly Pro Gly Pro His
            100             105             110
Gly Pro Pro Gly Asp Thr Asp Thr Lys Val Leu Val Leu Asp Pro Ala
            115             120             125
Leu Pro Ala Leu Val Ser Cys Gly Ser Ser Leu Gln Gly Arg Cys Phe
    130             135             140
Leu His Asp Leu Glu Pro Gln Gly Thr Ala Val His Leu Ala Ala Pro
145             150             155             160
Ala Cys Leu Phe Ser Ala His His Asn Arg Pro Asp Asp Cys Pro Asp
                165             170             175
Cys Val Ala Ser Pro Leu Gly Thr Arg Val Thr Val Val Glu Gln Gly
            180             185             190
Gln Ala Ser Tyr Phe Tyr Val Ala Ser Ser Leu Asp Ala Ala Val Ala
            195             200             205
Gly Ser Phe Ser Pro Arg Ser Val Ser Ile Arg Arg Leu Lys Ala Asp
    210             215             220
Ala Ser Gly Phe Ala Pro Gly Phe Val Ala Leu Ser Val Leu Pro Lys
225             230             235             240
His Leu Val Ser Tyr Ser Ile Glu Tyr Val His Ser Phe His Thr Gly
                245             250             255
Ala Phe Val Tyr Phe Leu Thr Val Gln Pro Ala Ser Val Thr Asp Asp
            260             265             270
Pro Ser Ala Leu His Thr Arg Leu Ala Arg Leu Ser Ala Thr Glu Pro
            275             280             285
Glu Leu Gly Asp Tyr Arg Glu Leu Val Leu Asp Cys Arg Phe Ala Pro
    290             295             300
Lys Arg Arg Arg Arg Gly Ala Pro Glu Gly Gly Gln Pro Tyr Pro Val
305             310             315             320
Leu Gln Val Ala His Ser Ala Pro Val Gly Ala Gln Leu Ala Thr Glu
                325             330             335
Leu Ser Ile Ala Glu Gly Gln Glu Val Leu Phe Gly Val Phe Val Thr
            340             345             350
Gly Lys Asp Gly Gly Pro Gly Val Gly Pro Asn Ser Val Val Cys Ala
            355             360             365
Phe Pro Ile Asp Leu Leu Asp Thr Leu Ile Asp Glu Gly Val Glu Arg
    370             375             380
Cys Cys Glu Ser Pro Val His Pro Gly Leu Arg Arg Gly Leu Asp Phe
385             390             395             400
Phe Gln Ser Pro Ser Phe Cys Pro Asn Pro Pro Gly Leu Glu Ala Leu
                405             410             415
Ser Pro Asn Thr Ser Cys Arg His Phe Pro Leu Leu Val Ser Ser Ser
            420             425             430
Phe Ser Arg Val Asp Leu Phe Asn Gly Leu Leu Gly Pro Val Gln Val
            435             440             445
Thr Ala Leu Tyr Val Thr Arg Leu Asp Asn Val Thr Val Ala His Met
    450             455             460
Gly Thr Met Asp Gly Arg Ile Leu Gln Val Glu Leu Val Arg Ser Leu
465             470             475             480
```

FIG. 2B-2          SEQ ID NO: 4 cont.

```
Asn Tyr Leu Leu Tyr Val Ser Asn Phe Ser Leu Gly Asp Ser Gly Gln
            485                 490                 495
Pro Val Gln Arg Asp Val Ser Arg Leu Gly Asp His Leu Leu Phe Ala
        500                 505                 510
Ser Gly Asp Gln Val Phe Gln Val Pro Ile Arg Gly Pro Gly Cys Arg
            515                 520                 525
His Phe Leu Thr Cys Gly Arg Cys Leu Arg Ala Trp His Phe Met Gly
    530                 535                 540
Cys Gly Trp Cys Gly Asn Met Cys Gly Gln Gln Lys Glu Cys Pro Gly
545                 550                 555                 560
Ser Trp Gln Gln Asp His Cys Pro Pro Lys Leu Thr Glu Phe His Pro
                565                 570                 575
His Ser Gly Pro Leu Arg Gly Ser Thr Arg Leu Thr Leu Cys Gly Ser
            580                 585                 590
Asn Phe Tyr Leu His Pro Ser Gly Leu Val Pro Glu Gly Thr His Gln
        595                 600                 605
Val Thr Val Gly Gln Ser Pro Cys Arg Pro Leu Pro Lys Asp Ser Ser
    610                 615                 620
Lys Leu Arg Pro Val Pro Arg Lys Asp Phe Val Glu Glu Phe Glu Cys
625                 630                 635                 640
Glu Leu Glu Pro Leu Gly Thr Gln Ala Val Gly Pro Thr Asn Val Ser
                645                 650                 655
Leu Thr Val Thr Asn Met Pro Pro Gly Lys His Phe Arg Val Asp Gly
            660                 665                 670
Thr Ser Val Leu Arg Gly Phe Ser Phe Met Glu Pro Val Leu Ile Ala
        675                 680                 685
Val Gln Pro Leu Phe Gly Pro Arg Ala Gly Gly Thr Cys Leu Thr Leu
    690                 695                 700
Glu Gly Gln Ser Leu Ser Val Gly Thr Ser Arg Ala Val Leu Val Asn
705                 710                 715                 720
Gly Thr Glu Cys Leu Leu Ala Arg Val Ser Glu Gly Gln Leu Leu Cys
                725                 730                 735
Ala Thr Pro Pro Gly Ala Thr Val Ala Ser Val Pro Leu Ser Leu Gln
            740                 745                 750
Val Gly Gly Ala Gln Val Pro Gly Ser Trp Thr Phe Gln Tyr Arg Glu
        755                 760                 765
Asp Pro Val Val Leu Ser Ile Ser Pro Asn Cys Gly Tyr Ile Asn Ser
    770                 775                 780
His Ile Thr Ile Cys Gly Gln His Leu Thr Ser Ala Trp His Leu Val
785                 790                 795                 800
Leu Ser Phe His Asp Gly Leu Arg Ala Val Glu Ser Arg Cys Glu Arg
                805                 810                 815
Gln Leu Pro Glu Gln Gln Leu Cys Arg Leu Pro Glu Tyr Val Val Arg
            820                 825                 830
Asp Pro Gln Gly Trp Val Ala Gly Asn Leu Ser Ala Arg Gly Asp Gly
        835                 840                 845
Ala Ala Gly Phe Thr Leu Pro Gly Phe Arg Phe Leu Pro Pro His His
    850                 855                 860
Pro Pro Ser Ala Asn Leu Val Pro Leu Lys Pro Glu Glu His Ala Ile
865                 870                 875                 880
Lys Phe Glu Tyr Ile Gly Leu Gly Ala Val Ala Asp Cys Val Gly Ile
                885                 890                 895
Asn Val Thr Val Gly Gly Glu Ser Cys Gln His Glu Phe Arg Gly Asp
            900                 905                 910
Met Val Val Cys Pro Leu Pro Pro Ser Leu Gln Leu Gly Gln Asp Gly
        915                 920                 925
Ala Pro Leu Gln Val Cys Val Asp Ala Leu Pro Ala Ile Asp Gly Leu
    930                 935                 940
Asp Ser Thr Thr Cys Val His Gly Ala Ser Phe Ser Asp Ser Glu Asp
945                 950                 955                 960
```

FIG. 2B-3  SEQ ID NO: 4 cont.

```
Glu Ser Cys Val Pro Leu Leu Arg Lys Glu Ser Ile Gln Leu Arg Asp
            965             970             975
Leu Asp Ser Ala Leu Leu Ala Glu Val Lys Asp Val Leu Ile Pro His
            980             985             990
Glu Arg Val Val Thr His Ser Asp Arg Val Ile Gly Lys Gly His Phe
            995             1000            1005
Gly Val Val Tyr His Gly Glu Tyr Ile Asp Gln Ala Gln Asn Arg Ile
            1010            1015            1020
Gln Cys Ala Ile Lys Ser Leu Ser Arg Ile Thr Glu Met Gln Gln Val
1025                1030            1035                1040
Glu Ala Phe Leu Arg Glu Gly Leu Leu Met Arg Gly Leu Asn His Pro
                1045            1050            1055
Asn Val Leu Ala Leu Ile Gly Ile Met Leu Pro Pro Glu Gly Leu Pro
            1060            1065            1070
His Val Leu Leu Pro Tyr Met Cys His Gly Asp Leu Leu Gln Phe Ile
            1075            1080            1085
Arg Ser Pro Gln Arg Asn Pro Thr Val Lys Asp Leu Ile Ser Phe Gly
            1090            1095            1100
Leu Gln Val Ala Arg Gly Met Glu Tyr Leu Ala Glu Gln Lys Phe Val
1105                1110            1115                1120
His Arg Asp Leu Ala Ala Arg Asn Cys Met Leu Asp Glu Ser Phe Thr
                1125            1130            1135
Val Lys Val Ala Asp Phe Gly Leu Ala Arg Asp Ile Leu Asp Arg Glu
            1140            1145            1150
Tyr Tyr Ser Val Gln Gln His Arg His Ala Arg Leu Pro Val Lys Trp
            1155            1160            1165
Met Ala Leu Glu Ser Leu Gln Thr Tyr Arg Phe Thr Thr Lys Ser Asp
            1170            1175            1180
Val Val Pro Ser Asp Ala Ala Met Leu Gly Gly Arg Pro Ser Ser Ala
1185                1190            1195                1200
Thr His Leu Gln Ser Thr Ser Gly Gly Gly Gly Ala Asp Ser Val Cys
                1205            1210            1215
Thr Ala Trp Gly Pro Leu Cys Ala Ala Ala Ser Asn Leu His Glu Leu
            1220            1225            1230
Glu Leu Thr Pro Arg Leu Pro Leu Gly His Ala Arg Pro Glu Gln Trp
            1235            1240            1245
Pro Ser Thr Leu Phe Leu Pro Phe Asn Phe Gln Arg Gln
    1250            1255            1260
```

FIG. 2C-1  Coding Sequence (SEQ ID NO: 3 & 4)

| | | | | | | | | | | | | | | | | |
|---|---|---|---|---|---|---|---|---|---|---|---|---|---|---|---|---|
| atg | gag | ctc | ctc | ccg | ccg | ctg | cct | cag | tcc | ttc | ctg | ttg | ctg | ctg | ctg | 48 |
| Met | Glu | Leu | Leu | Pro | Pro | Leu | Pro | Gln | Ser | Phe | Leu | Leu | Leu | Leu | Leu | |
| | | | | 5 | | | | | 10 | | | | | 15 | | |
| ttg | cct | gcc | aag | ccc | gcg | gcg | ggc | gag | gac | tgg | cag | tgc | ccg | cgc | acc | 96 |
| Leu | Pro | Ala | Lys | Pro | Ala | Ala | Gly | Glu | Asp | Trp | Gln | Cys | Pro | Arg | Thr | |
| | | | 20 | | | | | 25 | | | | | 30 | | | |
| ccc | tac | gcg | gcc | tct | cgc | gac | ttt | gac | gtg | aag | tac | gtg | gtg | ccc | agc | 144 |
| Pro | Tyr | Ala | Ala | Ser | Arg | Asp | Phe | Asp | Val | Lys | Tyr | Val | Val | Pro | Ser | |
| | | 35 | | | | | 40 | | | | | 45 | | | | |
| ttc | tcc | gcc | gga | ggc | ctg | gta | cag | gcc | atg | gtg | acc | tac | gag | ggc | gac | 192 |
| Phe | Ser | Ala | Gly | Gly | Leu | Val | Gln | Ala | Met | Val | Thr | Tyr | Glu | Gly | Asp | |
| | 50 | | | | 55 | | | | | 60 | | | | | | |
| aga | aat | gag | agt | gct | gtg | ttt | gta | gcc | ata | cgc | aat | cgc | ctg | cat | gtg | 240 |
| Arg | Asn | Glu | Ser | Ala | Val | Phe | Val | Ala | Ile | Arg | Asn | Arg | Leu | His | Val | |
| 65 | | | | | 70 | | | | | 75 | | | | | 80 | |
| ctt | ggg | cct | gac | ctg | aag | tct | gtc | cag | agc | ctg | gcc | acg | ggc | cct | gct | 288 |
| Leu | Gly | Pro | Asp | Leu | Lys | Ser | Val | Gln | Ser | Leu | Ala | Thr | Gly | Pro | Ala | |
| | | | | 85 | | | | | 90 | | | | | 95 | | |
| gga | gac | cct | ggc | tgc | cag | acg | tgt | gca | gcc | tgt | ggc | cca | gga | ccc | cac | 336 |
| Gly | Asp | Pro | Gly | Cys | Gln | Thr | Cys | Ala | Ala | Cys | Gly | Pro | Gly | Pro | His | |
| | | | 100 | | | | | 105 | | | | | 110 | | | |
| ggc | cct | ccc | ggt | gac | aca | gac | aca | aag | gtg | ctg | gtg | ctg | gat | ccc | gcg | 384 |
| Gly | Pro | Pro | Gly | Asp | Thr | Asp | Thr | Lys | Val | Leu | Val | Leu | Asp | Pro | Ala | |
| | | 115 | | | | | 120 | | | | | 125 | | | | |
| ctg | cct | gcg | ctg | gtc | agt | tgt | ggc | tcc | agc | ctg | cag | ggc | cgc | tgc | ttc | 432 |
| Leu | Pro | Ala | Leu | Val | Ser | Cys | Gly | Ser | Ser | Leu | Gln | Gly | Arg | Cys | Phe | |
| | 130 | | | | 135 | | | | | 140 | | | | | | |
| ctg | cat | gac | cta | gag | ccc | caa | ggg | aca | gcc | gtg | cat | ctg | gca | gcg | cca | 480 |
| Leu | His | Asp | Leu | Glu | Pro | Gln | Gly | Thr | Ala | Val | His | Leu | Ala | Ala | Pro | |
| 145 | | | | | 150 | | | | | 155 | | | | | 160 | |
| gcc | tgc | ctc | ttc | tca | gcc | cac | cat | aac | cgg | ccc | gat | gac | tgc | ccc | gac | 528 |
| Ala | Cys | Leu | Phe | Ser | Ala | His | His | Asn | Arg | Pro | Asp | Asp | Cys | Pro | Asp | |
| | | | | 165 | | | | | 170 | | | | | 175 | | |
| tgt | gtg | gcc | agc | cca | ttg | ggc | acc | cgt | gta | act | gtg | gtt | gag | caa | ggc | 576 |
| Cys | Val | Ala | Ser | Pro | Leu | Gly | Thr | Arg | Val | Thr | Val | Val | Glu | Gln | Gly | |
| | | | 180 | | | | | 185 | | | | | 190 | | | |
| cag | gcc | tcc | tat | ttc | tac | gtg | gca | tcc | tca | ctg | gac | gca | gcc | gtg | gct | 624 |
| Gln | Ala | Ser | Tyr | Phe | Tyr | Val | Ala | Ser | Ser | Leu | Asp | Ala | Ala | Val | Ala | |
| | | 195 | | | | | 200 | | | | | 205 | | | | |
| ggc | agc | ttc | agc | cca | cgc | tca | gtg | tct | atc | agg | cgt | ctc | aag | gct | gac | 672 |
| Gly | Ser | Phe | Ser | Pro | Arg | Ser | Val | Ser | Ile | Arg | Arg | Leu | Lys | Ala | Asp | |
| | 210 | | | | 215 | | | | | 220 | | | | | | |
| gcc | tcg | gga | ttc | gca | ccg | ggc | ttt | gtg | gcg | ttg | tca | gtg | ctg | ccc | aag | 720 |
| Ala | Ser | Gly | Phe | Ala | Pro | Gly | Phe | Val | Ala | Leu | Ser | Val | Leu | Pro | Lys | |
| 225 | | | | | 230 | | | | | 235 | | | | | 240 | |
| cat | ctt | gtc | tcc | tac | agt | att | gaa | tac | gtg | cac | agc | ttc | cac | acg | gga | 768 |
| His | Leu | Val | Ser | Tyr | Ser | Ile | Glu | Tyr | Val | His | Ser | Phe | His | Thr | Gly | |
| | | | | 245 | | | | | 250 | | | | | 255 | | |
| gcc | ttc | gta | tac | ttc | act | gta | cag | ccg | gcc | agc | gtg | aca | gat | gat | 816 | |
| Ala | Phe | Val | Tyr | Phe | Leu | Thr | Val | Gln | Pro | Ala | Ser | Val | Thr | Asp | Asp | |
| | | | 260 | | | | | 265 | | | | | 270 | | | |
| cct | agt | gcc | ctg | cac | aca | cgc | ctg | gca | cgg | ctt | agc | gcc | act | gag | cca | 864 |
| Pro | Ser | Ala | Leu | His | Thr | Arg | Leu | Ala | Arg | Leu | Ser | Ala | Thr | Glu | Pro | |
| | | 275 | | | | | 280 | | | | | 285 | | | | |
| gag | ttg | ggt | gac | tat | cgg | gag | ctg | gtc | ctc | gac | tgc | aga | ttt | gct | cca | 912 |
| Glu | Leu | Gly | Asp | Tyr | Arg | Glu | Leu | Val | Leu | Asp | Cys | Arg | Phe | Ala | Pro | |
| | 290 | | | | 295 | | | | | 300 | | | | | | |
| aaa | cgc | agg | cgc | cgg | ggg | gcc | cca | gaa | ggc | gga | cag | ccc | tac | cct | gtg | 960 |
| Lys | Arg | Arg | Arg | Arg | Gly | Ala | Pro | Glu | Gly | Gly | Gln | Pro | Tyr | Pro | Val | |
| 305 | | | | | 310 | | | | | 315 | | | | | 320 | |

FIG. 2C-2                 Coding Sequence (SEQ ID NO: 3 & 4) cont.

```
ctg  cag  gtg  gcc  cac  tcc  gct  cca  gtg  ggt  gcc  caa  ctt  gcc  act  gag  1008
Leu  Gln  Val  Ala  His  Ser  Ala  Pro  Val  Gly  Ala  Gln  Leu  Ala  Thr  Glu
               325                          330                         335
ctg  agc  atc  gcc  gag  ggc  cag  gaa  gta  cta  ttt  ggg  gtc  ttt  gtg  act  1056
Leu  Ser  Ile  Ala  Glu  Gly  Gln  Glu  Val  Leu  Phe  Gly  Val  Phe  Val  Thr
               340                          345                         350
ggc  aag  gat  ggt  ggt  cct  ggc  gtg  ggc  ccc  aac  tct  gtc  gtc  tgt  gcc  1104
Gly  Lys  Asp  Gly  Gly  Pro  Gly  Val  Gly  Pro  Asn  Ser  Val  Val  Cys  Ala
               355                          360                         365
ttc  ccc  att  gac  ctg  ctg  gac  aca  cta  att  gat  gag  ggt  gtg  gag  cgc  1152
Phe  Pro  Ile  Asp  Leu  Leu  Asp  Thr  Leu  Ile  Asp  Glu  Gly  Val  Glu  Arg
     370                         375                         380
tgt  tgt  gaa  tcc  cca  gtc  cat  cca  ggc  ctc  cgg  cga  ggc  ctc  gac  ttc  1200
Cys  Cys  Glu  Ser  Pro  Val  His  Pro  Gly  Leu  Arg  Arg  Gly  Leu  Asp  Phe
385                         390                         395                 400
ttc  cag  tcg  ccc  agt  ttt  tgc  ccc  aac  ccg  cct  ggc  ctg  gaa  gcc  ctc  1248
Phe  Gln  Ser  Pro  Ser  Phe  Cys  Pro  Asn  Pro  Pro  Gly  Leu  Glu  Ala  Leu
                    405                         410                     415
agc  ccc  aac  acc  agc  tgc  cgc  cac  ttc  cct  ctg  ctg  gtc  agt  agc  agc  1296
Ser  Pro  Asn  Thr  Ser  Cys  Arg  His  Phe  Pro  Leu  Leu  Val  Ser  Ser  Ser
               420                         425                     430
ttc  tca  cgt  gtg  gac  cta  ttc  aat  ggg  ctg  ttg  gga  cca  gta  cag  gtc  1344
Phe  Ser  Arg  Val  Asp  Leu  Phe  Asn  Gly  Leu  Leu  Gly  Pro  Val  Gln  Val
          435                          440                     445
act  gca  ttg  tat  gtg  aca  cgc  ctt  gac  aac  gtc  aca  gtg  gca  cac  atg  1392
Thr  Ala  Leu  Tyr  Val  Thr  Arg  Leu  Asp  Asn  Val  Thr  Val  Ala  His  Met
     450                         455                     460
ggc  aca  atg  gat  ggg  cgt  atc  ctg  cag  gtg  gag  ctg  gtc  agg  tca  cta  1440
Gly  Thr  Met  Asp  Gly  Arg  Ile  Leu  Gln  Val  Glu  Leu  Val  Arg  Ser  Leu
465                         470                     475                     480
aac  tac  ttg  ctg  tat  gtg  tcc  aac  ttc  tca  ctg  ggt  gac  agt  ggg  cag  1488
Asn  Tyr  Leu  Leu  Tyr  Val  Ser  Asn  Phe  Ser  Leu  Gly  Asp  Ser  Gly  Gln
                    485                     490                     495
ccc  gtg  cag  cgg  gat  gtc  agt  cgt  ctt  ggg  gac  cac  cta  ctc  ttt  gcc  1536
Pro  Val  Gln  Arg  Asp  Val  Ser  Arg  Leu  Gly  Asp  His  Leu  Leu  Phe  Ala
               500                     505                     510
tct  ggg  gac  cag  gtt  ttc  cag  gta  cct  atc  cga  ggc  cct  ggc  tgc  cgc  1584
Ser  Gly  Asp  Gln  Val  Phe  Gln  Val  Pro  Ile  Arg  Gly  Pro  Gly  Cys  Arg
          515                     520                     525
cac  ttc  ctg  acc  tgt  ggg  cgt  tgc  cta  agg  gca  tgg  cat  ttc  atg  ggc  1632
His  Phe  Leu  Thr  Cys  Gly  Arg  Cys  Leu  Arg  Ala  Trp  His  Phe  Met  Gly
     530                         535                     540
tgt  ggc  tgg  tgt  ggg  aac  atg  tgc  ggc  cag  cag  aag  gag  tgt  cct  ggc  1680
Cys  Gly  Trp  Cys  Gly  Asn  Met  Cys  Gly  Gln  Gln  Lys  Glu  Cys  Pro  Gly
545                         550                     555                     560
tcc  tgg  caa  cag  gac  cac  tgc  cca  cct  aag  ctt  act  gag  ttc  cac  ccc  1728
Ser  Trp  Gln  Gln  Asp  His  Cys  Pro  Pro  Lys  Leu  Thr  Glu  Phe  His  Pro
                    565                     570                     575
cac  agt  gga  cct  cta  agg  ggc  agt  aca  agg  ctg  acc  ctg  tgt  ggc  tcc  1776
His  Ser  Gly  Pro  Leu  Arg  Gly  Ser  Thr  Arg  Leu  Thr  Leu  Cys  Gly  Ser
               580                     585                     590
aac  ttc  tac  ctt  cac  cct  tct  ggt  ctg  gtg  cct  gag  gga  acc  cat  cag  1824
Asn  Phe  Tyr  Leu  His  Pro  Ser  Gly  Leu  Val  Pro  Glu  Gly  Thr  His  Gln
          595                     600                     605
gtc  act  gtg  ggc  caa  agt  ccc  tgc  cgg  cca  ctg  ccc  aag  gac  agc  tca  1872
Val  Thr  Val  Gly  Gln  Ser  Pro  Cys  Arg  Pro  Leu  Pro  Lys  Asp  Ser  Ser
     610                         615                     620
aaa  ctc  aga  cca  gtg  ccc  cgg  aaa  gac  ttt  gta  gag  gag  ttt  gag  tgt  1920
Lys  Leu  Arg  Pro  Val  Pro  Arg  Lys  Asp  Phe  Val  Glu  Glu  Phe  Glu  Cys
625                         630                     635                     640
```

FIG. 2C-3  Coding Sequence (SEQ ID NO: 3 & 4) cont.

```
gaa ctg gag ccc ttg ggc acc cag gca gtg ggg cct acc aac gtc agc 1968
Glu Leu Glu Pro Leu Gly Thr Gln Ala Val Gly Pro Thr Asn Val Ser
            645                 650                 655
ctc acc gtg act aac atg cca ccg ggc aag cac ttc cgg gta gac ggc 2016
Leu Thr Val Thr Asn Met Pro Pro Gly Lys His Phe Arg Val Asp Gly
        660                 665                 670
acc tcc gtg ctg aga ggc ttc tct ttc atg gag cca gtg ctg ata gca 2064
Thr Ser Val Leu Arg Gly Phe Ser Phe Met Glu Pro Val Leu Ile Ala
            675                 680                 685
gtg caa ccc ctc ttt ggc cca cgg gca gga ggc acc tgt ctc act ctt 2112
Val Gln Pro Leu Phe Gly Pro Arg Ala Gly Gly Thr Cys Leu Thr Leu
        690                 695                 700
gaa ggc cag agt ctg tct gta ggc acc agc cgg gct gtg ctg gtc aat 2160
Glu Gly Gln Ser Leu Ser Val Gly Thr Ser Arg Ala Val Leu Val Asn
705                 710                 715                 720
ggg act gag tgt ctg cta gca cgg gtc agt gag ggg cag ctt tta tgt 2208
Gly Thr Glu Cys Leu Leu Ala Arg Val Ser Glu Gly Gln Leu Leu Cys
            725                 730                 735
gcc aca ccc cct ggg gcc acg gtg gcc agt gtc ccc ctt agc ctg cag 2256
Ala Thr Pro Pro Gly Ala Thr Val Ala Ser Val Pro Leu Ser Leu Gln
        740                 745                 750
gtg ggg ggt gcc cag gta cct ggt tcc tgg acc ttc cag tac aga gaa 2304
Val Gly Gly Ala Gln Val Pro Gly Ser Trp Thr Phe Gln Tyr Arg Glu
            755                 760                 765
gac cct gtc gtg cta agc atc agc ccc aac tgt ggc tac atc aac tcc 2352
Asp Pro Val Val Leu Ser Ile Ser Pro Asn Cys Gly Tyr Ile Asn Ser
    770                 775                 780
cac atc acc atc tgt ggc cag cat cta act tca gca tgg cac tta gtg 2400
His Ile Thr Ile Cys Gly Gln His Leu Thr Ser Ala Trp His Leu Val
785                 790                 795                 800
ctg tca ttc cat gac ggg ctt agg gca gtg gaa agc agg tgt gag agg 2448
Leu Ser Phe His Asp Gly Leu Arg Ala Val Glu Ser Arg Cys Glu Arg
            805                 810                 815
cag ctt cca gag cag cag ctg tgc cgc ctt cct gaa tat gtg gtc cga 2496
Gln Leu Pro Glu Gln Gln Leu Cys Arg Leu Pro Glu Tyr Val Val Arg
        820                 825                 830
gac ccc cag gga tgg gtg gca ggg aat ctg agt gcc cga ggg gat gga 2544
Asp Pro Gln Gly Trp Val Ala Gly Asn Leu Ser Ala Arg Gly Asp Gly
            835                 840                 845
gct gct ggc ttt aca ctg cct ggc ttt cgc ttc cta ccc cca ccc cat 2592
Ala Ala Gly Phe Thr Leu Pro Gly Phe Arg Phe Leu Pro Pro Pro His
    850                 855                 860
cca ccc agt gcc aac cta gtt cca ctg aag cct gag gag cat gcc att 2640
Pro Pro Ser Ala Asn Leu Val Pro Leu Lys Pro Glu Glu His Ala Ile
865                 870                 875                 880
aag ttt gag tat att ggg ctg ggc gct gtg gct gac tgt gtg ggt atc 2688
Lys Phe Glu Tyr Ile Gly Leu Gly Ala Val Ala Asp Cys Val Gly Ile
            885                 890                 895
aac gtg acc gtg ggt ggt gag agc tgc cag cac gag ttc cgg ggg gac 2736
Asn Val Thr Val Gly Gly Glu Ser Cys Gln His Glu Phe Arg Gly Asp
        900                 905                 910
atg gtt gtc tgc ccc ctg ccc cca tcc ctg cag ctt ggc cag gat ggt 2784
Met Val Val Cys Pro Leu Pro Pro Ser Leu Gln Leu Gly Gln Asp Gly
            915                 920                 925
gcc cca ttg cag gtc tgc gta gat gca ctc cct gcc att gat ggt ctg 2832
Ala Pro Leu Gln Val Cys Val Asp Ala Leu Pro Ala Ile Asp Gly Leu
    930                 935                 940
gat tcc acc act tgt gtc cat gga gca tcc ttc tcc gat agt gaa gat 2880
Asp Ser Thr Thr Cys Val His Gly Ala Ser Phe Ser Asp Ser Glu Asp
945                 950                 955                 960
```

FIG. 2C-4  Coding Sequence (SEQ ID NO: 3 & 4) cont.

```
gaa tcc tgt gtg cca ctg ctg cgg aaa gag tcc atc cag cta agg gac  2928
Glu Ser Cys Val Pro Leu Leu Arg Lys Glu Ser Ile Gln Leu Arg Asp
            965                 970                 975
ctg gac tct gcg ctc ttg gct gag gtc aag gat gtg ctg att ccc cat  2976
Leu Asp Ser Ala Leu Leu Ala Glu Val Lys Asp Val Leu Ile Pro His
            980                 985                 990
gag cgg gtg gtc acc cac agt gac cga gtc att ggc aaa ggc cac ttt  3024
Glu Arg Val Val Thr His Ser Asp Arg Val Ile Gly Lys Gly His Phe
            995                 1000                1005
gga gtt gtc tac cac gga gaa tac ata gac cag gcc cag aat cga atc  3072
Gly Val Val Tyr His Gly Glu Tyr Ile Asp Gln Ala Gln Asn Arg Ile
    1010                1015                1020
caa tgt gcc atc aag tca cta agt cgc atc aca gag atg cag cag gtg  3120
Gln Cys Ala Ile Lys Ser Leu Ser Arg Ile Thr Glu Met Gln Gln Val
1025                1030                1035                1040
gag gcc ttc ctg cga gag ggg ctg ctc atg cgt ggc ctg aac cac ccg  3168
Glu Ala Phe Leu Arg Glu Gly Leu Leu Met Arg Gly Leu Asn His Pro
                1045                1050                1055
aat gtg ctg gct ctc att ggt atc atg ttg cca cct gag ggc ctg ccc  3216
Asn Val Leu Ala Leu Ile Gly Ile Met Leu Pro Pro Glu Gly Leu Pro
            1060                1065                1070
cat gtg ctg ctg ccc tat atg tgc cac ggt gac ctc ctc cag ttc atc  3264
His Val Leu Leu Pro Tyr Met Cys His Gly Asp Leu Leu Gln Phe Ile
            1075                1080                1085
cgc tca cct cag cgg aac ccc acc gtg aag gac ctc atc agc ttt ggc  3312
Arg Ser Pro Gln Arg Asn Pro Thr Val Lys Asp Leu Ile Ser Phe Gly
        1090                1095                1100
ctg cag gta gcc cgc ggc atg gag tac ctg gca gag cag aag ttt gtg  3360
Leu Gln Val Ala Arg Gly Met Glu Tyr Leu Ala Glu Gln Lys Phe Val
1105                1110                1115                1120
cac agg gac ctg gct gcg cgg aac tgc atg ctg gac gag tca ttc aca  3408
His Arg Asp Leu Ala Ala Arg Asn Cys Met Leu Asp Glu Ser Phe Thr
                1125                1130                1135
gtc aag gtg gct gac ttt ggt ttg gcc cgc gac atc ctg gac agg gag  3456
Val Lys Val Ala Asp Phe Gly Leu Ala Arg Asp Ile Leu Asp Arg Glu
            1140                1145                1150
tac tat agt gtt caa cag cat cgc cac gct cgc cta cct gtg aag tgg  3504
Tyr Tyr Ser Val Gln Gln His Arg His Ala Arg Leu Pro Val Lys Trp
            1155                1160                1165
atg gcg ctg gag agc ctg cag acc tat aga ttt acc acc aag tct gat  3552
Met Ala Leu Glu Ser Leu Gln Thr Tyr Arg Phe Thr Thr Lys Ser Asp
    1170                1175                1180
gtg gta cca agt gat gca gca atg ctg gga ggc aga ccc agc agt gcg  3600
Val Val Pro Ser Asp Ala Ala Met Leu Gly Gly Arg Pro Ser Ser Ala
1185                1190                1195                1200
acc cac ctt cag agt act agt ggg gga ggt gga gca gat agt gtc tgc  3648
Thr His Leu Gln Ser Thr Ser Gly Gly Gly Gly Ala Asp Ser Val Cys
                1205                1210                1215
act gct tgg gga cca tta tgt gca gct gcc agc aac cta cat gaa ctt  3696
Thr Ala Trp Gly Pro Leu Cys Ala Ala Ala Ser Asn Leu His Glu Leu
            1220                1225                1230
gag cta acc cca agg ctg cct ctg ggc cat gcc agg cca gag cag tgg  3744
Glu Leu Thr Pro Arg Leu Pro Leu Gly His Ala Arg Pro Glu Gln Trp
        1235                1240                1245
ccc tcc acc ttg ttc ctg ccc ttt aac ttt cag agg caa               3783
Pro Ser Thr Leu Phe Leu Pro Phe Asn Phe Gln Arg Gln
    1250                1255                1260
```

FIG. 3A-1          SEQ ID NO: 5

```
ggatcctcta gggtcccagc tcgcctcgat ggagctcctc ccgccgctgc ctcagtcctt    60
cctgttgctg ctgctgttgc ctgccaagcc cgcggcgggc gaggactggc agtgcccgcg   120
caccccctac gcggcctctc gcgactttga cgtgaagtac gtggtgccca gcttctccgc   180
cggaggcctg gtacaggcca tggtgaccta cgagggcgac agaaatgaga gtgctgtgtt   240
tgtagccata cgcaatcgcc tgcatgtgct gggcctgac ctgaagtctg tccagagcct   300
ggccacgggc cctgctggag accctggctg ccagacgtgt gcagcctgtg cccaggacc   360
ccacggccct cccggtgaca cagacacaaa ggtgctggtg ctggatcccg cgctgcctgc   420
gctggtcagt tgtggctcca gcctgcaggg ccgctgcttc ctgcatgacc tagagcccca   480
agggacagcc gtgcatctgg cagcgccagc ctgcctcttc tcagcccacc ataaccggcc   540
cgatgactgc cccgactgtg tggccagccc attgggcacc cgtgtaactg tggttgagca   600
aggccaggcc tcctatttct acgtggcatc ctcactggac gcagccgtgg ctggcagctt   660
cagcccacgc tcagtgtcta tcaggcgtct caaggctgac gcctcgggat tcgcaccggg   720
ctttgtggcg ttgtcagtgc tgcccaagca tcttgtctcc tacagtattg aatacgtgca   780
cagcttccac acgggagcct tcgtatactt cctgactgta cagccggcca gcgtgacaga   840
tgatcctagt gccctgcaca cacgcctggc acggcttagc gccactgagc cagagttggg   900
tgactatcgg gagctggtcc tcgactgcag atttgctcca aaacgcaggc gccgggggc   960
cccagaaggc ggacagccct accctgtgct gcaggtggcc cactccgctc cagtgggtgc  1020
ccaacttgcc actgagctga gcatcgccga gggccaggaa gtactatttg gggtctttgt  1080
gactggcaag gatggtggtc ctggcgtggg ccccaactct gtcgtctgtg ccttcccat  1140
tgacctgctg gacacactaa ttgatgaggg tgtggagcgc tgttgtgaat ccccagtcca  1200
tccaggcctc cggcgaggcc tcgacttctt ccagtcgccc agtttttgcc ccaacccgcc  1260
tggcctggaa gccctcagcc ccaacaccag ctgccgccac ttccctctgc tggtcagtag  1320
cagcttctca cgtgtggacc tattcaatgg gctgttggga ccagtacagg tcactgcatt  1380
gtatgtgaca cgccttgaca acgtcacagt ggcacacatg ggcacaatgg atgggcgtat  1440
cctgcaggtg gagctggtca ggtcactaaa ctacttgctg tatgtgtcca acttctcact  1500
gggtgacagt gggcagcccg tgcagcggga tgtcagtcgt cttggggacc acctactctt  1560
tgcctctggg gaccaggttt ccaggtacc tatccgaggc cctggctgcc gccacttcct  1620
gacctgtggg cgttgcctaa gggcatggca tttcatgggc tgtggctggt gtgggaacat  1680
gtgcggccag cagaaggagt gtcctggctc ctggcaacag gaccactgcc cacctaagct  1740
tactgagttc cacccccaca gtggacctct aaggggcagt acaaggctga ccctgtgtgg  1800
ctccaacttc taccttcacc cttctggtct ggtgcctgag ggaacccatc aggtcactgt  1860
gggccaaagt ccctgccggc cactgcccaa ggacagctca aaactcagac cagtgccccg  1920
gaaagacttt gtagaggagt ttgagtgtga actggagccc ttgggcaccc aggcagtggg  1980
gcctaccaac gtcagcctca ccgtgactaa catgccaccg ggcaagcact tccgggtaga  2040
cggcacctcc gtgctgagag gcttctcttt catggagcca gtgctgatag cagtgcaacc  2100
cctctttggc ccacgggcag gaggcacctg tctcactctt gaaggccaga gtctgtctgt  2160
aggcaccagc cgggctgtgc tggtcaatgg gactgagtgt ctgctagcac gggtcagtga  2220
ggggcagctt ttatgtgcca cacccctgg ggccacggtg gccagtgtcc cccttagcct  2280
```

FIG. 3A-2  SEQ ID NO: 5 cont.

| | | | | | | |
|---|---|---|---|---|---|---|
| gcaggtgggg | ggtgcccagg | tacctggttc | ctggaccttc | cagtacagag | aagaccctgt | 2340 |
| cgtgctaagc | atcagccca | actgtggcta | catcaactcc | cacatcacca | tctgtggcca | 2400 |
| gcatctaact | tcagcatggc | acttagtgct | gtcattccat | gacgggctta | gggcagtgga | 2460 |
| aagcaggtgt | gagaggcagc | ttccagagca | gcagctgtgc | cgccttcctg | aatatgtggt | 2520 |
| ccgagacccc | cagggatggg | tggcagggaa | tctgagtgcc | cgaggggatg | gagctgctgg | 2580 |
| ctttacactg | cctggctttc | gcttcctacc | cccacccat | ccacccagtg | ccaacctagt | 2640 |
| tccactgaag | cctgaggagc | atgccattaa | gtttgagctt | ggccaggatg | gtgccccatt | 2700 |
| gcaggtctgc | gtagatgcac | tccctgccat | tgatggtctg | gattccacca | cttgtgtcca | 2760 |
| tggagcatcc | ttctccgata | gtgaagatga | atcctgtgtg | ccactgctgc | ggaaagagtc | 2820 |
| catccagcta | agggacctgg | actctgcgct | cttggctgag | gtcaaggatg | tgctgattcc | 2880 |
| ccatgagcgg | gtggtcaccc | acagtgaccg | agtcattggc | aaaggccact | ttggagttgt | 2940 |
| ctaccacgga | gaatacatag | accaggccca | gaatcgaatc | caatgtgcca | tcaagtcact | 3000 |
| aagtcgcatc | acagagatgc | agcaggtgga | ggccttcctg | cgagagggc | tgctcatgcg | 3060 |
| tggcctgaac | cacccgaatg | tgctggctct | cattggtatc | atgttgccac | ctgagggcct | 3120 |
| gccccatgtg | ctgctgccct | atatgtgcca | cggtgacctg | ctccagttca | tccgctcacc | 3180 |
| tcagcggaac | cccaccgtga | aggacctcat | cagctttggc | ctgcaggtag | cccgcggcat | 3240 |
| ggagtacctg | gcagagcaga | agtttgtgca | cagggacctg | gctgcgcgga | actgcatgct | 3300 |
| ggacgagtca | ttcacagtca | aggtggctga | ctttggtttg | gcccgcgaca | tcctggacag | 3360 |
| ggagtactat | agtgttcaac | agcatcgcca | cgctcgccta | cctgtgaagt | ggatggcgct | 3420 |
| ggagagcctg | cagacctata | gatttaccac | caagtctgat | gtggtaccaa | gtgatgcagc | 3480 |
| aatgctggga | ggcagaccca | gcagtgcgac | ccaccttcag | agtactagtg | ggggaggtgg | 3540 |
| agcagatagt | gtctgcactg | cttggggacc | attatgtgca | gctgccagca | acctacatga | 3600 |
| acttgagcta | accccaaggc | tgcctctggg | ccatgccagg | ccagagcagt | ggccctccac | 3660 |
| cttgttcctg | cccttaact | ttcagaggca | ataggtaaat | gggcccatta | ggtccctcac | 3720 |
| tccacagagt | gagccagtga | gggcagtcct | gcaacatgta | tttatggagt | gcctgctgtg | 3780 |
| gaccctgtct | tctgggcaca | gtggactcag | cagtgaccac | accaacactg | acccttgaac | 3840 |
| caataaagga | acaaatgact | attaaagcac | aaaaaaaaaa | | | 3880 |

FIG. 3B-1             SEQ ID NO: 6

| | | | | | | | | | | | | | | |
|---|---|---|---|---|---|---|---|---|---|---|---|---|---|---|
| Met | Glu | Leu | Leu | Pro 5 | Pro | Leu | Pro | Gln | Ser 10 | Phe | Leu | Leu | Leu 15 | Leu |
| Leu | Pro | Ala | Lys 20 | Pro | Ala | Ala | Gly | Glu 25 | Asp | Trp | Gln | Cys | Pro 30 | Arg | Thr |
| Pro | Tyr | Ala 35 | Ala | Ser | Arg | Asp | Phe 40 | Asp | Val | Lys | Tyr | Val 45 | Val | Pro | Ser |
| Phe | Ser 50 | Ala | Gly | Gly | Leu | Val 55 | Gln | Ala | Met | Val | Thr 60 | Tyr | Glu | Gly | Asp |
| Arg 65 | Asn | Glu | Ser | Ala | Val 70 | Phe | Val | Ala | Ile | Arg 75 | Asn | Arg | Leu | His | Val 80 |
| Leu | Gly | Pro | Asp | Leu 85 | Lys | Ser | Val | Gln | Ser 90 | Leu | Ala | Thr | Gly | Pro 95 | Ala |
| Gly | Asp | Pro | Gly 100 | Cys | Gln | Thr | Cys | Ala 105 | Ala | Cys | Gly | Pro | Gly 110 | Pro | His |
| Gly | Pro | Pro 115 | Gly | Asp | Thr | Asp | Thr 120 | Lys | Val | Leu | Val | Leu 125 | Asp | Pro | Ala |
| Leu | Pro 130 | Ala | Leu | Val | Ser | Cys 135 | Gly | Ser | Ser | Leu | Gln 140 | Gly | Arg | Cys | Phe |
| Leu 145 | His | Asp | Leu | Glu | Pro 150 | Gln | Gly | Thr | Ala | Val 155 | His | Leu | Ala | Ala | Pro 160 |
| Ala | Cys | Leu | Phe | Ser 165 | Ala | His | His | Asn | Arg 170 | Pro | Asp | Asp | Cys | Pro 175 | Asp |
| Cys | Val | Ala | Ser 180 | Pro | Leu | Gly | Thr | Arg 185 | Val | Thr | Val | Val | Glu 190 | Gln | Gly |
| Gln | Ala | Ser 195 | Tyr | Phe | Tyr | Val | Ala 200 | Ser | Ser | Leu | Asp | Ala 205 | Ala | Val | Ala |
| Gly | Ser 210 | Phe | Ser | Pro | Arg | Ser 215 | Val | Ser | Ile | Arg | Arg 220 | Leu | Lys | Ala | Asp |
| Ala 225 | Ser | Gly | Phe | Ala | Pro 230 | Gly | Phe | Val | Ala | Leu 235 | Ser | Val | Leu | Pro | Lys 240 |
| His | Leu | Val | Ser | Tyr 245 | Ser | Ile | Glu | Tyr | Val 250 | His | Ser | Phe | His | Thr 255 | Gly |
| Ala | Phe | Val | Tyr 260 | Phe | Leu | Thr | Val | Gln 265 | Pro | Ala | Ser | Val | Thr 270 | Asp | Asp |
| Pro | Ser | Ala 275 | Leu | His | Thr | Arg | Leu 280 | Ala | Arg | Leu | Ser | Ala 285 | Thr | Glu | Pro |
| Glu | Leu 290 | Gly | Asp | Tyr | Arg | Glu 295 | Leu | Val | Leu | Asp | Cys 300 | Arg | Phe | Ala | Pro |
| Lys 305 | Arg | Arg | Arg | Arg | Gly 310 | Ala | Pro | Glu | Gly | Gly 315 | Gln | Pro | Tyr | Pro | Val 320 |
| Leu | Gln | Val | Ala | His 325 | Ser | Ala | Pro | Val | Gly 330 | Ala | Gln | Leu | Ala | Thr 335 | Glu |
| Leu | Ser | Ile | Ala 340 | Glu | Gly | Gln | Glu | Val 345 | Leu | Phe | Gly | Val | Phe 350 | Val | Thr |
| Gly | Lys | Asp 355 | Gly | Gly | Pro | Gly | Val 360 | Gly | Pro | Asn | Ser | Val 365 | Val | Cys | Ala |
| Phe | Pro 370 | Ile | Asp | Leu | Leu | Asp 375 | Thr | Leu | Ile | Asp | Glu 380 | Gly | Val | Glu | Arg |
| Cys 385 | Cys | Glu | Ser | Pro | Val 390 | His | Pro | Gly | Leu | Arg 395 | Arg | Gly | Leu | Asp | Phe 400 |
| Phe | Gln | Ser | Pro | Ser 405 | Phe | Cys | Pro | Asn | Pro 410 | Pro | Gly | Leu | Glu | Ala 415 | Leu |
| Ser | Pro | Asn | Thr 420 | Ser | Cys | Arg | His | Phe 425 | Pro | Leu | Leu | Val | Ser 430 | Ser | Ser |
| Phe | Ser | Arg 435 | Val | Asp | Leu | Phe | Asn 440 | Gly | Leu | Leu | Gly | Pro 445 | Val | Gln | Val |
| Thr | Ala 450 | Leu | Tyr | Val | Thr | Arg 455 | Leu | Asp | Asn | Val | Thr 460 | Val | Ala | His | Met |
| Gly 465 | Thr | Met | Asp | Gly | Arg 470 | Ile | Leu | Gln | Val | Glu 475 | Leu | Val | Arg | Ser | Leu 480 |

FIG. 3B-2  SEQ ID NO: 6 cont.

```
Asn Tyr Leu Leu Tyr Val Ser Asn Phe Ser Leu Gly Asp Ser Gly Gln
            485             490             495
Pro Val Gln Arg Asp Val Ser Arg Leu Gly Asp His Leu Leu Phe Ala
            500             505             510
Ser Gly Asp Gln Val Phe Gln Val Pro Ile Arg Gly Pro Gly Cys Arg
            515             520             525
His Phe Leu Thr Cys Gly Arg Cys Leu Arg Ala Trp His Phe Met Gly
            530             535             540
Cys Gly Trp Cys Gly Asn Met Cys Gly Gln Gln Lys Glu Cys Pro Gly
545             550             555             560
Ser Trp Gln Gln Asp His Cys Pro Pro Lys Leu Thr Glu Phe His Pro
                565             570             575
His Ser Gly Pro Leu Arg Gly Ser Thr Arg Leu Thr Leu Cys Gly Ser
            580             585             590
Asn Phe Tyr Leu His Pro Ser Gly Leu Val Pro Glu Gly Thr His Gln
            595             600             605
Val Thr Val Gly Gln Ser Pro Cys Arg Pro Leu Pro Lys Asp Ser Ser
            610             615             620
Lys Leu Arg Pro Val Pro Arg Lys Asp Phe Val Glu Glu Phe Glu Cys
625             630             635             640
Glu Leu Glu Pro Leu Gly Thr Gln Ala Val Gly Pro Thr Asn Val Ser
                645             650             655
Leu Thr Val Thr Asn Met Pro Pro Gly Lys His Phe Arg Val Asp Gly
            660             665             670
Thr Ser Val Leu Arg Gly Phe Ser Phe Met Glu Pro Val Leu Ile Ala
            675             680             685
Val Gln Pro Leu Phe Gly Pro Arg Ala Gly Gly Thr Cys Leu Thr Leu
    690             695             700
Glu Gly Gln Ser Leu Ser Val Gly Thr Ser Arg Ala Val Leu Val Asn
705             710             715             720
Gly Thr Glu Cys Leu Leu Ala Arg Val Ser Glu Gly Gln Leu Leu Cys
                725             730             735
Ala Thr Pro Pro Gly Ala Thr Val Ala Ser Val Pro Leu Ser Leu Gln
            740             745             750
Val Gly Gly Ala Gln Val Pro Gly Ser Trp Thr Phe Gln Tyr Arg Glu
            755             760             765
Asp Pro Val Val Leu Ser Ile Ser Pro Asn Cys Gly Tyr Ile Asn Ser
    770             775             780
His Ile Thr Ile Cys Gly Gln His Leu Thr Ser Ala Trp His Leu Val
785             790             795             800
Leu Ser Phe His Asp Gly Leu Arg Ala Val Glu Ser Arg Cys Glu Arg
                805             810             815
Gln Leu Pro Glu Gln Gln Leu Cys Arg Leu Pro Glu Tyr Val Val Arg
            820             825             830
Asp Pro Gln Gly Trp Val Ala Gly Asn Leu Ser Ala Arg Gly Asp Gly
            835             840             845
Ala Ala Gly Phe Thr Leu Pro Gly Phe Arg Phe Leu Pro Pro Pro His
    850             855             860
Pro Pro Ser Ala Asn Leu Val Pro Leu Lys Pro Glu Glu His Ala Ile
865             870             875             880
Lys Phe Glu Leu Gly Gln Asp Gly Ala Pro Leu Gln Val Cys Val Asp
                885             890             895
Ala Leu Pro Ala Ile Asp Gly Leu Asp Ser Thr Thr Cys Val His Gly
            900             905             910
Ala Ser Phe Ser Asp Ser Glu Asp Glu Ser Cys Val Pro Leu Leu Arg
            915             920             925
Lys Glu Ser Ile Gln Leu Arg Asp Leu Asp Ser Ala Leu Leu Ala Glu
    930             935             940
Val Lys Asp Val Leu Ile Pro His Glu Arg Val Val Thr His Ser Asp
945             950             955             960
```

FIG. 3B-3  SEQ ID NO: 6 cont.

```
Arg Val Ile Gly Lys Gly His Phe Gly Val Val Tyr His Gly Glu Tyr
                965                 970                 975
Ile Asp Gln Ala Gln Asn Arg Ile Gln Cys Ala Ile Lys Ser Leu Ser
            980                 985                 990
Arg Ile Thr Glu Met Gln Gln Val Glu Ala Phe Leu Arg Glu Gly Leu
        995                 1000                1005
Leu Met Arg Gly Leu Asn His Pro Asn Val Leu Ala Leu Ile Gly Ile
    1010                1015                1020
Met Leu Pro Pro Glu Gly Leu Pro His Val Leu Leu Pro Tyr Met Cys
1025                1030                1035                1040
His Gly Asp Leu Leu Gln Phe Ile Arg Ser Pro Gln Arg Asn Pro Thr
                1045                1050                1055
Val Lys Asp Leu Ile Ser Phe Gly Leu Gln Val Ala Arg Gly Met Glu
            1060                1065                1070
Tyr Leu Ala Glu Gln Lys Phe Val His Arg Asp Leu Ala Ala Arg Asn
        1075                1080                1085
Cys Met Leu Asp Glu Ser Phe Thr Val Lys Val Ala Asp Phe Gly Leu
    1090                1095                1100
Ala Arg Asp Ile Leu Asp Arg Glu Tyr Tyr Ser Val Gln Gln His Arg
1105                1110                1115                1120
His Ala Arg Leu Pro Val Lys Trp Met Ala Leu Glu Ser Leu Gln Thr
                1125                1130                1135
Tyr Arg Phe Thr Thr Lys Ser Asp Val Val Pro Ser Asp Ala Ala Met
            1140                1145                1150
Leu Gly Gly Arg Pro Ser Ser Ala Thr His Leu Gln Ser Thr Ser Gly
        1155                1160                1165
Gly Gly Gly Ala Asp Ser Val Cys Thr Ala Trp Gly Pro Leu Cys Ala
    1170                1175                1180
Ala Ala Ser Asn Leu His Glu Leu Glu Leu Thr Pro Arg Leu Pro Leu
1185                1190                1195                1200
Gly His Ala Arg Pro Glu Gln Trp Pro Ser Thr Leu Phe Leu Pro Phe
                1205                1210                1215
Asn Phe Gln Arg Gln
                1220
```

FIG. 3C-1            Coding Sequence (SEQ ID NO: 5 & 6)

```
atg gag ctc ctc ccg ccg ctg cct cag tcc ttc ctg ttg ctg ctg    48
Met Glu Leu Leu Pro Pro Leu Pro Gln Ser Phe Leu Leu Leu Leu
              5                  10                  15
ttg cct gcc aag ccc gcg gcg ggc gag gac tgg cag tgc ccg cgc acc    96
Leu Pro Ala Lys Pro Ala Ala Gly Glu Asp Trp Gln Cys Pro Arg Thr
            20                  25                  30
ccc tac gcg gcc tct cgc gac ttt gac gtg aag tac gtg gtg ccc agc   144
Pro Tyr Ala Ala Ser Arg Asp Phe Asp Val Lys Tyr Val Val Pro Ser
        35                  40                  45
ttc tcc gcc gga ggc ctg gta cag gcc atg gtg acc tac gag ggc gac   192
Phe Ser Ala Gly Gly Leu Val Gln Ala Met Val Thr Tyr Glu Gly Asp
    50                  55                  60
aga aat gag agt gct gtg ttt gta gcc ata cgc aat cgc ctg cat gtg   240
Arg Asn Glu Ser Ala Val Phe Val Ala Ile Arg Asn Arg Leu His Val
65                  70                  75                  80
ctt ggg cct gac ctg aag tct gtc cag agc ctg gcc acg ggc cct gct   288
Leu Gly Pro Asp Leu Lys Ser Val Gln Ser Leu Ala Thr Gly Pro Ala
                85                  90                  95
gga gac cct ggc tgc cag acg tgt gca gcc tgt ggc cca gga ccc cac   336
Gly Asp Pro Gly Cys Gln Thr Cys Ala Ala Cys Gly Pro Gly Pro His
            100                 105                 110
ggc cct ccc ggt gac aca gac aca aag gtg ctg gtg ctg gat ccc gcg   384
Gly Pro Pro Gly Asp Thr Asp Thr Lys Val Leu Val Leu Asp Pro Ala
        115                 120                 125
ctg cct gcg ctg gtc agt tgt ggc tcc agc ctg cag ggc cgc tgc ttc   432
Leu Pro Ala Leu Val Ser Cys Gly Ser Ser Leu Gln Gly Arg Cys Phe
    130                 135                 140
ctg cat gac cta gag ccc caa ggg aca gcc gtg cat ctg gca gcg cca   480
Leu His Asp Leu Glu Pro Gln Gly Thr Ala Val His Leu Ala Ala Pro
145                 150                 155                 160
gcc tgc ctc ttc tca gcc cac cat aac cgg ccc gat gac tgc ccc gac   528
Ala Cys Leu Phe Ser Ala His His Asn Arg Pro Asp Asp Cys Pro Asp
                165                 170                 175
tgt gtg gcc agc cca ttg ggc acc cgt gta act gtg gtt gag caa ggc   576
Cys Val Ala Ser Pro Leu Gly Thr Arg Val Thr Val Val Glu Gln Gly
            180                 185                 190
cag gcc tcc tat ttc tac gtg gca tcc tca ctg gac gca gcc gtg gct   624
Gln Ala Ser Tyr Phe Tyr Val Ala Ser Ser Leu Asp Ala Ala Val Ala
        195                 200                 205
ggc agc ttc agc cca cgc tca gtg tct atc agg cgt ctc aag gct gac   672
Gly Ser Phe Ser Pro Arg Ser Val Ser Ile Arg Arg Leu Lys Ala Asp
    210                 215                 220
gcc tcg gga ttc gca ccg ggc ttt gtg gcg ttg tca gtg ctg ccc aag   720
Ala Ser Gly Phe Ala Pro Gly Phe Val Ala Leu Ser Val Leu Pro Lys
225                 230                 235                 240
cat ctt gtc tcc tac agt att gaa tac gtg cac agc ttc cac acg gga   768
His Leu Val Ser Tyr Ser Ile Glu Tyr Val His Ser Phe His Thr Gly
                245                 250                 255
gcc ttc gta tac ttc ctg act gta cag ccg gcc agc gtg aca gat gat   816
Ala Phe Val Tyr Phe Leu Thr Val Gln Pro Ala Ser Val Thr Asp Asp
            260                 265                 270
cct agt gcc ctg cac aca cgc ctg gca cgg ctt agc gcc act gag cca   864
Pro Ser Ala Leu His Thr Arg Leu Ala Arg Leu Ser Ala Thr Glu Pro
        275                 280                 285
gag ttg ggt gac tat cgg gag ctg gtc ctc gac tgc aga ttt gct cca   912
Glu Leu Gly Asp Tyr Arg Glu Leu Val Leu Asp Cys Arg Phe Ala Pro
    290                 295                 300
aaa cgc agg cgc cgg ggg gcc cca gaa ggc gga cag ccc tac cct gtg   960
Lys Arg Arg Arg Arg Gly Ala Pro Glu Gly Gly Gln Pro Tyr Pro Val
305                 310                 315                 320
```

FIG. 3C-2          Coding Sequence (SEQ ID NO: 5 & 6) cont.

```
ctg cag gtg gcc cac tcc gct cca gtg ggt gcc caa ctt gcc act gag 1008
Leu Gln Val Ala His Ser Ala Pro Val Gly Ala Gln Leu Ala Thr Glu
            325             330             335
ctg agc atc gcc gag ggc cag gaa gta cta ttt ggg gtc ttt gtg act 1056
Leu Ser Ile Ala Glu Gly Gln Glu Val Leu Phe Gly Val Phe Val Thr
            340             345             350
ggc aag gat ggt ggt cct ggc gtg ggc ccc aac tct gtc gtc tgt gcc 1104
Gly Lys Asp Gly Gly Pro Gly Val Gly Pro Asn Ser Val Val Cys Ala
            355             360             365
ttc ccc att gac ctg ctg gac aca cta att gat gag ggt gtg gag cgc 1152
Phe Pro Ile Asp Leu Leu Asp Thr Leu Ile Asp Glu Gly Val Glu Arg
    370             375             380
tgt tgt gaa tcc cca gtc cat cca ggc ctc cgg cga ggc ctc gac ttc 1200
Cys Cys Glu Ser Pro Val His Pro Gly Leu Arg Arg Gly Leu Asp Phe
385             390             395             400
ttc cag tcg ccc agt ttt tgc ccc aac ccg cct ggc ctg gaa gcc ctc 1248
Phe Gln Ser Pro Ser Phe Cys Pro Asn Pro Pro Gly Leu Glu Ala Leu
            405             410             415
agc ccc aac acc agc tgc cgc cac ttc cct ctg ctg gtc agt agc agc 1296
Ser Pro Asn Thr Ser Cys Arg His Phe Pro Leu Leu Val Ser Ser Ser
            420             425             430
ttc tca cgt gtg gac cta ttc aat ggg ctg ttg gga cca gta cag gtc 1344
Phe Ser Arg Val Asp Leu Phe Asn Gly Leu Leu Gly Pro Val Gln Val
            435             440             445
act gca ttg tat gtg aca cgc ctt gac aac gtc aca gtg gca cac atg 1392
Thr Ala Leu Tyr Val Thr Arg Leu Asp Asn Val Thr Val Ala His Met
    450             455             460
ggc aca atg gat ggg cgt atc ctg cag gtg gag ctg gtc agg tca cta 1440
Gly Thr Met Asp Gly Arg Ile Leu Gln Val Glu Leu Val Arg Ser Leu
465             470             475             480
aac tac ttg ctg tat gtg tcc aac ttc tca ctg ggt gac agt ggg cag 1488
Asn Tyr Leu Leu Tyr Val Ser Asn Phe Ser Leu Gly Asp Ser Gly Gln
            485             490             495
ccc gtg cag cgg gat gtc agt cgt ctt ggg gac cac cta ctc ttt gcc 1536
Pro Val Gln Arg Asp Val Ser Arg Leu Gly Asp His Leu Leu Phe Ala
            500             505             510
tct ggg gac cag gtt ttc cag gta cct atc cga ggc cct ggc tgc cgc 1584
Ser Gly Asp Gln Val Phe Gln Val Pro Ile Arg Gly Pro Gly Cys Arg
            515             520             525
cac ttc ctg acc tgt ggg cgt tgc cta agg gca tgg cat ttc atg ggc 1632
His Phe Leu Thr Cys Gly Arg Cys Leu Arg Ala Trp His Phe Met Gly
    530             535             540
tgt ggc tgg tgt ggg aac atg tgc ggc cag cag aag gag tgt cct ggc 1680
Cys Gly Trp Cys Gly Asn Met Cys Gly Gln Gln Lys Glu Cys Pro Gly
545             550             555             560
tcc tgg caa cag gac cac tgc cca cct aag ctt act gag ttc cac ccc 1728
Ser Trp Gln Gln Asp His Cys Pro Pro Lys Leu Thr Glu Phe His Pro
            565             570             575
cac agt gga cct cta agg ggc agt aca agg ctg acc ctg tgt ggc tcc 1776
His Ser Gly Pro Leu Arg Gly Ser Thr Arg Leu Thr Leu Cys Gly Ser
            580             585             590
aac ttc tac ctt cac cct tct ggt ctg gtg cct gag gga acc cat cag 1824
Asn Phe Tyr Leu His Pro Ser Gly Leu Val Pro Glu Gly Thr His Gln
            595             600             605
gtc act gtg ggc caa agt ccc tgc cgg cca ctg ccc aag gac agc tca 1872
Val Thr Val Gly Gln Ser Pro Cys Arg Pro Leu Pro Lys Asp Ser Ser
    610             615             620
aaa ctc aga cca gtg ccc cgg aaa gac ttt gta gag gag ttt gag tgt 1920
Lys Leu Arg Pro Val Pro Arg Lys Asp Phe Val Glu Glu Phe Glu Cys
625             630             635             640
```

FIG. 3C-3     Coding Sequence (SEQ ID NO: 5 & 6) cont.

```
gaa ctg gag ccc ttg ggc acc cag gca gtg ggg cct acc aac gtc agc   1968
Glu Leu Glu Pro Leu Gly Thr Gln Ala Val Gly Pro Thr Asn Val Ser
            645                 650                 655
ctc acc gtg act aac atg cca ccg ggc aag cac ttc cgg gta gac ggc   2016
Leu Thr Val Thr Asn Met Pro Pro Gly Lys His Phe Arg Val Asp Gly
            660                 665                 670
acc tcc gtg ctg aga ggc ttc tct ttc atg gag cca gtg ctg ata gca   2064
Thr Ser Val Leu Arg Gly Phe Ser Phe Met Glu Pro Val Leu Ile Ala
            675                 680                 685
gtg caa ccc ctc ttt ggc cca cgg gca gga ggc acc tgt ctc act ctt   2112
Val Gln Pro Leu Phe Gly Pro Arg Ala Gly Gly Thr Cys Leu Thr Leu
        690                 695                 700
gaa ggc cag agt ctg tct gta ggc acc agc cgg gct gtg ctg gtc aat   2160
Glu Gly Gln Ser Leu Ser Val Gly Thr Ser Arg Ala Val Leu Val Asn
705                 710                 715                 720
ggg act gag tgt ctg cta gca cgg gtc agt gag ggg cag ctt tta tgt   2208
Gly Thr Glu Cys Leu Leu Ala Arg Val Ser Glu Gly Gln Leu Leu Cys
                725                 730                 735
gcc aca ccc cct ggg gcc acg gtg gcc agt gtc ccc ctt agc ctg cag   2256
Ala Thr Pro Pro Gly Ala Thr Val Ala Ser Val Pro Leu Ser Leu Gln
            740                 745                 750
gtg ggg ggt gcc cag gta cct ggt tcc tgg acc ttc cag tac aga gaa   2304
Val Gly Gly Ala Gln Val Pro Gly Ser Trp Thr Phe Gln Tyr Arg Glu
            755                 760                 765
gac cct gtc gtg cta agc atc agc ccc aac tgt ggc tac atc aac tcc   2352
Asp Pro Val Val Leu Ser Ile Ser Pro Asn Cys Gly Tyr Ile Asn Ser
            770                 775                 780
cac atc acc atc tgt ggc cag cat cta act tca gca tgg cac tta gtg   2400
His Ile Thr Ile Cys Gly Gln His Leu Thr Ser Ala Trp His Leu Val
785                 790                 795                 800
ctg tca ttc cat gac ggg ctt agg gca gtg gaa agc agg tgt gag agg   2448
Leu Ser Phe His Asp Gly Leu Arg Ala Val Glu Ser Arg Cys Glu Arg
                805                 810                 815
cag ctt cca gag cag cag ctg tgc cgc ctt cct gaa tat gtg gtc cga   2496
Gln Leu Pro Glu Gln Gln Leu Cys Arg Leu Pro Glu Tyr Val Val Arg
            820                 825                 830
gac ccc cag gga tgg gtg gca ggg aat ctg agt gcc cga ggg gat gga   2544
Asp Pro Gln Gly Trp Val Ala Gly Asn Leu Ser Ala Arg Gly Asp Gly
            835                 840                 845
gct gct ggc ttt aca ctg cct ggc ttt cgc ttc cta ccc cca cat       2592
Ala Ala Gly Phe Thr Leu Pro Gly Phe Arg Phe Leu Pro Pro His
850                 855                 860
cca ccc agt gcc aac cta gtt cca ctg aag cct gag gag cat gcc att   2640
Pro Pro Ser Ala Asn Leu Val Pro Leu Lys Pro Glu Glu His Ala Ile
865                 870                 875                 880
aag ttt gag ctt ggc cag gat ggt gcc cca ttg cag gtc tgc gta gat   2688
Lys Phe Glu Leu Gly Gln Asp Gly Ala Pro Leu Gln Val Cys Val Asp
                885                 890                 895
gca ctc cct gcc att gat ggt ctg gat tcc acc act tgt gtc cat gga   2736
Ala Leu Pro Ala Ile Asp Gly Leu Asp Ser Thr Thr Cys Val His Gly
            900                 905                 910
gca tcc ttc tcc gat agt gaa gat gaa tcc tgt gtg cca ctg ctg cgg   2784
Ala Ser Phe Ser Asp Ser Glu Asp Glu Ser Cys Val Pro Leu Leu Arg
            915                 920                 925
aaa gag tcc atc cag cta agg gac ctg gac tct gcg ctc ttg gct gag   2832
Lys Glu Ser Ile Gln Leu Arg Asp Leu Asp Ser Ala Leu Leu Ala Glu
            930                 935                 940
gtc aag gat gtg ctg att ccc cat gag cgg gtg gtc acc cac agt gac   2880
Val Lys Asp Val Leu Ile Pro His Glu Arg Val Val Thr His Ser Asp
945                 950                 955                 960
```

FIG. 3C-4   Coding Sequence (SEQ ID NO: 5 & 6) cont.

```
cga gtc att ggc aaa ggc cac ttt gga gtt gtc tac cac gga gaa tac  2928
Arg Val Ile Gly Lys Gly His Phe Gly Val Val Tyr His Gly Glu Tyr
            965             970             975
ata gac cag gcc cag aat cga atc caa tgt gcc atc aag tca cta agt  2976
Ile Asp Gln Ala Gln Asn Arg Ile Gln Cys Ala Ile Lys Ser Leu Ser
        980             985             990
cgc atc aca gag atg cag cag gtg gag gcc ttc ctg cga gag ggg ctg  3024
Arg Ile Thr Glu Met Gln Gln Val Glu Ala Phe Leu Arg Glu Gly Leu
        995             1000            1005
ctc atg cgt ggc ctg aac cac ccg aat gtg ctg gct ctc att ggt atc  3072
Leu Met Arg Gly Leu Asn His Pro Asn Val Leu Ala Leu Ile Gly Ile
    1010            1015            1020
atg ttg cca cct gag ggc ctg ccc cat gtg ctg ctg ccc tat atg tgc  3120
Met Leu Pro Pro Glu Gly Leu Pro His Val Leu Leu Pro Tyr Met Cys
1025            1030            1035            1040
cac ggt gac ctg ctc cag ttc atc cgc tca cct cag cgg aac ccc acc  3168
His Gly Asp Leu Leu Gln Phe Ile Arg Ser Pro Gln Arg Asn Pro Thr
                1045            1050            1055
gtg aag gac ctc atc agc ttt ggc ctg cag gta gcc cgc ggc atg gag  3216
Val Lys Asp Leu Ile Ser Phe Gly Leu Gln Val Ala Arg Gly Met Glu
            1060            1065            1070
tac ctg gca gag cag aag ttt gtg cac agg gac ctg gct gcg cgg aac  3264
Tyr Leu Ala Glu Gln Lys Phe Val His Arg Asp Leu Ala Ala Arg Asn
        1075            1080            1085
tgc atg ctg gac gag tca ttc aca gtc aag gtg gct gac ttt ggt ttg  3312
Cys Met Leu Asp Glu Ser Phe Thr Val Lys Val Ala Asp Phe Gly Leu
        1090            1095            1100
gcc cgc gac atc ctg gac agg gag tac tat agt gtt caa cag cat cgc  3360
Ala Arg Asp Ile Leu Asp Arg Glu Tyr Tyr Ser Val Gln Gln His Arg
1105            1110            1115            1120
cac gct cgc cta cct gtg aag tgg atg gcg ctg gag agc ctg cag acc  3408
His Ala Arg Leu Pro Val Lys Trp Met Ala Leu Glu Ser Leu Gln Thr
                1125            1130            1135
tat aga ttt acc acc aag tct gat gtg gta cca agt gat gca gca atg  3456
Tyr Arg Phe Thr Thr Lys Ser Asp Val Val Pro Ser Asp Ala Ala Met
            1140            1145            1150
ctg gga ggc aga ccc agc agt gcg acc cac ctt cag agt act agt ggg  3504
Leu Gly Gly Arg Pro Ser Ser Ala Thr His Leu Gln Ser Thr Ser Gly
        1155            1160            1165
gga ggt gga gca gat agt gtc tgc act gct tgg gga cca tta tgt gca  3552
Gly Gly Gly Ala Asp Ser Val Cys Thr Ala Trp Gly Pro Leu Cys Ala
        1170            1175            1180
gct gcc agc aac cta cat gaa ctt gag cta acc cca agg ctg cct ctg  3600
Ala Ala Ser Asn Leu His Glu Leu Glu Leu Thr Pro Arg Leu Pro Leu
1185            1190            1195            1200
ggc cat gcc agg cca gag cag tgg ccc tcc acc ttg ttc ctg ccc ttt  3648
Gly His Ala Arg Pro Glu Gln Trp Pro Ser Thr Leu Phe Leu Pro Phe
                1205            1210            1215
aac ttt cag agg caa                                              3663
Asn Phe Gln Arg Gln
            1220
```

FIG. 4A-1  SEQ ID NO: 7

```
GGATCCTCTA GGGTCCCAGC TCGCCTCGAT GGAGCTCCTC CCGCCGCTGC CTCAGTCCTT    60
CCTGTTGCTG CTGCTGTTGC CTGCCAAGCC CGCGGCGGGC GAGGACTGGC AGTGCCCGCG   120
CACCCCCTAC GCGGCCTCTC GCGACTTTGA CGTGAAGTAC GTGGTGCCCA GCTTCTCCGC   180
CGGAGGCCTG GTACAGGCCA TGGTGACCTA CGAGGGCGAC AGAAATGAGA GTGCTGTGTT   240
TGTAGCCATA CGCAATCGCC TGCATGTGCT TGGGCCTGAC CTGAAGTCTG TCCAGAGCCT   300
GGCCACGGGC CCTGCTGGAG ACCCTGGCTG CCAGACGTGT GCAGCCTGTG GCCCAGGACC   360
CCACGGCCCT CCCGGTGACA CAGACACAAA GGTGCTGGTG CTGGATCCCG CGCTGCCTGC   420
GCTGGTCAGT TGTGGCTCCA GCCTGCAGGG CCGCTGCTTC CTGCATGACC TAGAGCCCCA   480
AGGGACAGCC GTGCATCTGG CAGCGCCAGC CTGCCTCTTC TCAGCCCACC ATAACCGGCC   540
CGATGACTGC CCCGACTGTG TGGCCAGCCC ATTGGGCACC CGTGTAACTG TGGTTGAGCA   600
AGGCCAGGCC TCCTATTTCT ACGTGGCATC CTCACTGGAC GCAGCCGTGG CTGGCAGCTT   660
CAGCCCACGC TCAGTGTCTA TCAGGCGTCT CAAGGCTGAC GCCTCGGGAT TCGCACCGGG   720
CTTTGTGGCG TTGTCAGTGC TGCCCAAGCA TCTTGTCTCC TACAGTATTG AATACGTGCA   780
CAGCTTCCAC ACGGGAGCCT TCGTATACTT CCTGACTGTA CAGCCGGCCA GCGTGACAGA   840
TGATCCTAGT GCCCTGCACA CACGCCTGGC ACGGCTTAGC GCCACTGAGC CAGAGTTGGG   900
TGACTATCGG GAGCTGGTCC TCGACTGCAG ATTTGCTCCA AAACGCAGGC GCCGGGGGGC   960
CCCAGAAGGC GGACAGCCCT ACCCTGTGCT GCAGGTGGCC CACTCCGCTC CAGTGGGTGC  1020
CCAACTTGCC ACTGAGCTGA GCATCGCCGA GGGCCAGGAA GTACTATTTG GGGTCTTTGT  1080
GACTGGCAAG GATGGTGGTC CTGGCGTGGG CCCCAACTCT GTCGTCTGTG CCTTCCCCAT  1140
TGACCTGCTG GACACACTAA TTGATGAGGG TGTGGAGCGC TGTTGTGAAT CCCCAGTCCA  1200
TCCAGGCCTC CGGCGAGGCC TCGACTTCTT CCAGTCGCCC AGTTTTTGCC CCAACCCGCC  1260
TGGCCTGGAA GCCCTCAGCC CCAACACCAG CTGCCGCCAC TTCCCTCTGC TGGTCAGTAG  1320
CAGCTTCTCA CGTGTGGACC TATTCAATGG GCTGTTGGGA CCAGTACAGG TCACTGCATT  1380
GTATGTGACA CGCCTTGACA ACGTCACAGT GGCACACATG GGCACAATGG ATGGGCGTAT  1440
CCTGCAGGTG GAGCTGGTCA GGTCACTAAA CTACTTGCTG TATGTGTCCA ACTTCTCACT  1500
GGGTGACAGT GGGCAGCCCG TGCAGCGGGA TGTCAGTCGT CTTGGGGACC ACCTACTCTT  1560
TGCCTCTGGG GACCAGGTTT TCCAGGTACC TATCCGAGGC CCTGGCTGCC GCCACTTCCT  1620
GACCTGTGGG CGTTGCCTAA GGGCATGGCA TTTCATGGGC TGTGGCTGGT GTGGGAACAT  1680
GTGCGGCCAG CAGAAGGAGT GTCCTGGCTC CTGGCAACAG GACCACTGCC CACCTAAGCT  1740
TACTGAGTTC CACCCCCACA GTGGACCTCT AAGGGGCAGT ACAAGGCTGA CCCTGTGTGG  1800
CTCCAACTTC TACCTTCACC CTTCTGGTCT GGTGCCTGAG GAACCCATC AGGTCACTGT  1860
GGGCCAAAGT CCCTGCCGGC CACTGCCCAA GGACAGCTCA AAACTCAGAC CAGTGCCCCG  1920
GAAAGACTTT GTAGAGGAGT TTGAGTGTGA ACTGGAGCCC TTGGGCACCC AGGCAGTGGG  1980
GCCTACCAAC GTCAGCCTCA CCGTGACTAA CATGCCACCG GGCAAGCACT TCCGGGTAGA  2040
CGGCACCTCC GTGCTGAGAG GCTTCTCTTT CATGGAGCCA GTGCTGATAG CAGTGCAACC  2100
CCTCTTTGGC CCACGGGCAG GAGGCACCTG TCTCACTCTT GAAGGCAGA GTCTGTCTGT  2160
AGGCACCAGC CGGGCTGTGC TGGTCAATGG GACTGAGTGT CTGCTAGCAC GGGTCAGTGA  2220
GGGGCAGCTT TTATGTGCCA CACCCCTGGG GGCCACGGTG GCCAGTGTCC CCCTTAGCCT  2280
```

FIG. 4A-2            SEQ ID NO: 7 cont.

```
GCAGGTGGGG  GGTGCCCAGG  TACCTGGTTC  CTGGACCTTC  CAGTACAGAG  AAGACCCTGT  2340
CGTGCTAAGC  ATCAGCCCCA  ACTGTGGCTA  CATCAACTCC  CACATCACCA  TCTGTGGCCA  2400
GCATCTAACT  TCAGCATGGC  ACTTAGTGCT  GTCATTCCAT  GACGGGCTTA  GGGCAGTGGA  2460
AAGCAGGTGT  GAGAGGCAGC  TTCCAGAGCA  GCAGCTGTGC  CGCCTTCCTG  AATATGTGGT  2520
CCGAGACCCC  CAGGGATGGG  TGGCAGGGAA  TCTGAGTGCC  CGAGGGGATG  GAGCTGCTGG  2580
CTTTACACTG  CCTGGCTTTC  GCTTCCTACC  CCCACCCCAT  CCACCCAGTG  CCAACCTAGT  2640
TCCACTGAAG  CCTGAGGAGC  ATGCCATTAA  GTTTGAGGTC  TGCGTAGATG  CACTCCCTGC  2700
CATTGATGGT  CTGGATTCCA  CCACTTGTGT  CCATGGAGCA  TCCTTCTCCG  ATAGTGAAGA  2760
TGAATCCTGT  GTGCCACTGC  TGCGGAAAGA  GTCCATCCAG  CTAAGGGACC  TGGACTCTGC  2820
GCTCTTGGCT  GAGGTCAAGG  ATGTGCTGAT  TCCCCATGAG  CGGGTGGTCA  CCCACAGTGA  2880
CCGAGTCATT  GGCAAAGGCC  ACTTTGGAGT  TGTCTACCAC  GGAGAATACA  TAGACCAGGC  2940
CCAGAATCGA  ATCCAATGTG  CCATCAAGTC  ACTAAGTCGC  ATCACAGAGA  TGCAGCAGGT  3000
GGAGGCCTTC  CTGCGAGAGG  GGCTGCTCAT  GCGTGGCCTG  AACCACCCGA  ATGTGCTGGC  3060
TCTCATTGGT  ATCATGTTGC  CACCTGAGGG  CCTGCCCCAT  GTGCTGCTGC  CCTATATGTG  3120
CCACGGTGAC  CTGCTCCAGT  TCATCCGCTC  ACCTCAGCGG  AACCCCACCG  TGAAGGACCT  3180
CATCAGCTTT  GGCCTGCAGG  TAGCCCGCGG  CATGGAGTAC  CTGGCAGAGC  AGAAGTTTGT  3240
GCACAGGGAC  CTGGCTGCGC  GGAACTGCAT  GCTGGACGAG  TCATTCACAG  TCAAGGTGGC  3300
TGACTTTGGT  TTGGCCCGCG  ACATCCTGGA  CAGGGAGTAC  TATAGTGTTC  AACAGCATCG  3360
CCACGCTCGC  CTACCTGTGA  AGTGGATGGC  GCTGGAGAGC  CTGCAGACCT  ATAGATTTAC  3420
CACCAAGTCT  GATGTGGTAC  CAAGTGATGC  AGCAATGCTG  GGAGGCAGAC  CCAGCAGTGC  3480
GACCCACCTT  CAGAGTACTA  GTGGGGAGG   TGGAGCAGAT  AGTGTCTGCA  CTGCTTGGGG  3540
ACCATTATGT  GCAGCTGCCA  GCAACCTACA  TGAACTTGAG  CTAACCCCAA  GGCTGCCTCT  3600
GGGCCATGCC  AGGCCAGAGC  AGTGGCCCTC  CACCTTGTTC  CTGCCCTTTA  ACTTTCAGAG  3660
GCAATAGGTA  AATGGGCCCA  TTAGGTCCCT  CACTCCACAG  AGTGAGCCAG  TGAGGGCAGT  3720
CCTGCAACAT  GTATTTATGG  AGTGCCTGCT  GTGGACCCTG  TCTTCTGGGC  ACAGTGGACT  3780
CAGCAGTGAC  CACACCAACA  CTGACCCTTG  AACCAATAAA  GGAACAAATG  ACTATTAAAG  3840
CACAAAAAAA  AAA                                                        3853
```

FIG. 4B-1  SEQ ID NO: 8

| 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|
| Met | Glu | Leu | Leu | Pro | Pro | Leu | Pro | Gln | Ser | Phe | Leu | Leu | Leu | Leu |
| Leu | Pro | Ala | Lys | Pro | Ala | Ala | Gly | Glu | Asp | Trp | Gln | Cys | Pro | Arg |
| Thr | Pro | Tyr | Ala | Ala | Ser | Arg | Asp | Phe | Asp | Val | Lys | Tyr | Val | Val |
| Pro | Ser | Phe | Ser | Ala | Gly | Gly | Leu | Val | Gln | Ala | Met | Val | Thr | Tyr |
| Glu | Gly | Asp | Arg | Asn | Glu | Ser | Ala | Val | Phe | Val | Ala | Ile | Arg | Asn |
| Arg | Leu | His | Val | Leu | Gly | Pro | Asp | Leu | Lys | Ser | Val | Gln | Ser | Leu |
| Ala | Thr | Gly | Pro | Ala | Gly | Asp | Pro | Gly | Cys | Gln | Thr | Cys | Ala | Ala |
| Cys | Gly | Pro | Gly | Pro | His | Gly | Pro | Pro | Gly | Asp | Thr | Asp | Thr | Lys |
| Val | Leu | Val | Leu | Asp | Pro | Ala | Leu | Pro | Ala | Leu | Val | Ser | Cys | Gly |
| Ser | Ser | Leu | Gln | Gly | Arg | Cys | Phe | Leu | His | Asp | Leu | Glu | Pro | Gln |
| Gly | Thr | Ala | Val | His | Leu | Ala | Ala | Pro | Ala | Cys | Leu | Phe | Ser | Ala |
| His | His | Asn | Arg | Pro | Asp | Asp | Cys | Pro | Asp | Cys | Val | Ala | Ser | Pro |
| Leu | Gly | Thr | Arg | Val | Thr | Val | Val | Glu | Gln | Gly | Gln | Ala | Ser | Tyr |
| Phe | Tyr | Val | Ala | Ser | Ser | Leu | Asp | Ala | Ala | Val | Ala | Gly | Ser | Phe |
| Ser | Pro | Arg | Ser | Val | Ser | Ile | Arg | Arg | Leu | Lys | Ala | Asp | Ala | Ser |
| Gly | Phe | Ala | Pro | Gly | Phe | Val | Ala | Leu | Ser | Val | Leu | Pro | Lys | His |
| Leu | Val | Ser | Tyr | Ser | Ile | Glu | Tyr | Val | His | Ser | Phe | His | Thr | Gly |
| Ala | Phe | Val | Tyr | Phe | Leu | Thr | Val | Gln | Pro | Ala | Ser | Val | Thr | Asp |
| Asp | Pro | Ser | Ala | Leu | His | Thr | Arg | Leu | Ala | Arg | Leu | Ser | Ala | Thr |
| Glu | Pro | Glu | Leu | Gly | Asp | Tyr | Arg | Glu | Leu | Val | Leu | Asp | Cys | Arg |
| Phe | Ala | Pro | Lys | Arg | Arg | Arg | Arg | Gly | Ala | Pro | Glu | Gly | Gly | Gln |
| Pro | Tyr | Pro | Val | Leu | Gln | Val | Ala | His | Ser | Ala | Pro | Val | Gly | Ala |
| Gln | Leu | Ala | Thr | Glu | Leu | Ser | Ile | Ala | Glu | Gly | Gln | Glu | Val | Leu |
| Phe | Gly | Val | Phe | Val | Thr | Gly | Lys | Asp | Gly | Gly | Pro | Gly | Val | Gly |
| Pro | Asn | Ser | Val | Val | Cys | Ala | Phe | Pro | Ile | Asp | Leu | Leu | Asp | Thr |
| Leu | Ile | Asp | Glu | Gly | Val | Glu | Arg | Cys | Cys | Glu | Ser | Pro | Val | His |
| Pro | Gly | Leu | Arg | Arg | Gly | Leu | Asp | Phe | Phe | Gln | Ser | Pro | Ser | Phe |
| Cys | Pro | Asn | Pro | Pro | Gly | Leu | Glu | Ala | Leu | Ser | Pro | Asn | Thr | Ser |
| Cys | Arg | His | Phe | Pro | Leu | Leu | Val | Ser | Ser | Ser | Phe | Ser | Arg | Val |
| Asp | Leu | Phe | Asn | Gly | Leu | Leu | Gly | Pro | Val | Gln | Val | Thr | Ala | Leu |
| Tyr | Val | Thr | Arg | Leu | Asp | Asn | Val | Thr | Val | Ala | His | Met | Gly | Thr |
| Met | Asp | Gly | Arg | Ile | Leu | Gln | Val | Glu | Leu | Val | Arg | Ser | Leu | |

(Numbered positions: 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480)

FIG. 4B-2 SEQ ID NO: 8 cont.

```
Asn Tyr Leu Leu Tyr Val Ser Asn Phe Ser Leu Gly Asp Ser Gly Gln
            485             490                 495
Pro Val Gln Arg Asp Val Ser Arg Leu Gly Asp His Leu Leu Phe Ala
        500             505                 510
Ser Gly Asp Gln Val Phe Gln Val Pro Ile Arg Gly Pro Gly Cys Arg
            515             520                 525
His Phe Leu Thr Cys Gly Arg Cys Leu Arg Ala Trp His Phe Met Gly
        530             535                 540
Cys Gly Trp Cys Gly Asn Met Cys Gly Gln Gln Lys Glu Cys Pro Gly
545             550             555                 560
Ser Trp Gln Gln Asp His Cys Pro Pro Lys Leu Thr Glu Phe His Pro
                565             570                 575
His Ser Gly Pro Leu Arg Gly Ser Thr Arg Leu Thr Leu Cys Gly Ser
            580             585                 590
Asn Phe Tyr Leu His Pro Ser Gly Leu Val Pro Glu Gly Thr His Gln
        595             600                 605
Val Thr Val Gly Gln Ser Pro Cys Arg Pro Leu Pro Lys Asp Ser Ser
    610             615                 620
Lys Leu Arg Pro Val Pro Arg Lys Asp Phe Val Glu Glu Phe Glu Cys
625             630             635                 640
Glu Leu Glu Pro Leu Gly Thr Gln Ala Val Gly Pro Thr Asn Val Ser
                645             650                 655
Leu Thr Val Thr Asn Met Pro Pro Gly Lys His Phe Arg Val Asp Gly
            660             665                 670
Thr Ser Val Leu Arg Gly Phe Ser Phe Met Glu Pro Val Leu Ile Ala
        675             680                 685
Val Gln Pro Leu Phe Gly Pro Arg Ala Gly Gly Thr Cys Leu Thr Leu
    690             695                 700
Glu Gly Gln Ser Leu Ser Val Gly Thr Ser Arg Ala Val Leu Val Asn
705             710             715                 720
Gly Thr Glu Cys Leu Leu Ala Arg Val Ser Glu Gly Gln Leu Leu Cys
                725             730                 735
Ala Thr Pro Pro Gly Ala Thr Val Ala Ser Val Pro Leu Ser Leu Gln
            740             745                 750
Val Gly Gly Ala Gln Val Pro Gly Ser Trp Thr Phe Gln Tyr Arg Glu
        755             760                 765
Asp Pro Val Val Leu Ser Ile Ser Pro Asn Cys Gly Tyr Ile Asn Ser
    770             775                 780
His Ile Thr Ile Cys Gly Gln His Leu Thr Ser Ala Trp His Leu Val
785             790             795                 800
Leu Ser Phe His Asp Gly Leu Arg Ala Val Glu Ser Arg Cys Glu Arg
                805             810                 815
Gln Leu Pro Glu Gln Gln Leu Cys Arg Leu Pro Glu Tyr Val Val Arg
            820             825                 830
Asp Pro Gln Gly Trp Val Ala Gly Asn Leu Ser Ala Arg Gly Asp Gly
        835             840                 845
Ala Ala Gly Phe Thr Leu Pro Gly Phe Arg Phe Leu Pro Pro Pro His
    850             855                 860
Pro Pro Ser Ala Asn Leu Val Pro Leu Lys Pro Glu Glu His Ala Ile
865             870             875                 880
Lys Phe Glu Val Cys Val Asp Ala Leu Pro Ala Ile Asp Gly Leu Asp
                885             890                 895
Ser Thr Thr Cys Val His Gly Ala Ser Phe Ser Asp Ser Glu Asp Glu
            900             905                 910
Ser Cys Val Pro Leu Leu Arg Lys Glu Ser Ile Gln Leu Arg Asp Leu
        915             920                 925
Asp Ser Ala Leu Leu Ala Glu Val Lys Asp Val Leu Ile Pro His Glu
    930             935                 940
Arg Val Val Thr His Ser Asp Arg Val Ile Gly Lys Gly His Phe Gly
945             950             955                 960
```

FIG. 4B-3          SEQ ID NO: 8 cont.

```
Val  Val  Tyr  His  Gly  Glu  Tyr  Ile  Asp  Gln  Ala  Gln  Asn  Arg  Ile  Gln
                    965                 970                           975
Cys  Ala  Ile  Lys  Ser  Leu  Ser  Arg  Ile  Thr  Glu  Met  Gln  Gln  Val  Glu
                    980                 985                           990
Ala  Phe  Leu  Arg  Glu  Gly  Leu  Leu  Met  Arg  Gly  Leu  Asn  His  Pro  Asn
               995                 1000                     1005
Val  Leu  Ala  Leu  Ile  Gly  Ile  Met  Leu  Pro  Pro  Glu  Gly  Leu  Pro  His
          1010                1015                1020
Val  Leu  Leu  Pro  Tyr  Met  Cys  His  Gly  Asp  Leu  Leu  Gln  Phe  Ile  Arg
1025                1030                     1035                          1040
Ser  Pro  Gln  Arg  Asn  Pro  Thr  Val  Lys  Asp  Leu  Ile  Ser  Phe  Gly  Leu
                    1045                1050                     1055
Gln  Val  Ala  Arg  Gly  Met  Glu  Tyr  Leu  Ala  Glu  Gln  Lys  Phe  Val  His
                1060                1065                     1070
Arg  Asp  Leu  Ala  Ala  Arg  Asn  Cys  Met  Leu  Asp  Glu  Ser  Phe  Thr  Val
               1075                1080                     1085
Lys  Val  Ala  Asp  Phe  Gly  Leu  Ala  Arg  Asp  Ile  Leu  Asp  Arg  Glu  Tyr
     1090                     1095                1100
Tyr  Ser  Val  Gln  Gln  His  Arg  His  Ala  Arg  Leu  Pro  Val  Lys  Trp  Met
1105                1110                     1115                          1120
Ala  Leu  Glu  Ser  Leu  Gln  Thr  Tyr  Arg  Phe  Thr  Thr  Lys  Ser  Asp  Val
                    1125                1130                     1135
Val  Pro  Ser  Asp  Ala  Ala  Met  Leu  Gly  Gly  Arg  Pro  Ser  Ser  Ala  Thr
               1140                1145                     1150
His  Leu  Gln  Ser  Thr  Ser  Gly  Gly  Gly  Ala  Asp  Ser  Val  Cys  Thr
               1155                1160                     1165
Ala  Trp  Gly  Pro  Leu  Cys  Ala  Ala  Ser  Asn  Leu  His  Glu  Leu  Glu
     1170                     1175                1180
Leu  Thr  Pro  Arg  Leu  Pro  Leu  Gly  His  Ala  Arg  Pro  Glu  Gln  Trp  Pro
1185                     1190                1195                          1200
Ser  Thr  Leu  Phe  Leu  Pro  Phe  Asn  Phe  Gln  Arg  Gln
                    1205                     1210
```

FIG. 4C-1    Coding Sequence (SEQ ID NO: 7 & 8)

```
ATG GAG CTC CTC CCG CCG CTG CCT CAG TCC TTC CTG TTG CTG CTG CTG   48
Met Glu Leu Leu Pro Pro Leu Pro Gln Ser Phe Leu Leu Leu Leu Leu
             5                   10                      15
TTG CCT GCC AAG CCC GCG GCG GGC GAG GAC TGG CAG TGC CCG CGC ACC   96
Leu Pro Ala Lys Pro Ala Ala Gly Glu Asp Trp Gln Cys Pro Arg Thr
             20                  25                  30
CCC TAC GCG GCC TCT CGC GAC TTT GAC GTG AAG TAC GTG GTG CCC AGC  144
Pro Tyr Ala Ala Ser Arg Asp Phe Asp Val Lys Tyr Val Val Pro Ser
         35                  40                  45
TTC TCC GCC GGA GGC CTG GTA CAG GCC ATG GTG ACC TAC GAG GGC GAC  192
Phe Ser Ala Gly Gly Leu Val Gln Ala Met Val Thr Tyr Glu Gly Asp
         50                  55                  60
AGA AAT GAG AGT GCT GTG TTT GTA GCC ATA CGC AAT CGC CTG CAT GTG  240
Arg Asn Glu Ser Ala Val Phe Val Ala Ile Arg Asn Arg Leu His Val
65                   70                  75                  80
CTT GGG CCT GAC CTG AAG TCT GTC CAG AGC CTG GCC ACG GGC CCT GCT  288
Leu Gly Pro Asp Leu Lys Ser Val Gln Ser Leu Ala Thr Gly Pro Ala
                     85                  90                  95
GGA GAC CCT GGC TGC CAG ACG TGT GCA GCC TGT GGC CCA GGA CCC CAC  336
Gly Asp Pro Gly Cys Gln Thr Cys Ala Ala Cys Gly Pro Gly Pro His
                 100                 105                 110
GGC CCT CCC GGT GAC ACA GAC ACA AAG GTG CTG GTG CTG GAT CCC GCG  384
Gly Pro Pro Gly Asp Thr Asp Thr Lys Val Leu Val Leu Asp Pro Ala
             115                 120                 125
CTG CCT GCG CTG GTC AGT TGT GGC TCC AGC CTG CAG GGC CGC TGC TTC  432
Leu Pro Ala Leu Val Ser Cys Gly Ser Ser Leu Gln Gly Arg Cys Phe
    130                 135                 140
CTG CAT GAC CTA GAG CCC CAA GGG ACA GCC GTG CAT CTG GCA GCG CCA  480
Leu His Asp Leu Glu Pro Gln Gly Thr Ala Val His Leu Ala Ala Pro
145                 150                 155                 160
GCC TGC CTC TTC TCA GCC CAC CAT AAC CGG CCC GAT GAC TGC CCC GAC  528
Ala Cys Leu Phe Ser Ala His His Asn Arg Pro Asp Asp Cys Pro Asp
                    165                 170                 175
TGT GTG GCC AGC CCA TTG GGC ACC CGT GTA ACT GTG GTT GAG CAA GGC  576
Cys Val Ala Ser Pro Leu Gly Thr Arg Val Thr Val Val Glu Gln Gly
                180                 185                 190
CAG GCC TCC TAT TTC TAC GTG GCA TCC TCA CTG GAC GCA GCC GTG GCT  624
Gln Ala Ser Tyr Phe Tyr Val Ala Ser Ser Leu Asp Ala Ala Val Ala
        195                 200                 205
GGC AGC TTC AGC CCA CGC TCA GTG TCT ATC AGG CGT CTC AAG GCT GAC  672
Gly Ser Phe Ser Pro Arg Ser Val Ser Ile Arg Arg Leu Lys Ala Asp
    210                 215                 220
GCC TCG GGA TTC GCA CCG GGC TTT GTG GCG TTG TCA GTG CTG CCC AAG  720
Ala Ser Gly Phe Ala Pro Gly Phe Val Ala Leu Ser Val Leu Pro Lys
225                 230                 235                 240
CAT CTT GTC TCC TAC AGT ATT GAA TAC GTG CAC AGC TTC CAC ACG GGA  768
His Leu Val Ser Tyr Ser Ile Glu Tyr Val His Ser Phe His Thr Gly
                    245                 250                 255
GCC TTC GTA TAC TTC CTG ACT GTA CAG CCG GCC AGC GTG ACA GAT GAT  816
Ala Phe Val Tyr Phe Leu Thr Val Gln Pro Ala Ser Val Thr Asp Asp
                260                 265                 270
CCT AGT GCC CTG CAC ACA CGC CTG GCA CGG CTT AGC GCC ACT GAG CCA  864
Pro Ser Ala Leu His Thr Arg Leu Ala Arg Leu Ser Ala Thr Glu Pro
        275                 280                 285
GAG TTG GGT GAC TAT CGG GAG CTG GTC CTC GAC TGC AGA TTT GCT CCA  912
Glu Leu Gly Asp Tyr Arg Glu Leu Val Leu Asp Cys Arg Phe Ala Pro
    290                 295                 300
AAA CGC AGG CGC CGG GGG GCC CCA GAA GGC GGA CAG CCC TAC CCT GTG  960
Lys Arg Arg Arg Arg Gly Ala Pro Glu Gly Gly Gln Pro Tyr Pro Val
305                 310                 315                 320
```

FIG. 4C-2     Coding Sequence (SEQ ID NO: 7 & 8) cont.

```
CTG CAG GTG GCC CAC TCC GCT CCA GTG GGT GCC CAA CTT GCC ACT GAG 1008
Leu Gln Val Ala His Ser Ala Pro Val Gly Ala Gln Leu Ala Thr Glu
            325             330                 335
CTG AGC ATC GCC GAG GGC CAG GAA GTA CTA TTT GGG GTC TTT GTG ACT 1056
Leu Ser Ile Ala Glu Gly Gln Glu Val Leu Phe Gly Val Phe Val Thr
            340             345                 350
GGC AAG GAT GGT GGT CCT GGC GTG GGC CCC AAC TCT GTC GTC TGT GCC 1104
Gly Lys Asp Gly Gly Pro Gly Val Gly Pro Asn Ser Val Val Cys Ala
            355             360                 365
TTC CCC ATT GAC CTG CTG GAC ACA CTA ATT GAT GAG GGT GTG GAG CGC 1152
Phe Pro Ile Asp Leu Leu Asp Thr Leu Ile Asp Glu Gly Val Glu Arg
    370                 375             380
TGT TGT GAA TCC CCA GTC CAT CCA GGC CTC CGG CGA GGC CTC GAC TTC 1200
Cys Cys Glu Ser Pro Val His Pro Gly Leu Arg Arg Gly Leu Asp Phe
385             390                 395                 400
TTC CAG TCG CCC AGT TTT TGC CCC AAC CCG CCT GGC CTG GAA GCC CTC 1248
Phe Gln Ser Pro Ser Phe Cys Pro Asn Pro Pro Gly Leu Glu Ala Leu
                405             410                 415
AGC CCC AAC ACC AGC TGC CGC CAC TTC CCT CTG CTG GTC AGT AGC AGC 1296
Ser Pro Asn Thr Ser Cys Arg His Phe Pro Leu Leu Val Ser Ser Ser
            420                 425             430
TTC TCA CGT GTG GAC CTA TTC AAT GGG CTG TTG GGA CCA GTA CAG GTC 1344
Phe Ser Arg Val Asp Leu Phe Asn Gly Leu Leu Gly Pro Val Gln Val
        435             440                 445
ACT GCA TTG TAT GTG ACA CGC CTT GAC AAC GTC ACA GTG GCA CAC ATG 1392
Thr Ala Leu Tyr Val Thr Arg Leu Asp Asn Val Thr Val Ala His Met
    450                 455             460
GGC ACA ATG GAT GGG CGT ATC CTG CAG GTG GAG CTG GTC AGG TCA CTA 1440
Gly Thr Met Asp Gly Arg Ile Leu Gln Val Glu Leu Val Arg Ser Leu
465                 470              475                 480
AAC TAC TTG CTG TAT GTG TCC AAC TTC TCA CTG GGT GAC AGT GGG CAG 1488
Asn Tyr Leu Leu Tyr Val Ser Asn Phe Ser Leu Gly Asp Ser Gly Gln
                485             490                 495
CCC GTG CAG CGG GAT GTC AGT CGT CTT GGG GAC CAC CTA CTC TTT GCC 1536
Pro Val Gln Arg Asp Val Ser Arg Leu Gly Asp His Leu Leu Phe Ala
            500                 505             510
TCT GGG GAC CAG GTT TTC CAG GTA CCT ATC CGA GGC CCT GGC TGC CGC 1584
Ser Gly Asp Gln Val Phe Gln Val Pro Ile Arg Gly Pro Gly Cys Arg
        515                 520             525
CAC TTC CTG ACC TGT GGG CGT TGC CTA AGG GCA TGG CAT TTC ATG GGC 1632
His Phe Leu Thr Cys Gly Arg Cys Leu Arg Ala Trp His Phe Met Gly
    530                 535             540
TGT GGC TGG TGT GGG AAC ATG TGC GGC CAG CAG AAG GAG TGT CCT GGC 1680
Cys Gly Trp Cys Gly Asn Met Cys Gly Gln Gln Lys Glu Cys Pro Gly
545                 550             555                 560
TCC TGG CAA CAG GAC CAC TGC CCA CCT AAG CTT ACT GAG TTC CAC CCC 1728
Ser Trp Gln Gln Asp His Cys Pro Pro Lys Leu Thr Glu Phe His Pro
                565             570                 575
CAC AGT GGA CCT CTA AGG GGC AGT ACA AGG CTG ACC CTG TGT GGC TCC 1776
His Ser Gly Pro Leu Arg Gly Ser Thr Arg Leu Thr Leu Cys Gly Ser
            580             585                 590
AAC TTC TAC CTT CAC CCT TCT GGT CTG GTG CCT GAG GGA ACC CAT CAG 1824
Asn Phe Tyr Leu His Pro Ser Gly Leu Val Pro Glu Gly Thr His Gln
        595             600                 605
GTC ACT GTG GGC CAA AGT CCC TGC CGG CCA CTG CCC AAG GAC AGC TCA 1872
Val Thr Val Gly Gln Ser Pro Cys Arg Pro Leu Pro Lys Asp Ser Ser
    610                 615             620
AAA CTC AGA CCA GTG CCC CGG AAA GAC TTT GTA GAG GAG TTT GAG TGT 1920
Lys Leu Arg Pro Val Pro Arg Lys Asp Phe Val Glu Glu Phe Glu Cys
625             630                 635                 640
```

FIG. 4C-3  Coding Sequence (SEQ ID NO: 7 & 8) cont.

```
GAA CTG GAG CCC TTG GGC ACC CAG GCA GTG GGG CCT ACC AAC GTC AGC   1968
Glu Leu Glu Pro Leu Gly Thr Gln Ala Val Gly Pro Thr Asn Val Ser
            645                     650                 655
CTC ACC GTG ACT AAC ATG CCA CCG GGC AAG CAC TTC CGG GTA GAC GGC   2016
Leu Thr Val Thr Asn Met Pro Pro Gly Lys His Phe Arg Val Asp Gly
        660                 665                 670
ACC TCC GTG CTG AGA GGC TTC TCT TTC ATG GAG CCA GTG CTG ATA GCA   2064
Thr Ser Val Leu Arg Gly Phe Ser Phe Met Glu Pro Val Leu Ile Ala
            675                 680                 685
GTG CAA CCC CTC TTT GGC CCA CGG GCA GGA GGC ACC TGT CTC ACT CTT   2112
Val Gln Pro Leu Phe Gly Pro Arg Ala Gly Gly Thr Cys Leu Thr Leu
        690                 695                 700
GAA GGC CAG AGT CTG TCT GTA GGC ACC AGC CGG GCT GTG CTG GTC AAT   2160
Glu Gly Gln Ser Leu Ser Val Gly Thr Ser Arg Ala Val Leu Val Asn
705                 710                 715                 720
GGG ACT GAG TGT CTG CTA GCA CGG GTC AGT GAG GGG CAG CTT TTA TGT   2208
Gly Thr Glu Cys Leu Leu Ala Arg Val Ser Glu Gly Gln Leu Leu Cys
                    725                 730                 735
GCC ACA CCC CCT GGG GCC ACG GTG GCC AGT GTC CCC CTT AGC CTG CAG   2256
Ala Thr Pro Pro Gly Ala Thr Val Ala Ser Val Pro Leu Ser Leu Gln
            740                 745                 750
GTG GGG GGT GCC CAG GTA CCT GGT TCC TGG ACC TTC CAG TAC AGA GAA   2304
Val Gly Gly Ala Gln Val Pro Gly Ser Trp Thr Phe Gln Tyr Arg Glu
        755                 760                 765
GAC CCT GTC GTG CTA AGC ATC AGC CCC AAC TGT GGC TAC ATC AAC TCC   2352
Asp Pro Val Val Leu Ser Ile Ser Pro Asn Cys Gly Tyr Ile Asn Ser
    770                 775                 780
CAC ATC ACC ATC TGT GGC CAG CAT CTA ACT TCA GCA TGG CAC TTA GTG   2400
His Ile Thr Ile Cys Gly Gln His Leu Thr Ser Ala Trp His Leu Val
785                 790                 795                 800
CTG TCA TTC CAT GAC GGG CTT AGG GCA GTG GAA AGC AGG TGT GAG AGG   2448
Leu Ser Phe His Asp Gly Leu Arg Ala Val Glu Ser Arg Cys Glu Arg
                    805                 810                 815
CAG CTT CCA GAG CAG CAG CTG TGC CGC CTT CCT GAA TAT GTG GTC CGA   2496
Gln Leu Pro Glu Gln Gln Leu Cys Arg Leu Pro Glu Tyr Val Val Arg
            820                 825                 830
GAC CCC CAG GGA TGG GTG GCA GGG AAT CTG AGT GCC CGA GGG GAT GGA   2544
Asp Pro Gln Gly Trp Val Ala Gly Asn Leu Ser Ala Arg Gly Asp Gly
        835                 840                 845
GCT GCT GGC TTT ACA CTG CCT GGC TTT CGC TTC CTA CCC CCA CAT       2592
Ala Ala Gly Phe Thr Leu Pro Gly Phe Arg Phe Leu Pro Pro Pro His
    850                 855                 860
CCA CCC AGT GCC AAC CTA GTT CCA CTG AAG CCT GAG GAG CAT GCC ATT   2640
Pro Pro Ser Ala Asn Leu Val Pro Leu Lys Pro Glu Glu His Ala Ile
865                 870                 875                 880
AAG TTT GAG GTC TGC GTA GAT GCA CTC CCT GCC ATT GAT GGT CTG GAT   2688
Lys Phe Glu Val Cys Val Asp Ala Leu Pro Ala Ile Asp Gly Leu Asp
                    885                 890                 895
TCC ACC ACT TGT GTC CAT GGA GCA TCC TTC TCC GAT AGT GAA GAT GAA   2736
Ser Thr Thr Cys Val His Gly Ala Ser Phe Ser Asp Ser Glu Asp Glu
            900                 905                 910
TCC TGT GTG CCA CTG CTG CGG AAA GAG TCC ATC CAG CTA AGG GAC CTG   2784
Ser Cys Val Pro Leu Leu Arg Lys Glu Ser Ile Gln Leu Arg Asp Leu
        915                 920                 925
GAC TCT GCG CTC TTG GCT GAG GTC AAG GAT GTG CTG ATT CCC CAT GAG   2832
Asp Ser Ala Leu Leu Ala Glu Val Lys Asp Val Leu Ile Pro His Glu
    930                 935                 940
CGG GTG GTC ACC CAC AGT GAC CGA GTC ATT GGC AAA GGC CAC TTT GGA   2880
Arg Val Val Thr His Ser Asp Arg Val Ile Gly Lys Gly His Phe Gly
945                 950                 955                 960
```

FIG. 4C-4   Coding Sequence (SEQ ID NO: 7 & 8) cont.

```
GTT GTC TAC CAC GGA GAA TAC ATA GAC CAG GCC CAG AAT CGA ATC CAA 2928
Val Val Tyr His Gly Glu Tyr Ile Asp Gln Ala Gln Asn Arg Ile Gln
            965             970             975
TGT GCC ATC AAG TCA CTA AGT CGC ATC ACA GAG ATG CAG CAG GTG GAG 2976
Cys Ala Ile Lys Ser Leu Ser Arg Ile Thr Glu Met Gln Gln Val Glu
        980             985             990
GCC TTC CTG CGA GAG GGG CTG CTC ATG CGT GGC CTG AAC CAC CCG AAT 3024
Ala Phe Leu Arg Glu Gly Leu Leu Met Arg Gly Leu Asn His Pro Asn
            995             1000            1005
GTG CTG GCT CTC ATT GGT ATC ATG TTG CCA CCT GAG GGC CTG CCC CAT 3072
Val Leu Ala Leu Ile Gly Ile Met Leu Pro Pro Glu Gly Leu Pro His
    1010            1015            1020
GTG CTG CTG CCC TAT ATG TGC CAC GGT GAC CTG CTC CAG TTC ATC CGC 3120
Val Leu Leu Pro Tyr Met Cys His Gly Asp Leu Leu Gln Phe Ile Arg
1025            1030            1035            1040
TCA CCT CAG CGG AAC CCC ACC GTG AAG GAC CTC ATC AGC TTT GGC CTG 3168
Ser Pro Gln Arg Asn Pro Thr Val Lys Asp Leu Ile Ser Phe Gly Leu
            1045            1050            1055
CAG GTA GCC CGC GGC ATG GAG TAC CTG GCA GAG CAG AAG TTT GTG CAC 3216
Gln Val Ala Arg Gly Met Glu Tyr Leu Ala Glu Gln Lys Phe Val His
            1060            1065            1070
AGG GAC CTG GCT GCG CGG AAC TGC ATG CTG GAC GAG TCA TTC ACA GTC 3264
Arg Asp Leu Ala Ala Arg Asn Cys Met Leu Asp Glu Ser Phe Thr Val
        1075            1080            1085
AAG GTG GCT GAC TTT GGT TTG GCC CGC GAC ATC CTG GAC AGG GAG TAC 3312
Lys Val Ala Asp Phe Gly Leu Ala Arg Asp Ile Leu Asp Arg Glu Tyr
    1090            1095            1100
TAT AGT GTT CAA CAG CAT CGC CAC GCT CGC CTA CCT GTG AAG TGG ATG 3360
Tyr Ser Val Gln Gln His Arg His Ala Arg Leu Pro Val Lys Trp Met
1105            1110            1115            1120
GCG CTG GAG AGC CTG CAG ACC TAT AGA TTT ACC ACC AAG TCT GAT GTG 3408
Ala Leu Glu Ser Leu Gln Thr Tyr Arg Phe Thr Thr Lys Ser Asp Val
            1125            1130            1135
GTA CCA AGT GAT GCA GCA ATG CTG GGA GGC AGA CCC AGC AGT GCG ACC 3456
Val Pro Ser Asp Ala Ala Met Leu Gly Gly Arg Pro Ser Ser Ala Thr
            1140            1145            1150
CAC CTT CAG AGT ACT AGT GGG GGA GGT GGA GCA GAT AGT GTC TGC ACT 3504
His Leu Gln Ser Thr Ser Gly Gly Gly Gly Ala Asp Ser Val Cys Thr
        1155            1160            1165
GCT TGG GGA CCA TTA TGT GCA GCT GCC AGC AAC CTA CAT GAA CTT GAG 3552
Ala Trp Gly Pro Leu Cys Ala Ala Ala Ser Asn Leu His Glu Leu Glu
    1170            1175            1180
CTA ACC CCA AGG CTG CCT CTG GGC CAT GCC AGG CCA GAG CAG TGG CCC 3600
Leu Thr Pro Arg Leu Pro Leu Gly His Ala Arg Pro Glu Gln Trp Pro
1185            1190            1195            1200
TCC ACC TTG TTC CTG CCC TTT AAC TTT CAG AGG CAA                 3636
Ser Thr Leu Phe Leu Pro Phe Asn Phe Gln Arg Gln
            1205            1210
```

FIG. 5-1    SEQ ID NOs: 2, 4, 6, 8

```
Ron-V3  GGATCCTCTAGGGTC CCAGCTCGCCTCGAT GGAGCTCCTCCCGCC GCTGCCTCAGTCCTT CCTGTTGCTGCTGCT GTTGCCTGCCAAGCC   90
Ron-V2  GGATCCTCTAGGGTC CCAGCTCGCCTCGAT GGAGCTCCTCCCGCC GCTGCCTCAGTCCTT CCTGTTGCTGCTGCT GTTGCCTGCCAAGCC   90
Ron-V1  GGATCCTCTAGGGTC CCAGCTCGCCTCGAT GGAGCTCCTCCCGCC GCTGCCTCAGTCCTT CCTGTTGCTGCTGCT GTTGCCTGCCAAGCC   90
Ron     GGATCCTCTAGGGTC CCAGCTCGCCTCGAT GGAGCTCCTCCCGCC GCTGCCTCAGTCCTT CCTGTTGCTGCTGCT GTTGCCTGCCAAGCC   90

Ron-V3  CGCGGCGGGCGAGGA CTGGCAGTGCCCGCG CACCCCCTACGCGGC CTCTCGCGACTTTGA CGTGAAGTACGTGGT GCCCAGCTTCTCCGC  180
Ron-V2  CGCGGCGGGCGAGGA CTGGCAGTGCCCGCG CACCCCCTACGCGGC CTCTCGCGACTTTGA CGTGAAGTACGTGGT GCCCAGCTTCTCCGC  180
Ron-V1  CGCGGCGGGCGAGGA CTGGCAGTGCCCGCG CACCCCCTACGCGGC CTCTCGCGACTTTGA CGTGAAGTACGTGGT GCCCAGCTTCTCCGC  180
Ron     CGCGGCGGGCGAGGA CTGGCAGTGCCCGCG CACCCCCTACGCGGC CTCTCGCGACTTTGA CGTGAAGTACGTGGT GCCCAGCTTCTCCGC  180

Ron-V3  CGGAGGCCTGGTACA GGCCATGGTGACCTA CGAGGGCGACAGAAA TGAGAGTGCTGTGTT TGTAGCCATACGCAA TCGCCTGCATGTGCT  270
Ron-V2  CGGAGGCCTGGTACA GGCCATGGTGACCTA CGAGGGCGACAGAAA TGAGAGTGCTGTGTT TGTAGCCATACGCAA TCGCCTGCATGTGCT  270
Ron-V1  CGGAGGCCTGGTACA GGCCATGGTGACCTA CGAGGGCGACAGAAA TGAGAGTGCTGTGTT TGTAGCCATACGCAA TCGCCTGCATGTGCT  270
Ron     CGGAGGCCTGGTACA GGCCATGGTGACCTA CGAGGGCGACAGAAA TGAGAGTGCTGTGTT TGTAGCCATACGCAA TCGCCTGCATGTGCT  270

Ron-V3  TGGGCCTGACCTGAA GTCTGTCCAGAGCCT GGCCACGGGCCCTGC TGGAGACCCTGGCTG CCAGACGTGTGCAGC CTGTGGCCCAGGACC  360
Ron-V2  TGGGCCTGACCTGAA GTCTGTCCAGAGCCT GGCCACGGGCCCTGC TGGAGACCCTGGCTG CCAGACGTGTGCAGC CTGTGGCCCAGGACC  360
Ron-V1  TGGGCCTGACCTGAA GTCTGTCCAGAGCCT GGCCACGGGCCCTGC TGGAGACCCTGGCTG CCAGACGTGTGCAGC CTGTGGCCCAGGACC  360
Ron     TGGGCCTGACCTGAA GTCTGTCCAGAGCCT GGCCACGGGCCCTGC TGGAGACCCTGGCTG CCAGACGTGTGCAGC CTGTGGCCCAGGACC  360

Ron-V3  CCACGGCCCTCCCGG TGACACAGACACAAA GGTGCTGGTGCTGGA TCCCGCGCTGCCTGC GCTGGTCAGTTGTGG CTCCAGCCTGCAGGG  450
Ron-V2  CCACGGCCCTCCCGG TGACACAGACACAAA GGTGCTGGTGCTGGA TCCCGCGCTGCCTGC GCTGGTCAGTTGTGG CTCCAGCCTGCAGGG  450
Ron-V1  CCACGGCCCTCCCGG TGACACAGACACAAA GGTGCTGGTGCTGGA TCCCGCGCTGCCTGC GCTGGTCAGTTGTGG CTCCAGCCTGCAGGG  450
Ron     CCACGGCCCTCCCGG TGACACAGACACAAA GGTGCTGGTGCTGGA TCCCGCGCTGCCTGC GCTGGTCAGTTGTGG CTCCAGCCTGCAGGG  450
```

FIG. 5-2    SEQ ID NOs: 2, 4, 6, 8 cont.

```
Ron-V3   CCGCTGCTTCCTGCA TGACCTAGAGCCCCA AGGGACAGCCGTGCA TCTGGCAGCGCCAGC CTGCCTCTTCTCAGC CCACCATAACCGGCC   540
Ron-V2   CCGCTGCTTCCTGCA TGACCTAGAGCCCCA AGGGACAGCCGTGCA TCTGGCAGCGCCAGC CTGCCTCTTCTCAGC CCACCATAACCGGCC   540
Ron-V1   CCGCTGCTTCCTGCA TGACCTAGAGCCCCA AGGGACAGCCGTGCA TCTGGCAGCGCCAGC CTGCCTCTTCTCAGC CCACCATAACCGGCC   540
Ron      CCGCTGCTTCCTGCA TGACCTAGAGCCCCA AGGGACAGCCGTGCA TCTGGCAGCGCCAGC CTGCCTCTTCTCAGC CCACCATAACCGGCC   540

Ron-V3   CGATGACTGCCCCGA CTGTGTGGCCAGCCC ATTGGGCACCCGTGT AACTGTGGTTGAGCA AGGCCAGGCCTCCTA TTTCTACGTGGCATC   630
Ron-V2   CGATGACTGCCCCGA CTGTGTGGCCAGCCC ATTGGGCACCCGTGT AACTGTGGTTGAGCA AGGCCAGGCCTCCTA TTTCTACGTGGCATC   630
Ron-V1   CGATGACTGCCCCGA CTGTGTGGCCAGCCC ATTGGGCACCCGTGT AACTGTGGTTGAGCA AGGCCAGGCCTCCTA TTTCTACGTGGCATC   630
Ron      CGATGACTGCCCCGA CTGTGTGGCCAGCCC ATTGGGCACCCGTGT AACTGTGGTTGAGCA AGGCCAGGCCTCCTA TTTCTACGTGGCATC   630

Ron-V3   CTCACTGGACGCAGC CGTGGCTGGCAGCTT CAGCCCACGCTCAGT GTCTATCAGGCGTCT CAAGGCTGACGCCTC GGGATTCGCACCGGG   720
Ron-V2   CTCACTGGACGCAGC CGTGGCTGGCAGCTT CAGCCCACGCTCAGT GTCTATCAGGCGTCT CAAGGCTGACGCCTC GGGATTCGCACCGGG   720
Ron-V1   CTCACTGGACGCAGC CGTGGCTGGCAGCTT CAGCCCACGCTCAGT GTCTATCAGGCGTCT CAAGGCTGACGCCTC GGGATTCGCACCGGG   720
Ron      CTCACTGGACGCAGC CGTGGCTGGCAGCTT CAGCCCACGCTCAGT GTCTATCAGGCGTCT CAAGGCTGACGCCTC GGGATTCGCACCGGG   720

Ron-V3   CTTTGTGGCGTTGTC AGTGCTGCCCAAGCA TCTTGTCTCCTACAG TATTGAATACGTGCA CAGCTTCCACACGGG AGCCTTCGTATACTT   810
Ron-V2   CTTTGTGGCGTTGTC AGTGCTGCCCAAGCA TCTTGTCTCCTACAG TATTGAATACGTGCA CAGCTTCCACACGGG AGCCTTCGTATACTT   810
Ron-V1   CTTTGTGGCGTTGTC AGTGCTGCCCAAGCA TCTTGTCTCCTACAG TATTGAATACGTGCA CAGCTTCCACACGGG AGCCTTCGTATACTT   810
Ron      CTTTGTGGCGTTGTC AGTGCTGCCCAAGCA TCTTGTCTCCTACAG TATTGAATACGTGCA CAGCTTCCACACGGG AGCCTTCGTATACTT   810

Ron-V3   CCTGACTGTACAGCC GGCCAGCGTGACAGA TGATCCTAGTGCCCT GCACACAGCCTGGC ACGGCTTAGCGCCAC TGAGCCAGAGTTGGG    900
Ron-V2   CCTGACTGTACAGCC GGCCAGCGTGACAGA TGATCCTAGTGCCCT GCACACAGCCTGGC ACGGCTTAGCGCCAC TGAGCCAGAGTTGGG    900
Ron-V1   CCTGACTGTACAGCC GGCCAGCGTGACAGA TGATCCTAGTGCCCT GCACACAGCCTGGC ACGGCTTAGCGCCAC TGAGCCAGAGTTGGG    900
Ron      CCTGACTGTACAGCC GGCCAGCGTGACAGA TGATCCTAGTGCCCT GCACACAGCCTGGC ACGGCTTAGCGCCAC TGAGCCAGAGTTGGG    900
```

FIG. 5-3    SEQ ID NOs: 2, 4, 6, 8 cont.

```
Ron-V3  TGACTATCGGGAGCT GGTCCTCGACTGCAG ATTTGCTCCAAAACG CAGGCGCCGGGGGC CCCAGAAGGCGGACA GCCCTACCCTGTGCT    990
Ron-V2  TGACTATCGGGAGCT GGTCCTCGACTGCAG ATTTGCTCCAAAACG CAGGCGCCGGGGGC CCCAGAAGGCGGACA GCCCTACCCTGTGCT    990
Ron-V1  TGACTATCGGGAGCT GGTCCTCGACTGCAG ATTTGCTCCAAAACG CAGGCGCCGGGGGC CCCAGAAGGCGGACA GCCCTACCCTGTGCT    990
Ron     TGACTATCGGGAGCT GGTCCTCGACTGCAG ATTTGCTCCAAAACG CAGGCGCCGGGGGGC CCCAGAAGGCGGACA GCCCTACCCTGTGCT   990

Ron-V3  GCAGGTGGCCCACTC CGCTCCAGTGGGTGC CCAACTTGCCACTGA GCTGAGCATCGCCGA GGGCCAGGAAGTACT ATTTGGGTCTTTGT    1080
Ron-V2  GCAGGTGGCCCACTC CGCTCCAGTGGGTGC CCAACTTGCCACTGA GCTGAGCATCGCCGA GGGCCAGGAAGTACT ATTTGGGTCTTTGT    1080
Ron-V1  GCAGGTGGCCCACTC CGCTCCAGTGGGTGC CCAACTTGCCACTGA GCTGAGCATCGCCGA GGGCCAGGAAGTACT ATTTGGGTCTTTGT    1080
Ron     GCAGGTGGCCCACTC CGCTCCAGTGGGTGC CCAACTTGCCACTGA GCTGAGCATCGCCGA GGGCCAGGAAGTACT ATTTGGGTCTTTGT    1080

Ron-V3  GACTGGCAAGGATGG TGGTCCTGGCGTGGG CCCCAACTCTGTCGT CTGTGCCTTCCCCAT TGACCTGCTGGACAC ACTAATTGATGAGGG    1170
Ron-V2  GACTGGCAAGGATGG TGGTCCTGGCGTGGG CCCCAACTCTGTCGT CTGTGCCTTCCCCAT TGACCTGCTGGACAC ACTAATTGATGAGGG    1170
Ron-V1  GACTGGCAAGGATGG TGGTCCTGGCGTGGG CCCCAACTCTGTCGT CTGTGCCTTCCCCAT TGACCTGCTGGACAC ACTAATTGATGAGGG    1170
Ron     GACTGGCAAGGATGG TGGTCCTGGCGTGGG CCCCAACTCTGTCGT CTGTGCCTTCCCCAT TGACCTGCTGGACAC ACTAATTGATGAGGG    1170

Ron-V3  TGTGGAGCGCTGTTG TGAATCCCAGTCCA TCCAGGCCTCCGGCG AGGCCTCGACTTCTT CCAGTCGCCCAGTTT TTGCCCCAACCCGCC    1260
Ron-V2  TGTGGAGCGCTGTTG TGAATCCCAGTCCA TCCAGGCCTCCGGCG AGGCCTCGACTTCTT CCAGTCGCCCAGTTT TTGCCCCAACCCGCC    1260
Ron-V1  TGTGGAGCGCTGTTG TGAATCCCAGTCCA TCCAGGCCTCCGGCG AGGCCTCGACTTCTT CCAGTCGCCCAGTTT TTGCCCCAACCCGCC    1260
Ron     TGTGGAGCGCTGTTG TGAATCCCAGTCCA TCCAGGCCTCCGGCG AGGCCTCGACTTCTT CCAGTCGCCCAGTTT TTGCCCCAACCCGCC    1260

Ron-V3  TGGCCTGGAAGCCCT CAGCCCCAACACCAG CTGCCGCCACTTCCC TCTGCTGGTCAGTAG CAGCTTCTCACGTGT GGACCTATTCAATGG    1350
Ron-V2  TGGCCTGGAAGCCCT CAGCCCCAACACCAG CTGCCGCCACTTCCC TCTGCTGGTCAGTAG CAGCTTCTCACGTGT GGACCTATTCAATGG    1350
Ron-V1  TGGCCTGGAAGCCCT CAGCCCCAACACCAG CTGCCGCCACTTCCC TCTGCTGGTCAGTAG CAGCTTCTCACGTGT GGACCTATTCAATGG    1350
Ron     TGGCCTGGAAGCCCT CAGCCCCAACACCAG CTGCCGCCACTTCCC TCTGCTGGTCAGTGT CAGCTTCTCACGTGT GGACCTATTCAATGG    1350
```

FIG. 5-4    SEQ ID NOs: 2, 4, 6, 8 cont.

```
Ron-V3   GCTGTTGGGACCAGT ACAGGTCACTGCATT GTATGTGACACGCCT TGACAACGTCACAGT GGCACACATGGGCAC AATGGATGGGCGTAT   1440
Ron-V2   GCTGTTGGGACCAGT ACAGGTCACTGCATT GTATGTGACACGCCT TGACAACGTCACAGT GGCACACATGGGCAC AATGGATGGGCGTAT   1440
Ron-V1   GCTGTTGGGACCAGT ACAGGTCACTGCATT GTATGTGACACGCCT TGACAACGTCACAGT GGCACACATGGGCAC AATGGATGGGCGTAT   1440
Ron      GCTGTTGGGACCAGT ACAGGTCACTGCATT GTATGTGACACGCCT TGACAACGTCACAGT GGCACACATGGGCAC AATGGATGGGCGTAT   1440

Ron-V3   CCTGCAGGTGGAGCT GGTCAGGTCACTAAA CTACTTGCTGTATGT GTCCAACTTCTCACT GGGTGACAGTGGGCA GCCCGTGCAGCGGGA   1530
Ron-V2   CCTGCAGGTGGAGCT GGTCAGGTCACTAAA CTACTTGCTGTATGT GTCCAACTTCTCACT GGGTGACAGTGGGCA GCCCGTGCAGCGGGA   1530
Ron-V1   CCTGCAGGTGGAGCT GGTCAGGTCACTAAA CTACTTGCTGTATGT GTCCAACTTCTCACT GGGTGACAGTGGGCA GCCCGTGCAGCGGGA   1530
Ron      CCTGCAGGTGGAGCT GGTCAGGTCACTAAA CTACTTGCTGTATGT GTCCAACTTCTCACT GGGTGACAGTGGGCA GCCCGTGCAGCGGGA   1530

Ron-V3   TGTCAGTCGTCTTGG GGACCACCTACTCTT TGCCTCTGGGGACCA GGTTTTCCAGGTACC TATCCGAGGCCCTGG CTGCCGCCACTTCCT   1620
Ron-V2   TGTCAGTCGTCTTGG GGACCACCTACTCTT TGCCTCTGGGGACCA GGTTTTCCAGGTACC TATCCGAGGCCCTGG CTGCCGCCACTTCCT   1620
Ron-V1   TGTCAGTCGTCTTGG GGACCACCTACTCTT TGCCTCTGGGGACCA GGTTTTCCAGGTACC TATCCGAGGCCCTGG CTGCCGCCACTTCCT   1620
Ron      TGTCAGTCGTCTTGG GGACCACCTACTCTT TGCCTCTGGGGACCA GGTTTTCCAGGTACC TATCCGAGGCCCTGG CTGCCGCCACTTCCT   1620

Ron-V3   GACCTGTGGGCGTTG CCTAAGGGCATGGCA TTTCATGGGCTGTGG CTGGTGTGGGAACAT GTGCGGCCAGCAGAA GGAGTGTCCTGCTC    1710
Ron-V2   GACCTGTGGGCGTTG CCTAAGGGCATGGCA TTTCATGGGCTGTGG CTGGTGTGGGAACAT GTGCGGCCAGCAGAA GGAGTGTCCTGCTC    1710
Ron-V1   GACCTGTGGGCGTTG CCTAAGGGCATGGCA TTTCATGGGCTGTGG CTGGTGTGGGAACAT GTGCGGCCAGCAGAA GGAGTGTCCTGCTC    1710
Ron      GACCTGTGGGCGTTG CCTAAGGGCATGGCA TTTCATGGGCTGTGG CTGGTGTGGGAACAT GTGCGGCCAGCAGAA GGAGTGTCCTGCTC    1710

Ron-V3   CTGGCAACAGGACCA CTGCCCACCTAAGCT TACTGAGTTCCACCC CCACAGTGGACCTCT AAGGGGCAGTACAAG GCTGACCCTGTGTGG   1800
Ron-V2   CTGGCAACAGGACCA CTGCCCACCTAAGCT TACTGAGTTCCACCC CCACAGTGGACCTCT AAGGGGCAGTACAAG GCTGACCCTGTGTGG   1800
Ron-V1   CTGGCAACAGGACCA CTGCCCACCTAAGCT TACTGAGTTCCACCC CCACAGTGGACCTCT AAGGGGCAGTACAAG GCTGACCCTGTGTGG   1800
Ron      CTGGCAACAGGACCA CTGCCCACCTAAGCT TACTGAGTTCCACCC CCACAGTGGACCTCT AAGGGGCAGTACAAG GCTGACCCTGTGTGG   1800
```

FIG. 5-5    SEQ ID NOs: 2, 4, 6, 8 cont.

```
Ron-V3  CTCCAACTTCTACCT TCACCCTTCTGGTCT GGTGCCTGAGGGAAC CCATCAGGTCACTGT GGGCCAAAGTCCCTG CCGGCCACTGCCCAA  1890
Ron-V2  CTCCAACTTCTACCT TCACCCTTCTGGTCT GGTGCCTGAGGGAAC CCATCAGGTCACTGT GGGCCAAAGTCCCTG CCGGCCACTGCCCAA  1890
Ron-V1  CTCCAACTTCTACCT TCACCCTTCTGGTCT GGTGCCTGAGGGAAC CCATCAGGTCACTGT GGGCCAAAGTCCCTG CCGGCCACTGCCCAA  1890
Ron     CTCCAACTTCTACCT TCACCCTTCTGGTCT GGTGCCTGAGGGAAC CCATCAGGTCACTGT GGGCCAAAGTCCCTG CCGGCCACTGCCCAA  1890

Ron-V3  GGACAGCTCAAAACT CAGACCAGTGCCCCG GAAAGACTTTGTAGA GGAGTTTGAGTGTGA ACTGGAGCCCTTGGG CACCCAGGCAGTGGG  1980
Ron-V2  GGACAGCTCAAAACT CAGACCAGTGCCCCG GAAAGACTTTGTAGA GGAGTTTGAGTGTGA ACTGGAGCCCTTGGG CACCCAGGCAGTGGG  1980
Ron-V1  GGACAGCTCAAAACT CAGACCAGTGCCCCG GAAAGACTTTGTAGA GGAGTTTGAGTGTGA ACTGGAGCCCTTGGG CACCCAGGCAGTGGG  1980
Ron     GGACAGCTCAAAACT CAGACCAGTGCCCCG GAAAGACTTTGTAGA GGAGTTTGAGTGTGA ACTGGAGCCCTTGGG CACCCAGGCAGTGGG  1980

Ron-V3  GCCTACCAACGTCAG CCTCACCGTGACTAA CATGCCACCGGGCAA GCACTTCCGGGTAGA CGGCACCTCCGTGCT GAGAGGCTTCTCTTT  2070
Ron-V2  GCCTACCAACGTCAG CCTCACCGTGACTAA CATGCCACCGGGCAA GCACTTCCGGGTAGA CGGCACCTCCGTGCT GAGAGGCTTCTCTTT  2070
Ron-V1  GCCTACCAACGTCAG CCTCACCGTGACTAA CATGCCACCGGGCAA GCACTTCCGGGTAGA CGGCACCTCCGTGCT GAGAGGCTTCTCTTT  2070
Ron     GCCTACCAACGTCAG CCTCACCGTGACTAA CATGCCACCGGGCAA GCACTTCCGGGTAGA CGGCACCTCCGTGCT GAGAGGCTTCTCTTT  2070

Ron-V3  CATGGAGCCAGTGCT GATAGCAGTGCAACC CCTCTTTGGCCCACG GGCAGGAGGCACCTG TCTCACTCTTGAAGG CCAGAGTCTGTCTGT  2160
Ron-V2  CATGGAGCCAGTGCT GATAGCAGTGCAACC CCTCTTTGGCCCACG GGCAGGAGGCACCTG TCTCACTCTTGAAGG CCAGAGTCTGTCTGT  2160
Ron-V1  CATGGAGCCAGTGCT GATAGCAGTGCAACC CCTCTTTGGCCCACG GGCAGGAGGCACCTG TCTCACTCTTGAAGG CCAGAGTCTGTCTGT  2160
Ron     CATGGAGCCAGTGCT GATAGCAGTGCAACC CCTCTTTGGCCCACG GGCAGGAGGCACCTG TCTCACTCTTGAAGG CCAGAGTCTGTCTGT  2160

Ron-V3  AGGCACCAGCCGGGC TGTGCTGGTCAATGG GACTGAGTGTCTGCT AGCACGGGTCAGTGA GGGGCAGCTTTTATG TGCCACACCCCCTGG  2250
Ron-V2  AGGCACCAGCCGGGC TGTGCTGGTCAATGG GACTGAGTGTCTGCT AGCACGGGTCAGTGA GGGGCAGCTTTTATG TGCCACACCCCCTGG  2250
Ron-V1  AGGCACCAGCCGGGC TGTGCTGGTCAATGG GACTGAGTGTCTGCT AGCACGGGTCAGTGA GGGGCAGCTTTTATG TGCCACACCCCCTGG  2250
Ron     AGGCACCAGCCGGGC TGTGCTGGTCAATGG GACTGAGTGTCTGCT AGCACGGGTCAGTGA GGGGCAGCTTTTATG TGCCACACCCCCTGG  2250
```

FIG. 5-6   SEQ ID NOs: 2, 4, 6, 8 cont.

```
Ron-V3  GGCCACGGTGGCCAG TGTCCCCCTTAGCCT GCAGGTGGGGGGTGC CCAGGTACCTGGTTC CTGGACCTTCCAGTA CAGAGAAGACCCTGT  2340
Ron-V2  GGCCACGGTGGCCAG TGTCCCCCTTAGCCT GCAGGTGGGGGGTGC CCAGGTACCTGGTTC CTGGACCTTCCAGTA CAGAGAAGACCCTGT  2340
Ron-V1  GGCCACGGTGGCCAG TGTCCCCCTTAGCCT GCAGGTGGGGGGTGC CCAGGTACCTGGTTC CTGGACCTTCCAGTA CAGAGAAGACCCTGT  2340
Ron     GGCCACGGTGGCCAG TGTCCCCCTTAGCCT GCAGGTGGGGGGTGC CCAGGTACCTGGTTC CTGGACCTTCCAGTA CAGAGAAGACCCTGT  2340

Ron-V3  CGTGCTAAGCATCAG CCCCAACTGTGGCTA CATCAACTCCCACAT CACCATCTGTGGCCA GCATCTAACTTCAGC ATGGCACTTAGTGCT  2430
Ron-V2  CGTGCTAAGCATCAG CCCCAACTGTGGCTA CATCAACTCCCACAT CACCATCTGTGGCCA GCATCTAACTTCAGC ATGGCACTTAGTGCT  2430
Ron-V1  CGTGCTAAGCATCAG CCCCAACTGTGGCTA CATCAACTCCCACAT CACCATCTGTGGCCA GCATCTAACTTCAGC ATGGCACTTAGTGCT  2430
Ron     CGTGCTAAGCATCAG CCCCAACTGTGGCTA CATCAACTCCCACAT CACCATCTGTGGCCA GCATCTAACTTCAGC ATGGCACTTAGTGCT  2430

Ron-V3  GTCATTCCATGACGG GCTTAGGGCAGTGGA AAGCAGGTGTGAGAG GCAGCTTCCAGAGCA GCAGCTGTGCCGCCT TCCTGAATATGTGGT  2520
Ron-V2  GTCATTCCATGACGG GCTTAGGGCAGTGGA AAGCAGGTGTGAGAG GCAGCTTCCAGAGCA GCAGCTGTGCCGCCT TCCTGAATATGTGGT  2520
Ron-V1  GTCATTCCATGACGG GCTTAGGGCAGTGGA AAGCAGGTGTGAGAG GCAGCTTCCAGAGCA GCAGCTGTGCCGCCT TCCTGAATATGTGGT  2520
Ron     GTCATTCCATGACGG GCTTAGGGCAGTGGA AAGCAGGTGTGAGAG GCAGCTTCCAGAGCA GCAGCTGTGCCGCCT TCCTGAATATGTGGT  2520

Ron-V3  CCGAGACCCCCAGGG ATGGGTGGCAGGGAA TCTGAGTGCCCGAGG GGATGGAGCTGCTGG CTTTACACTGCCTGG CTTTCGCTTCCTACC  2610
Ron-V2  CCGAGACCCCCAGGG ATGGGTGGCAGGGAA TCTGAGTGCCCGAGG GGATGGAGCTGCTGG CTTTACACTGCCTGG CTTTCGCTTCCTACC  2610
Ron-V1  CCGAGACCCCCAGGG ATGGGTGGCAGGGAA TCTGAGTGCCCGAGG GGATGGAGCTGCTGG CTTTACACTGCCTGG CTTTCGCTTCCTACC  2610
Ron     CCGAGACCCCCAGGG ATGGGTGGCAGGGAA TCTGAGTGCCCGAGG GGATGGAGCTGCTGG CTTTACACTGCCTGG CTTTCGCTTCCTACC  2610

Ron-V3  CCCACCCCATCCACC CAGTGCCAACCTAGT TCCACTGAAGCCTGA GGAGCATGCCATTAA GTTTGAG--------  ---------------  2690
Ron-V2  CCCACCCCATCCACC CAGTGCCAACCTAGT TCCACTGAAGCCTGA GGAGCATGCCATTAA GTTTGAG--------  ---------------  2677
Ron-V1  CCCACCCCATCCACC CAGTGCCAACCTAGT TCCACTGAAGCCTGA GGAGCATGCCATTAA GTTTGAGTATATTGG GCTGGGCGCTGTGGC  2700
Ron     CCCACCCCATCCACC CAGTGCCAACCTAGT TCCACTGAAGCCTGA GGAGCATGCCATTAA GTTTGAGTATATTGG GCTGGGCGCTGTGGC  2700
```

FIG. 5-7  SEQ ID NOs: 2, 4, 6, 8 cont.

```
Ron-V3  ------------  ------------  ------------  ------------  ------------  ------------                                          2690
Ron-V2  ------------  ------------  ------------  ------------  ------------  CCCCCTGCCCCATC                                         2677
Ron-V1  TGACTGTGTGGGTAT CAACGTGACCGTGGG TGGTGAGAGCTGCCA GCACGAGTTCCGGGG GGACATGGTTGTCTG CCCCCTGCCCCATC                                2790
Ron     TGACTGTGTGGGTAT CAACGTGACCGTGGG TGGTGAGAGCTGCCA GCACGAGTTCCGGGG GGACATGGTTGTCTG CCCCCTGCCCCATC                                2790

Ron-V3  ------------  ------------  ----GTCTGCGTAGA TG----------                                                                     2690
Ron-V2  ------CTTGGCCA GGATGTGCCCCATT GCAGGTCTCGCGTAGA TG----------                                                                   2717
Ron-V1  CCTGCAGCTTGGCCA GGATGTGCCCCATT GCAGGTCTCGCGTAGA TG----------                                                                   2837
Ron     CCTGCAGCTTGGCCA GGATGTGCCCCATT GCAGGTCTCGCGTAGA TGGTGAATGTCATAT CCTGGGTAGAGTGGT GCGGCCAGGGCCAGA                                2880

Ron-V3  ------------  ------------  ------------  ------------  ------------  ------------                                          2690
Ron-V2  ------------  ------------  ------------  ------------  ------------  ------------                                          2717
Ron-V1  ------------  ------------  ------------  ------------  ------------  ------------                                          2837
Ron     TGGGGTCCCACAGAG CACGCTCCTTGGTAT CCTGCTGCCTTTGCT GCTGCTTGTGGCTGC ACTGGCGACTGCACT GGTCTTCAGCTACTG                                2970

Ron-V3  ------------  ------------  ------------  ------------  ------------  ------------                                          2690
Ron-V2  ------------  ------------  ------------  ------------  ------------  ------------                                          2717
Ron-V1  ------------  ------------  ------------  ------------  ------------  ------------                                          2837
Ron     GTGGCGGAGGAAGCA GCTAGTTCTTCCTCC CAACCTGAATGACCT GGCATCCCTGGACCA GACTGCTGGAGCCAC ACCCCTGCCTATTCT                                3060

Ron-V3  ------------  --CACTCCCTGCCAT TGATGGTCTGGATTC CACCACTTGTGTCCA TGGAGCATCCTTCTC                                                  2748
Ron-V2  ------------  --CACTCCCTGCCAT TGATGGTCTGGATTC CACCACTTGTGTCCA TGGAGCATCCTTCTC                                                  2775
Ron-V1  ------------  --CACTCCCTGCCAT TGATGGTCTGGATTC CACCACTTGTGTCCA TGGAGCATCCTTCTC                                                  2895
Ron     GTACTCGGGCTCTGA CTACAGAAGTGGCCT TGCACTCCCTGCCAT TGATGGTCTGGATTC CACCACTTGTGTCCA TGGAGCATCCTTCTC                                3150
```

FIG. 5-8    SEQ ID NOs: 2, 4, 6, 8 cont.

```
Ron-V3  CGATAGTGAAGATGA ATCCTGTGTGCCACT GCTGCGGAAAGAGTC CATCCAGCTAAGGGA CCTGGACTCTGCGCT CTTGGCTGAGGTCAA  2838
Ron-V2  CGATAGTGAAGATGA ATCCTGTGTGCCACT GCTGCGGAAAGAGTC CATCCAGCTAAGGGA CCTGGACTCTGCGCT CTTGGCTGAGGTCAA  2865
Ron-V1  CGATAGTGAAGATGA ATCCTGTGTGCCACT GCTGCGGAAAGAGTC CATCCAGCTAAGGGA CCTGGACTCTGCGCT CTTGGCTGAGGTCAA  2985
Ron     CGATAGTGAAGATGA ATCCTGTGTGCCACT GCTGCGGAAAGAGTC CATCCAGCTAAGGGA CCTGGACTCTGCGCT CTTGGCTGAGGTCAA  3240

Ron-V3  GGATGTGCTGATTCC CCATGAGCGGGTGGT CACCCACAGTGACCG AGTCATTGGCAAAGG CCACTTTGGAGTTGT CTACCACGGAGAATA  2928
Ron-V2  GGATGTGCTGATTCC CCATGAGCGGGTGGT CACCCACAGTGACCG AGTCATTGGCAAAGG CCACTTTGGAGTTGT CTACCACGGAGAATA  2955
Ron-V1  GGATGTGCTGATTCC CCATGAGCGGGTGGT CACCCACAGTGACCG AGTCATTGGCAAAGG CCACTTTGGAGTTGT CTACCACGGAGAATA  3075
Ron     GGATGTGCTGATTCC CCATGAGCGGGTGGT CACCCACAGTGACCG AGTCATTGGCAAAGG CCACTTTGGAGTTGT CTACCACGGAGAATA  3330

Ron-V3  CATAGACCAGGCCCA GAATCGAATCCAATG TGCCATCAAGTCACT AAGTCGCATCACAGA GATGCAGCAGGTGGA GGCCTTCCTGCGAGA  3018
Ron-V2  CATAGACCAGGCCCA GAATCGAATCCAATG TGCCATCAAGTCACT AAGTCGCATCACAGA GATGCAGCAGGTGGA GGCCTTCCTGCGAGA  3045
Ron-V1  CATAGACCAGGCCCA GAATCGAATCCAATG TGCCATCAAGTCACT AAGTCGCATCACAGA GATGCAGCAGGTGGA GGCCTTCCTGCGAGA  3165
Ron     CATAGACCAGGCCCA GAATCGAATCCAATG TGCCATCAAGTCACT AAGTCGCATCACAGA GATGCAGCAGGTGGA GGCCTTCCTGCGAGA  3420

Ron-V3  GGGGCTGCTCATGCG TGGCCTGAACCACCC GAATGTGCTGGCTCT CATTGGTATCATGTT GCCACCTGAGGGCCT GCCCCATGTGCTGCT  3108
Ron-V2  GGGGCTGCTCATGCG TGGCCTGAACCACCC GAATGTGCTGGCTCT CATTGGTATCATGTT GCCACCTGAGGGCCT GCCCCATGTGCTGCT  3135
Ron-V1  GGGGCTGCTCATGCG TGGCCTGAACCACCC GAATGTGCTGGCTCT CATTGGTATCATGTT GCCACCTGAGGGCCT GCCCCATGTGCTGCT  3255
Ron     GGGGCTGCTCATGCG TGGCCTGAACCACCC GAATGTGCTGGCTCT CATTGGTATCATGTT GCCACCTGAGGGCCT GCCCCATGTGCTGCT  3510

Ron-V3  GCCCTATATGTGCCA CGGTGACCTGCTCCA GTTCATCCGCTCACC TCAGCGGAACCCCAC CGTGAAGGACCTCAT CAGCTTTGGCCTGCA  3198
Ron-V2  GCCCTATATGTGCCA CGGTGACCTGCTCCA GTTCATCCGCTCACC TCAGCGGAACCCCAC CGTGAAGGACCTCAT CAGCTTTGGCCTGCA  3225
Ron-V1  GCCCTATATGTGCCA CGGTGACCTGCTCCA GTTCATCCGCTCACC TCAGCGGAACCCCAC CGTGAAGGACCTCAT CAGCTTTGGCCTGCA  3345
Ron     GCCCTATATGTGCCA CGGTGACCTGCTCCA GTTCATCCGCTCACC TCAGCGGAACCCCAC CGTGAAGGACCTCAT CAGCTTTGGCCTGCA  3600
```

FIG. 5-9    SEQ ID NOs: 2, 4, 6, 8 cont.

| | | | | | | | | |
|---|---|---|---|---|---|---|---|---|
| Ron-V3 | GGTAGCCCGCGGCAT | GGAGTACCTGGCAGA | GCAGAAGTTTGTGCA | CAGGGACCTGGCTGC | GCGGAACTGCATGCT | GGACGAGTCATTCAC | 3288 |
| Ron-V2 | GGTAGCCCGCGGCAT | GGAGTACCTGGCAGA | GCAGAAGTTTGTGCA | CAGGGACCTGGCTGC | GCGGAACTGCATGCT | GGACGAGTCATTCAC | 3315 |
| Ron-V1 | GGTAGCCCGCGGCAT | GGAGTACCTGGCAGA | GCAGAAGTTTGTGCA | CAGGGACCTGGCTGC | GCGGAACTGCATGCT | GGACGAGTCATTCAC | 3435 |
| Ron | GGTAGCCCGCGGCAT | GGAGTACCTGGCAGA | GCAGAAGTTTGTGCA | CAGGGACCTGGCTGC | GCGGAACTGCATGCT | GGACGAGTCATTCAC | 3690 |
| | | | | | | | | |
| Ron-V3 | AGTCAAGGTGGCTGA | CTTTGGTTTGGCCCG | CGACATCCTGGACAG | GGAGTACTATAGTGT | TCAACAGCATCGCCA | CGCTCGCCTACCTGT | 3378 |
| Ron-V2 | AGTCAAGGTGGCTGA | CTTTGGTTTGGCCCG | CGACATCCTGGACAG | GGAGTACTATAGTGT | TCAACAGCATCGCCA | CGCTCGCCTACCTGT | 3405 |
| Ron-V1 | AGTCAAGGTGGCTGA | CTTTGGTTTGGCCCG | CGACATCCTGGACAG | GGAGTACTATAGTGT | TCAACAGCATCGCCA | CGCTCGCCTACCTGT | 3525 |
| Ron | AGTCAAGGTGGCTGA | CTTTGGTTTGGCCCG | CGACATCCTGGACAG | GGAGTACTATAGTGT | TCAACAGCATCGCCA | CGCTCGCCTACCTGT | 3780 |
| | | | | | | | | |
| Ron-V3 | GAAGTGGATGGCGCT | GGAGAGCCTGCAGAC | CTATAGATTTACCAC | CAAGTCTGATGTG-- | --------------- | --------------- | 3436 |
| Ron-V2 | GAAGTGGATGGCGCT | GGAGAGCCTGCAGAC | CTATAGATTTACCAC | CAAGTCTGATGTG-- | --------------- | --------------- | 3463 |
| Ron-V1 | GAAGTGGATGGCGCT | GGAGAGCCTGCAGAC | CTATAGATTTACCAC | CAAGTCTGATGTG-- | --------------- | --------------- | 3583 |
| Ron | GAAGTGGATGGCGCT | GGAGAGCCTGCAGAC | CTATAGATTTACCAC | CAAGTCTGATGTGTG | GTCATTTGGTGTGCT | GCTGTGGGAACTGCT | 3870 |
| | | | | | | | | |
| Ron-V3 | --------------- | --------------- | --------------- | --------------- | --------------- | --------------- | 3436 |
| Ron-V2 | --------------- | --------------- | --------------- | --------------- | --------------- | --------------- | 3463 |
| Ron-V1 | --------------- | --------------- | --------------- | --------------- | --------------- | --------------- | 3583 |
| Ron | GACACGGGGTGCCCC | ACCATACCGCCACAT | TGACCCTTTTGACCT | TACCCACTTCCTGGC | CCAGGGTCGGCGCCT | GCCCCAGCCTGAGTA | 3960 |
| | | | | | | | | |
| Ron-V3 | --------------- | GTACCAAGTGATGCA | GCAATGCTGGGAGGC | AGACCCAGCAGTGCG | ACCCACCTTCAGAGT | ACTAGTGGGGGAGGT | 3511 |
| Ron-V2 | --------------- | GTACCAAGTGATGCA | GCAATGCTGGGAGGC | AGACCCAGCAGTGCG | ACCCACCTTCAGAGT | ACTAGTGGGGGAGGT | 3538 |
| Ron-V1 | --------------- | GTACCAAGTGATGCA | GCAATGCTGGGAGGC | AGACCCAGCAGTGCG | ACCCACCTTCAGAGT | ACTAGTGGGGGAGGT | 3658 |
| Ron | TTGCCCTGATTCTCT | GTACCAAGTGATGCA | GCAATGCTGGGAGGC | AGACCCAGCAGTGCG | ACCCACCTTCAGAGT | ACTAGTGGGGGAGGT | 4050 |

FIG. 5-10  SEQ ID NOs: 2, 4, 6, 8 cont.

```
Ron-V3  GGAGCAGAGATAGTGTC TGCACTGCTTGGGGA CCATTATGTGCAGCT GCCAGCAACCTACAT GAACTTG---------- ---------------- 3578
Ron-V2  GGAGCAGAGATAGTGTC TGCACTGCTTGGGGA CCATTATGTGCAGCT GCCAGCAACCTACAT GAACTTG---------- ---------------- 3605
Ron-V1  GGAGCAGAGATAGTGTC TGCACTGCTTGGGGA CCATTATGTGCAGCT GCCAGCAACCTACAT GAACTTG---------- ---------------- 3725
Ron     GGAGCAGAGATAGTGTC TGCACTGCTTGGGGA CCATTATGTGCAGCT GCCAGCAACCTACAT GAACTTGGGCCCCAG  CACCTCGCATGAGAT  4140

Ron-V3  ---------------- ---------------- ---------------- ---------------- ---------------- ---------------- 3578
Ron-V2  ---------------- ---------------- ---------------- ---------------- ---------------- ---------------- 3605
Ron-V1  ---------------- ---------------- ---------------- ---------------- ---------------- ---------------- 3725
Ron     GAATGTGCGTCCAGA  ACAGCCGAGTTCTC  ACCCATGCCAGGGAA TGTACGCCGGCCCCG GCCACTCTCAGAGACC TCCTCGCCCCACTTG  4230

Ron-V3  ---------------- ---------------- -----AGCTAACCC  CAAGGCTGCCTCTGG GCCATGCCAGGCCAG AGCAGTGGCCCTCCA  3632
Ron-V2  ---------------- ---------------- -----AGCTAACCC  CAAGGCTGCCTCTGG GCCATGCCAGGCCAG AGCAGTGGCCCTCCA  3659
Ron-V1  ---------------- ---------------- -----AGCTAACCC  CAAGGCTGCCTCTGG GCCATGCCAGGCCAG AGCAGTGGCCCTCCA  3779
Ron     ACTTAGTTCTTGGGC  TGGACCTGCTTAGCT GCCTTGAGCTAACCC CAAGGCTGCCTCTGG GCCATGCCAGGCCAG AGCAGTGGCCCTCCA  4320

Ron-V3  CCTTGTTCCTGCCCT  TTAACTTTCAGAGGC AATAGGTAAAATGGGC CCATTAGTCCCTCA  CTCCACAGAGTGAGC CAGTGAGGGCAGTCC  3722
Ron-V2  CCTTGTTCCTGCCCT  TTAACTTTCAGAGGC AATAGGTAAAATGGGC CCATTAGTCCCTCA  CTCCACAGAGTGAGC CAGTGAGGGCAGTCC  3749
Ron-V1  CCTTGTTCCTGCCCT  TTAACTTTCAGAGGC AATAGGTAAAATGGGC CCATTAGTCCCTCA  CTCCACAGAGTGAGC CAGTGAGGGCAGTCC  3869
Ron     CCTTGTTCCTGCCCT  TTAACTTTCAGAGGC AATAGGTAAAATGGGC CCATTAGTCCCCTCA CTCCACAGAGTGAGC CAGTGAGGGCAGTCC  4410

Ron-V3  TGCAACATGTATTTA  TGGAGTGCCTGCTGT GGACCCTGTCTTCTG GGCACAGTGGACTCA GCAGTGACCACACCA ACACTGACCCTTGAA  3812
Ron-V2  TGCAACATGTATTTA  TGGAGTGCCTGCTGT GGACCCTGTCTTCTG GGCACAGTGGACTCA GCAGTGACCACACCA ACACTGACCCTTGAA  3839
Ron-V1  TGCAACATGTATTTA  TGGAGTGCCTGCTGT GGACCCTGTCTTCTG GGCACAGTGGACTCA GCAGTGACCACACCA ACACTGACCCTTGAA  3959
Ron     TGCAACATGTATTTA  TGGAGTGCCTGCTGT GGACCCTGTCTTCTG GGCACAGTGGACTCA GCAGTGACCACACCA ACACTGACCCTTGAA  4500
```

FIG. 5-11    SEQ ID NOs: 2, 4, 6, 8 cont.

```
Ron-V3  CCAATAAAGGAACAA ATGACTATTAAAGCA CAAAAAAAAAA  3853
Ron-V2  CCAATAAAGGAACAA ATGACTATTAAAGCA CAAAAAAAAAA  3880
Ron-V1  CCAATAAAGGAACAA ATGACTATTAAAGCA CAAAAAAAAAA  4000
Ron     CCAATAAAGGAACAA ATGACTATTAAAGCA CAAAAAAAAAA  4541
```

FIG. 6-1

```
Ron-V3  MELLPPLPQSFLLLL LLPAKPAAGEDWQCP RTPYAASRDFDVKYV VPSFSAGGLVQAMVT YEGDRNESAVFVAIR NRLHVLGPDLKSVQS    90
Ron-V2  MELLPPLPQSFLLLL LLPAKPAAGEDWQCP RTPYAASRDFDVKYV VPSFSAGGLVQAMVT YEGDRNESAVFVAIR NRLHVLGPDLKSVQS    90
Ron-V1  MELLPPLPQSFLLLL LLPAKPAAGEDWQCP RTPYAASRDFDVKYV VPSFSAGGLVQAMVT YEGDRNESAVFVAIR NRLHVLGPDLKSVQS    90
Ron     MELLPPLPQSFLLLL LLPAKPAAGEDWQCP RTPYAASRDFDVKYV VPSFSAGGLVQAMVT YEGDRNESAVFVAIR NRLHVLGPDLKSVQS    90

Ron-V3  LATGPAGDPGCQTCA ACGPGPHGPPGDTDT KVLVLDPALPALVSC GSSLQGRCFLHDLEP QGTAVHLAAPACLFS AHHNRPDDCPDCVAS   180
Ron-V2  LATGPAGDPGCQTCA ACGPGPHGPPGDTDT KVLVLDPALPALVSC GSSLQGRCFLHDLEP QGTAVHLAAPACLFS AHHNRPDDCPDCVAS   180
Ron-V1  LATGPAGDPGCQTCA ACGPGPHGPPGDTDT KVLVLDPALPALVSC GSSLQGRCFLHDLEP QGTAVHLAAPACLFS AHHNRPDDCPDCVAS   180
Ron     LATGPAGDPGCQTCA ACGPGPHGPPGDTDT KVLVLDPALPALVSC GSSLQGRCFLHDLEP QGTAVHLAAPACLFS AHHNRPDDCPDCVAS   180

Ron-V3  PLGTRVTVVEQGQAS YFYVASSLDAAVAGS FSPRSVSIRRLKADA SGFAPGFVALSVLPK HLVSYSIEYVHSFHT GAFVYFLTVQPASVT   270
Ron-V2  PLGTRVTVVEQGQAS YFYVASSLDAAVAGS FSPRSVSIRRLKADA SGFAPGFVALSVLPK HLVSYSIEYVHSFHT GAFVYFLTVQPASVT   270
Ron-V1  PLGTRVTVVEQGQAS YFYVASSLDAAVAGS FSPRSVSIRRLKADA SGFAPGFVALSVLPK HLVSYSIEYVHSFHT GAFVYFLTVQPASVT   270
Ron     PLGTRVTVVEQGQAS YFYVASSLDAAVAGS FSPRSVSIRRLKADA SGFAPGFVALSVLPK HLVSYSIEYVHSFHT GAFVYFLTVQPASVT   270

Ron-V3  DDPSALHTRLARLSA TEPELGDYRELVLDC RFAPKRRRRGAPEGG QPYPVLQVAHSAPVG AQLATELSIAEGQEV LFGVFVTGKDGGPGV   360
Ron-V2  DDPSALHTRLARLSA TEPELGDYRELVLDC RFAPKRRRRGAPEGG QPYPVLQVAHSAPVG AQLATELSIAEGQEV LFGVFVTGKDGGPGV   360
Ron-V1  DDPSALHTRLARLSA TEPELGDYRELVLDC RFAPKRRRRGAPEGG QPYPVLQVAHSAPVG AQLATELSIAEGQEV LFGVFVTGKDGGPGV   360
Ron     DDPSALHTRLARLSA TEPELGDYRELVLDC RFAPKRRRRGAPEGG QPYPVLQVAHSAPVG AQLATELSIAEGQEV LFGVFVTGKDGGPGV   360

Ron-V3  GPNSVVCAFPIDLLD TLIDEGVERCCESPV HPGLRRGLDFFQSPS FCPNPPGLEALSPNT SCRHFPLLVSSSFSR VDLFNGLLGPVQVTA   450
Ron-V2  GPNSVVCAFPIDLLD TLIDEGVERCCESPV HPGLRRGLDFFQSPS FCPNPPGLEALSPNT SCRHFPLLVSSSFSR VDLFNGLLGPVQVTA   450
Ron-V1  GPNSVVCAFPIDLLD TLIDEGVERCCESPV HPGLRRGLDFFQSPS FCPNPPGLEALSPNT SCRHFPLLVSSSFSR VDLFNGLLGPVQVTA   450
Ron     GPNSVVCAFPIDLLD TLIDEGVERCCESPV HPGLRRGLDFFQSPS FCPNPPGLEALSPNT SCRHFPLLVSSSFSR VDLFNGLLGPVQVTA   450
```

FIG. 6-2

```
Ron-V3  LYVTRLDNVTVAHMG  TMDGRILQVELVRSL  NYLLYVSNFSLGDSG  QPVQRDVSRLGDHLL  FASGDQVFQVPIRGP  GCRHFLTCGRCLRAW  540
Ron-V2  LYVTRLDNVTVAHMG  TMDGRILQVELVRSL  NYLLYVSNFSLGDSG  QPVQRDVSRLGDHLL  FASGDQVFQVPIRGP  GCRHFLTCGRCLRAW  540
Ron-V1  LYVTRLDNVTVAHMG  TMDGRILQVELVRSL  NYLLYVSNFSLGDSG  QPVQRDVSRLGDHLL  FASGDQVFQVPIRGP  GCRHFLTCGRCLRAW  540
Ron     LYVTRLDNVTVAHMG  TMDGRILQVELVRSL  NYLLYVSNFSLGDSG  QPVQRDVSRLGDHLL  FASGDQVFQVPIRGP  GCRHFLTCGRCLRAW  540

Ron-V3  HFMGCGWCGNMCGQQ  KECPGSWQQDHCPPK  LTEFHPHSGPLRGST  RLTLCGSNFYLHPSG  LVPEGTHQVTVGQSP  CRPLPKDSSKLRPVP  630
Ron-V2  HFMGCGWCGNMCGQQ  KECPGSWQQDHCPPK  LTEFHPHSGPLRGST  RLTLCGSNFYLHPSG  LVPEGTHQVTVGQSP  CRPLPKDSSKLRPVP  630
Ron-V1  HFMGCGWCGNMCGQQ  KECPGSWQQDHCPPK  LTEFHPHSGPLRGST  RLTLCGSNFYLHPSG  LVPEGTHQVTVGQSP  CRPLPKDSSKLRPVP  630
Ron     HFMGCGWCGNMCGQQ  KECPGSWQQDHCPPK  LTEFHPHSGPLRGST  RLTLCGSNFYLHPSG  LVPEGTHQVTVGQSP  CRPLPKDSSKLRPVP  630

Ron-V3  RKDFVEEFECELEPL  GTQAVGPTNVSLTVT  NMPPGKHFRVDGTSV  LRGFSFMEPVLIAVQ  PLFGPRAGGTCLTLE  GQSLSVGTSRAVLVN  720
Ron-V2  RKDFVEEFECELEPL  GTQAVGPTNVSLTVT  NMPPGKHFRVDGTSV  LRGFSFMEPVLIAVQ  PLFGPRAGGTCLTLE  GQSLSVGTSRAVLVN  720
Ron-V1  RKDFVEEFECELEPL  GTQAVGPTNVSLTVT  NMPPGKHFRVDGTSV  LRGFSFMEPVLIAVQ  PLFGPRAGGTCLTLE  GQSLSVGTSRAVLVN  720
Ron     RKDFVEEFECELEPL  GTQAVGPTNVSLTVT  NMPPGKHFRVDGTSV  LRGFSFMEPVLIAVQ  PLFGPRAGGTCLTLE  GQSLSVGTSRAVLVN  720

Ron-V3  GTECLLARVSEGQLL  CATPPGATVASVPLS  LQVGGAQVPGSWTFQ  YREDPVVLSISPNCG  YINSHITICGQHLTS  AWHLVLSFHDGLRAV  810
Ron-V2  GTECLLARVSEGQLL  CATPPGATVASVPLS  LQVGGAQVPGSWTFQ  YREDPVVLSISPNCG  YINSHITICGQHLTS  AWHLVLSFHDGLRAV  810
Ron-V1  GTECLLARVSEGQLL  CATPPGATVASVPLS  LQVGGAQVPGSWTFQ  YREDPVVLSISPNCG  YINSHITICGQHLTS  AWHLVLSFHDGLRAV  810
Ron     GTECLLARVSEGQLL  CATPPGATVASVPLS  LQVGGAQVPGSWTFQ  YREDPVVLSISPNCG  YINSHITICGQHLTS  AWHLVLSFHDGLRAV  810

Ron-V3  ESRCERQLPEQQLCR  LPEYVVRDPQGWVAG  NLSARGDGAAGFTLP  GFRFLPPHPPSANL   VPLKPEEHAIKFE--  ---------------  883
Ron-V2  ESRCERQLPEQQLCR  LPEYVVRDPQGWVAG  NLSARGDGAAGFTLP  GFRFLPPHPPSANL   VPLKPEEHAIKFE--  ---------------  883
Ron-V1  ESRCERQLPEQQLCR  LPEYVVRDPQGWVAG  NLSARGDGAAGFTLP  GFRFLPPHPPSANL   VPLKPEEHAIKFEYI  GLGAVADCVGINVTV  900
Ron     ESRCERQLPEQQLCR  LPEYVVRDPQGWVAG  NLSARGDGAAGFTLP  GFRFLPPHPPSANL   VPLKPEEHAIKFEYI  GLGAVADCVGINVTV  900
```

FIG. 6-3

```
Ron-V3  --------------- --------------- --------------- --------------- --VCVD--------- --------------- 887
Ron-V2  --------------- --------------- -------LGQDGAP LQVCVD--------- --------------- --------------- 896
Ron-V1  GGESCQHEFRGDMVV CPLPPSLQLGQDGAP LQVCVD--------- --------------- --------------- --------------- 936
Ron     GGESCQHEFRGDMVV CPLPPSLQLGQDGAP LQVCVDGECHILGRV VRPGPDGVPQSTLLG ILLPLILLVAALATA LVFSYWWRRKQLVLP 990

Ron-V3  --------------- --------------- --------------- -ALPAIDGLDSTTCV HGASFSDSEDESCVP LLRKESIQLRDLDSA 946
Ron-V2  --------------- --------------- --------------- -ALPAIDGLDSTTCV HGASFSDSEDESCVP LLRKESIQLRDLDSA 955
Ron-V1  --------------- --------------- --------------- -ALPAIDGLDSTTCV HGASFSDSEDESCVP LLRKESIQLRDLDSA 995
Ron     PNLNDLASLDQTAGA TPLPILYSGSDYRSG LALPAIDGLDSTTCV HGASFSDSEDESCVP LLRKESIQLRDLDSA 1080

Ron-V3  VTHSDRVIGKGHFGV VYHGEYIDQAQNRIQ CAIKSLSRITEMQQV EAFLREGLLMRGLNH PNVLALIGIMLPPEG LPHVLLPYMCHGDLL 1036
Ron-V2  VTHSDRVIGKGHFGV VYHGEYIDQAQNRIQ CAIKSLSRITEMQQV EAFLREGLLMRGLNH PNVLALIGIMLPPEG LPHVLLPYMCHGDLL 1045
Ron-V1  VTHSDRVIGKGHFGV VYHGEYIDQAQNRIQ CAIKSLSRITEMQQV EAFLREGLLMRGLNH PNVLALIGIMLPPEG LPHVLLPYMCHGDLL 1085
Ron     VTHSDRVIGKGHFGV VYHGEYIDQAQNRIQ CAIKSLSRITEMQQV EAFLREGLLMRGLNH PNVLALIGIMLPPEG LPHVLLPYMCHGDLL 1170

Ron-V3  QFIRSPQRNPTVKDL ISFGLQVARGMEYLA EQKFVHRDLAARNCM LDESFTVKVADFGLA RDILDREYYSVQQHR HARLPVKWMALESLQ 1126
Ron-V2  QFIRSPQRNPTVKDL ISFGLQVARGMEYLA EQKFVHRDLAARNCM LDESFTVKVADFGLA RDILDREYYSVQQHR HARLPVKWMALESLQ 1135
Ron-V1  QFIRSPQRNPTVKDL ISFGLQVARGMEYLA EQKFVHRDLAARNCM LDESFTVKVADFGLA RDILDREYYSVQQHR HARLPVKWMALESLQ 1175
Ron     QFIRSPQRNPTVKDL ISFGLQVARGMEYLA EQKFVHRDLAARNCM LDESFTVKVADFGLA RDILDREYYSVQQHR HARLPVKWMALESLQ 1260

Ron-V3  TYRFTTKSDVVPSD- --------------- --------------- --------------- --------------- ------AAMLG 1145
Ron-V2  TYRFTTKSDVVPSD- --------------- --------------- --------------- --------------- ------AAMLG 1154
Ron-V1  TYRFTTKSDVVPSD- --------------- --------------- --------------- --------------- ------AAMLG 1194
Ron     TYRFTTKSDWSFGV LLWELLTRGAPPYRH IDPFDLTHFLAQGRR LPQPEYCPDSLYQVM QQCWEADPAVRPTFR VLVGEVEQIVSALLG 1350
```

FIG. 6-4

```
Ron-V3  GR-----PSSATHLQS TSGGGGADSVCTAWG PLCAAASNLHELELT PRLPLGHARPEQWPS TLFLPFNFQRQ--- ------  1212
Ron-V2  GR-----PSSATHLQS TSGGGGADSVCTAWG PLCAAASNLHELELT PRLPLGHARPEQWPS TLFLPFNFQRQ--- ------  1221
Ron-V1  GR-----PSSATHLQS TSGGGGADSVCTAWG PLCAAASNLHELELT PRLPLGHARPEQWPS TLFLPFNFQRQ--- ------  1261
Ron     DHYVQLPATYMNL-- ---------------G P-----STSHEM--- ------NVRPEQ-PQ FSPMPGNVRRPRPLS EPPRPT  1400
```

HUMAN RON-RELATED GENE VARIANT ASSOCIATED WITH CANCERS

CROSS REFERENCE TO RELATED APPLICATIONS

This application claims priority to U.S. application Ser. No. 11/465,308 filed Aug. 17, 2006, entitled "Human Ron-Related Gene Variant Associated with Cancers, which is incorporated herein in its entirety.

FIELD OF THE INVENTION

The invention relates to the nucleic acid and polypeptide sequences of a novel human Ron-related gene variant, preparation process thereof, and uses of the same in diagnosing cancers, in particular, breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

BACKGROUND OF THE INVENTION

Cancer is one of the major causes of death in the world. According to the report from the WHO Fact Sheet-Cancer (2003), cancer accounts for 7.1 million (12.6% of the global total) deaths annually and new cancer cases are expected to be increased from 10 million people in 2000 to 15 million people by 2020. In recent years, much progress has been made toward understanding the molecular and cellular biology of cancers. Many important contributions have been made by the identification of several key genetic factors associated with cancers. However, the treatments of cancers still mainly depend on surgery, chemotherapy and radiotherapy because the molecular mechanisms underlying the pathogenesis of cancers remain largely unclear.

It is interesting to note that receptor tyrosine kinases are a family of proteins reported to be involved in many fundamental cellular processes such as cell cycle, signalling transduction, proliferation, differentiation, adhesion, migration, and apoptosis. An important role of the receptor tyrosine kinases in the development of cancers has been reported previously. Therefore, future strategies for the prevention and treatment of cancers may be focused on the elucidation of the receptor tyrosine kinases which are involved in the pathogenesis of cancers. Ron, a member of the receptor tyrosine kinase family located on human chromosome 3p21 (a region frequently deleted in small cell lung carcinoma), was isolated and identified through the screening of cDNA libraries. Previous studies have indicated that Ron is involved in many genetic mechanisms of the tumor cells (Wang et al., (2003) Carcinogenesis 24:1291-300; Angeloni et al., (2004) J Biol. Chem. 279:3726-32; Peace et al., (2005) Cancer Res. 65:1285-93; Camp et al., (2005) Ann Surg Oncol. 12:273-81), and that Ron is a potential target for understanding the pathogenesis of cancers. In addition, the association between gene variants and diseases has been reported previously. Therefore, the discovery of gene variants of Ron may be important for the diagnostic markers of cancers.

SUMMARY OF THE INVENTION

The present invention provides one Ron-related gene variant present in human breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma. The nucleotide sequence of the gene variant and polypeptide sequence encoded thereby can be used for the diagnosis of any diseases associated with this gene variant or cancers, in particular, breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

The invention further provides an expression vector and host cell for expressing the variant.

The invention further provides a method for producing the variant.

The invention further provides an antibody that specifically binds to the variant. For example, by selecting a sequence unique to one of the variants, e.g., a peptide fragment that spans one the deletion junctions, an antibody may be generated that binds to one of the variants and not to RON. Preferably, such peptide antigens are at least 17 amino acid long, but in some cases smaller peptides such as 10 mers, 12 mers, or 15 mers may suffice. Longer peptides, such as 20 mers, 50 mers, hundred-mers (and those therebetween) and even up to full length proteins may be used.

The invention also provides methods for detecting the presence of the variant in a mammal.

BRIEF DESCRIPTION OF THE DRAWINGS

FIG. 1 shows the nucleic acid sequence (SEQ ID NO:1), amino acid sequence (SEQ ID NO:2) and nucleic acid with corresponding amino acid sequence (SEQ ID NO: 1 & 2) of Ron.

FIG. 2 shows the nucleic acid sequence (SEQ ID NO:3), amino acid sequence (SEQ ID NO:4) and nucleic acid with corresponding amino acid sequence (SEQ ID NO: 3 & 4) of Ron-V1.

FIG. 3 shows the nucleic acid sequence (SEQ ID NO:5), amino acid sequence (SEQ ID NO:6) and nucleic acid with corresponding amino acid sequence (SEQ ID NO: 5 & 6) of Ron-V2.

FIG. 4 shows the nucleic acid sequence (SEQ ID NO:7), amino acid sequence (SEQ ID NO:8) and nucleic acid with corresponding amino acid sequence (SEQ ID NO: 7 & 8) of Ron-V3.

FIG. 5 shows the nucleotide sequence alignment between the human Ron gene (SEQ ID NO: 1) and its related gene variants (Ron-V1, Ron-V2, and Ron-V3, SEQ ID NO: ID 3, 5, 7).

FIG. 6 shows the amino acid sequence alignment between the human Ron protein (SEQ ID NO: 2) and its related gene variants (Ron-V1, Ron-V2, and Ron-V3) (SEQ ID NO: 4, 6, 8).

DETAILED DESCRIPTION OF THE INVENTION

Figure 7:
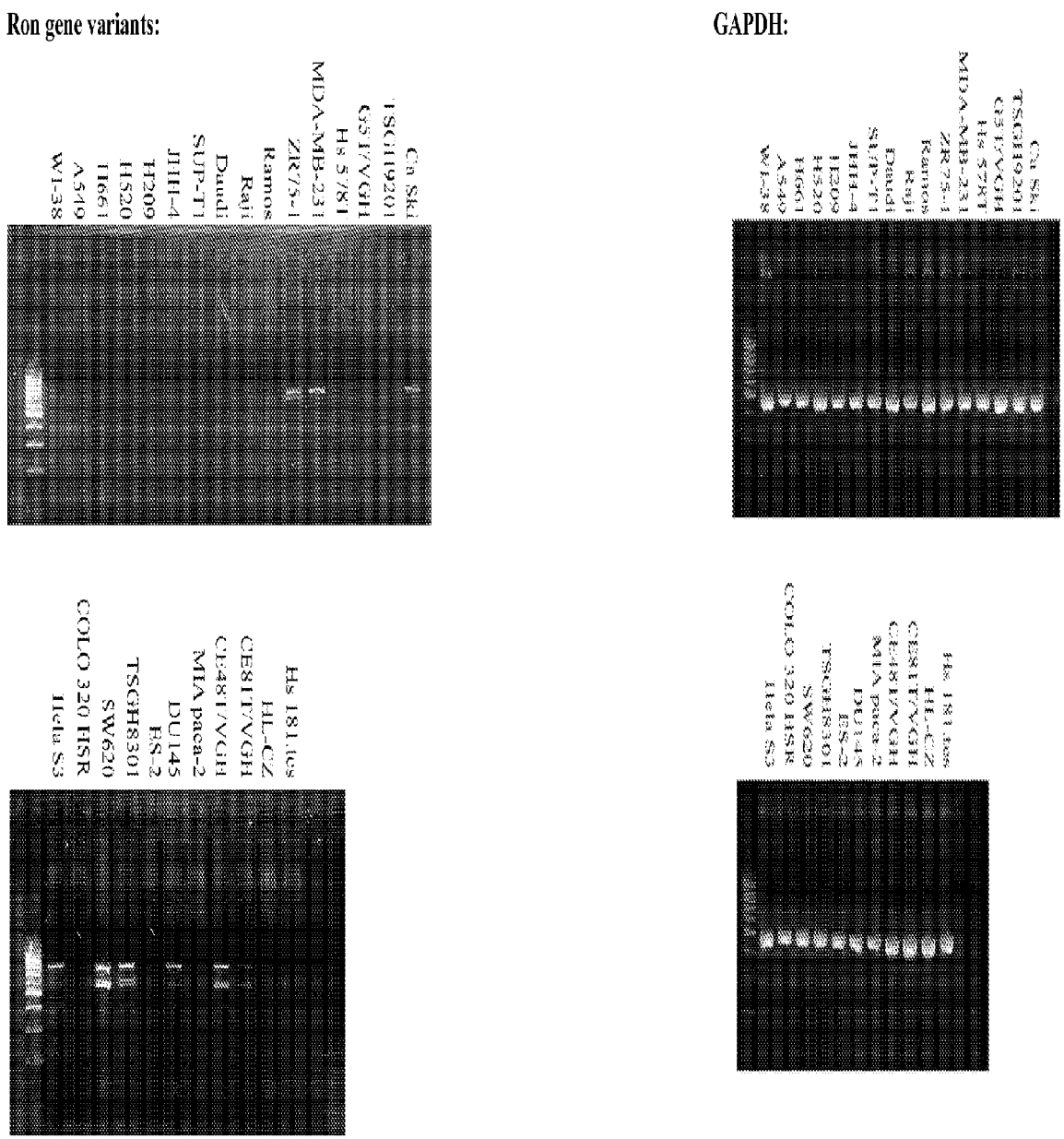
FIG. 7 shows the expression pattern of Ron gene variants in human cell lines.

All technical and scientific terms used herein, unless otherwise defined, have the same meanings as commonly understood by persons skilled in the art.

The term "antibody" used herein denotes intact molecules (a polypeptide or group of polypeptides) as well as fragments thereof, such as Fab, R(ab')2, and Fv fragments, which are capable of binding epitopes. Antibodies are produced by specialized B cells after stimulation by an antigen. Structurally, antibody consists of four subunits including two heavy chains and two light chains. The internal surface shape and charge distribution of the antibody binding domain is complementary to the features of an antigen. Thus, antibody can specifically act against the antigen in an immune response.

The term "base pair (bp)" used herein denotes nucleotides composed of a purine on one strand of DNA which can be hydrogen bonded to a pyrimidine on the other strand. Thymine (or uracil) and adenine residues are linked by two hydrogen bonds. Cytosine and guanine residues are linked by three hydrogen bonds.

The term "Basic Local Alignment Search Tool ("BLAST")" (BLAST; Altschul et al., (1997) Nucleic Acids Res. 25: 3389-3402) used herein denotes programs for evaluation of homologies between a query sequence (amino or nucleic acid) and a test sequence. Specific BLAST programs are described as follows:

(1) BLASTN compares a nucleotide query sequence against a nucleotide sequence database;

(2) BLASTP compares an amino acid query sequence against a protein sequence database;

(3) BLASTX compares the six-frame conceptual translation products of a query nucleotide sequence against a protein sequence database;

(4) TBLASTN compares a query protein sequence against a nucleotide sequence database translated in all six reading frames; and (5) TBLASTX compares the six-frame translations of a nucleotide query sequence against the six-frame translations of a nucleotide sequence database.

The term "cDNA" used herein denotes nucleic acids synthesized from a mRNA template using reverse transcriptase.

The term "cDNA library" used herein denotes a library composed of complementary DNAs which are reverse-transcribed from mRNAs.

The term "complement" used herein denotes a polynucleotide sequence capable of forming base pairing with another polynucleotide sequence. For example, the sequence 5'-ATG-GACTTACT-3' binds to the complementary sequence 5'-AG-TAAGTCCAT-3'.

The term "deletion" used herein denotes a removal of a portion of one or more amino acid residues/nucleotides from a gene.

The term "expressed sequence tags (ESTs)" used herein denotes short (200 to 500 base pairs) nucleotide sequence that derives from either 5' or 3' end of a cDNA.

The term "expression vector" used herein denotes nucleic acid constructs which contain a cloning site for introducing the DNA into vector, one or more selectable markers for selecting vectors containing the DNA, an origin of replication for replicating the vector whenever the host cell divides, a terminator sequence, a polyadenylation signal, and a suitable control sequence which can effectively express the DNA in a suitable host. The suitable control sequence may include promoter, enhancer and other regulatory sequences necessary for directing polymerases to transcribe the DNA.

The term "host cell" used herein denotes a cell which is used to receive, maintain, and allow the reproduction of an expression vector comprising DNA. Host cells are transformed or transfected with suitable vectors constructed using recombinant DNA methods. The recombinant DNA introduced with the vector is replicated whenever the cell divides.

The term "insertion" or "addition" used herein denotes the addition of a portion of one or more amino acid residues/nucleotides to a gene.

The term "in silico" used herein denotes a process of using computational methods (e.g., BLAST) to analyze DNA sequences.

The term "polymerase chain reaction (PCR)" used herein denotes a method which increases the copy number of a nucleic acid sequence using a DNA polymerase and a set of primers (about 20 bp oligonucleotides complementary to each strand of DNA) under suitable conditions (successive rounds of primer annealing, strand elongation, and dissociation).

The term "polynucleotide" or "nucleic acid sequence" used herein denotes a sequence of nucleotide (guanine, cytosine, thymine or adenine) in a specific order that can be a natural or synthesized fragment of DNA or RNA. It may be single-stranded or double-stranded.

The term "protein" or "polypeptide" used herein denotes a sequence of amino acids in a specific order that can be encoded by a gene or by a recombinant DNA. It can also be chemically synthesized.

The term "RNA interference (RNAi)" used herein denotes an introduction of homologous double stranded RNA (dsRNA) into a cell to specifically inhibit the expression of a gene.

The term "reverse transcriptase-polymerase chain reaction (RT-PCR)" used herein denotes a process which transcribes mRNA to complementary DNA strand using reverse transcriptase followed by polymerase chain reaction to amplify the specific fragment of DNA sequences.

The term "transformation" used herein denotes a process describing the uptake, incorporation, and expression of exogenous DNA by prokaryotic host cells.

The term "transfection" used herein denotes a process describing the uptake, incorporation, and expression of exogenous DNA by eukaryotic host cells.

The term "variant" used herein denotes a fragment of sequence (nucleotide or amino acid) inserted or deleted by one or more nucleotides/amino acids.

According to the present invention, the polypeptides of one novel human Ron-related gene variant and the nucleic acid sequences encoding the same are provided.

According to the present invention, human Ron cDNA sequence was used to query the human EST databases using BLAST program to search for Ron-related gene variants. Three human cDNA partial sequences (i.e., EST) showing similar to Ron was identified from ESTs deposited in a cDNA database constructed using a SW620 (colon adenocarcinoma) cell line. The cDNA clones, named Ron-V1 (Ron variant 1), Ron-V2 (Ron variant 2), and Ron-V3 (Ron variant 3), were then isolated from the SW620 cDNA library and sequenced. FIGS. 2-4 show the nucleic acid sequences (SEQ ID NOs: 3, 5, & 7) of Ron-V1, Ron-V2, and Ron-V3 and its corresponding amino acid sequences (SEQ ID NOs: 4, 6, & 8) encoded thereby.

The full-length of the Ron-V1 cDNA is a 4000 bp clone containing a 3783 bp open reading frame (ORF) extending from 29 bp to 3811 bp, which corresponds to an encoded protein of 1261 amino acid residues with a predicted molecular mass of 136.1 kDa. The initiation ATG sequence of Ron-V1 is located at nucleotide 29-31 bp. The full-length of the Ron-V2 cDNA is a 3880 bp clone containing a 3663 bp open reading frame (ORF) extending from 29 bp to 3691 bp, which corresponds to an encoded protein of 1221 amino acid residues with a predicted molecular mass of 132 kDa. The initiation ATG sequence of Ron-V2 is located at nucleotide 29-31 bp. The full-length of the Ron-V3 cDNA is a 3853 bp clone containing a 3636 bp open reading frame (ORF) extending from 29 bp to 3664 bp, which corresponds to an encoded protein of 1212 amino acid residues with a predicted molecular mass of 131.1 kDa. The initiation ATG sequence of Ron-V3 is located at nucleotide 29-31 bp. To determine the variations in sequence of Ron-V1, Ron-V2 and Ron-V3 cDNA clones, an alignment of Ron nucleotide/amino acid sequence with Ron-V1, Ron-V2 and Ron-V3 was performed (FIGS. 5 and 6). The results indicate that (1) Ron-V1: three major genetic deletions were found in the aligned nucleotide sequences showing that Ron-V1 has a 255 bp, a 137 bp and a 149 bp deletions in the sequence of Ron from nucleotides 2838-3092, nucleotides 3839-3975 and nucleotides 4118-4266, respectively; (2) Ron-V2: four major genetic deletions were found in the aligned nucleotide sequences showing that Ron-V2 has a 120 bp, a 255 bp, a 137 bp and a 149 bp deletions in the sequence of Ron from nucleotides 2678-2797, nucleotides 2838-3092, nucleotides 3839-3975 and nucleotides 4118-4266, respectively; (3) Ron-V3: four major genetic deletions were found in the aligned nucleotide sequences showing that Ron-V3 has a 147 bp, a 255 bp, a 137 bp and a 149 bp deletions in the sequence of Ron from nucleotides 2678-2824, nucleotides 2838-3092, nucleotides 3839-3975 and nucleotides 4118-4266, respectively. Scanning Ron, Ron-V1, Ron-V2 and Ron-V3 amino acid sequences against protein profile databases including PROSITE (Motif Scan) indicated that Ron protein contains one Sema domain (31-522aa), one Protein_Kinase_ATP (1088-1114aa), one Protein_Kinase_TYR (1204-1216aa), and one Protein_Kinase_DOM (1082-1345aa). Ron-V1 protein contains one Sema domain (31-522aa), one Protein_Kinase_ATP (1003-1029aa), one Protein_Kinase_TYR (1119-1131aa), and one Protein_Kinase_DOM (997-1261aa). Ron-V2 protein contains one Sema domain (31-522aa), one Protein_Kinase_ATP (963-989aa), one Protein_Kinase_TYR (1079-1091aa), and one Protein_Kinase_DOM (957-1221aa). Ron-V3 protein contains one Sema domain (31-522aa), one Protein_Kinase_ATP (954-980aa), one Protein_Kinase_TYR (1070-1082aa), and one Protein_Kinase_DOM (948-1212aa).

In the present invention, a search of ESTs deposited in dbEST at NCBI was performed to determine the presence of Ron gene variants in silico. The result of in silico analysis showed that one EST (GenBank accession number BG823879) was found to confirm the absence of 255 bp region on Ron-V1, Ron-V2, and Ron-V3 nucleotide sequences; one EST (GenBank accession number AW009348) was found to confirm the absence of 137 bp region on Ron-V1, Ron-V2, and Ron-V3 nucleotide sequences. Therefore, any Ron nucleotide fragments containing the immediately upstream and downstream sequences of the deleted 255 bp region (2837-2838 bp of Ron-V1; 2717-2718 bp of Ron-V2; 2691-2692 bp of Ron-V3) and/or 137 bp region (3583-3584 bp of Ron-V1; 3463-3464 bp of Ron-V2; 3436-3437 bp of Ron-V3) and/or 149 bp region (3725-3726 bp of Ron-V1; 3605-3606 bp of Ron-V2; 3578-3579 bp of Ron-V3) are the "gene targets" which may be used as probes to determine the presence of Ron-V1, Ron-V2, and Ron-V3 under high stringency conditions. An alternative approach is that any set of primers for amplifying the fragment containing the immediately upstream and downstream sequences of the deleted 255 bp region (2837-2838 bp of Ron-V1; 2717-2718 bp of Ron-V2; 2691-2692 bp of Ron-V3) and/or 137 bp region (3583-3584 bp of Ron-V1; 3463-3464 bp of Ron-V2; 3436-3437 bp of Ron-V3) and/or 149 bp region (3725-3726 bp of Ron-V1; 3605-3606 bp of Ron-V2; 3578-3579 bp of Ron-V3) may be used for determining the presence of the variants (Ron-V1, Ron-V2, and Ron-V3). On the other hand, any Ron nucleotide fragments containing the immediately upstream and downstream sequences of the deleted 120 bp region (2678-2679 bp of Ron-V2) and 147 bp region (2678-2679 bp of Ron-V3) are the "gene targets" which may be used as probes for determining the presence of Ron-V2 and Ron-V3, respectively, under high stringency conditions. An alternative approach is that any set of primers for amplifying the fragment containing the immediately upstream and downstream sequences of the deleted 120 bp region (2678-2679 bp of Ron-V2) and 147 bp region (2678-2679 bp of Ron-V3) may be used for determining the presence of Ron-V2 and Ron-V3, respectively.

According to the present invention, the polypeptides of the human Ron-V1, Ron-V2, and Ron-V3 and its fragments thereof may be produced through genetic engineering techniques. In this case, they are produced by appropriate host cells which have been transformed by DNAs that encode for the polypeptides or fragments thereof. The nucleotide sequence encoding the polypeptide of the human Ron-V1, Ron-V2, and Ron-V3 or their fragments thereof are inserted into an appropriate expression vector, i.e., a vector which contains the necessary elements for the transcription and translation of the inserted coding sequence in a suitable host. The nucleic acid sequence is inserted into the vector in a manner that will be expressed under appropriate conditions (e.g., in proper orientation and correct reading frame and with appropriate expression sequences, including an RNA polymerase binding sequence and a ribosomal binding sequence).

Any method that is known to those skilled in the art may be used to construct expression vectors containing sequences encoding the polypeptides of the human Ron-V1, Ron-V2, and Ron-V3 and appropriate transcriptional/translational control elements. These methods may include in vitro recombinant DNA and synthetic techniques, and in vivo genetic recombinants.

A variety of expression vector/host systems may be utilized to express the polypeptide-coding sequence. These include, but are not limited to, microorganisms such as bacteria transformed with recombinant bacteriophage, plasmid, or cosmid DNA expression vector; yeast transformed with yeast expression vector; insect cell systems infected with virus (e.g., baculovirus); plant cell system transformed with viral expression vector (e.g., cauliflower mosaic virus, CaMV, or tobacco mosaic virus, TMV); or animal cell system infected with virus (e.g., vaccina virus, adenovirus, etc.). Preferably, the host cell is a bacterium, and most preferably, the bacterium is *E. coli*.

Alternatively, the Polypeptides of the human Ron-V1, Ron-V2, and Ron-V3 or fragments thereof may be synthesized using chemical methods. For example, peptide synthesis can be performed using various solid-phase techniques. Automated synthesis may be achieved using the ABI 431A peptide synthesizer (Perkin-Elmer).

According to the present invention, the fragments of the polypeptides and nucleic acid sequences of the human Ron-V1, Ron-V2, and Ron-V3 are used as immunogens, primers or probes. Preferable, the purified fragments of the human Ron-V1, Ron-V2, and Ron-V3 are used. The fragments may be produced by enzyme digestion, chemical cleavage of isolated or purified polypeptide or nucleic acid sequences, or chemical synthesis. Thereafter, the fragments may be isolated or purified. Such isolated or purified fragments of the polypeptides and nucleic acid sequences can be used as immunogens, primers or probes.

The present invention further provides the antibodies which specifically bind one or more out-surface epitopes of the polypeptides of the human Ron-V1, Ron-V2, and Ron-V3.

According to the present invention, immunization of mammals with immunogens described herein, preferably humans, rabbits, rats, mice, sheep, goats, cows, or horses, is performed following procedures well known to those skilled in the art, for the purpose of obtaining antisera containing polyclonal antibodies or hybridoma lines secreting monoclonal antibodies.

Monoclonal antibodies can be prepared by standard techniques. Such techniques are disclosed, for example, in U.S. Pat. No. 4,271,145 and U.S. Pat. No. 4,196,265. An animal is immunized with the immunogen. Hybridomas are prepared by fusing spleen cells from the immunized animal with myeloma cells. The fusion products are screened for those producing antibodies that specifically bind to the immunogen. The positive hybridoma clones are isolated, and the monoclonal antibodies are recovered from those clones.

Immunization regimens for production of both polyclonal and monoclonal antibodies are well-known in the art. The immunogen may be injected by any of a number of routes, including subcutaneous, intravenous, intraperitoneal, intradermal, intramuscular, mucosal, or a combination thereof. The immunogen may be injected in soluble form, aggregate form, attached to a physical carrier, or mixed with an adjuvant, using methods and materials well-known in the art. The antisera and antibodies may be purified using well-known column chromatography methods.

According to the present invention, antibody fragments which contain specific binding sites for the polypeptides or fragments thereof may also be generated. For example, such fragments include, but are not limited to, F(ab')2 fragments produced by pepsin digestion of the antibody molecule and Fab fragments generated by reducing the disulfide bridges of the F(ab')2 fragments.

The subject invention also provides methods for diagnosing the diseases associated with Ron-V1, Ron-V2, or Ron-V3, particularly breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma, by utilizing the nucleic acid sequences, the polypeptide of the human Ron-V1, Ron-V2, or Ron-V3, or fragments thereof, and the antibodies against the polypeptides.

Since Ron-V1, Ron-V2, or Ron-V3 clones were isolated from a SW620 cDNA library, it is advisable that Ron-V1, Ron-V2, or Ron-V3 serve as a marker for the diagnosis of human colon adenocarcinoma. Thus, the expression levels/patterns of Ron-V1, Ron-V2, or Ron-V3 may be a useful indicator for screening patients suspected of having cancers or more specifically, breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma. This suggests that relative expression levels/patterns (mRNA or protein) may confer an increased susceptibility to cancers, and more preferably, to breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma. Fragments of Ron-V1, Ron-V2, or Ron-V3 transcripts (mRNAs) may be detected by RT-PCR approach. Polypeptides of Ron-V1, Ron-V2, or Ron-V3 may be determined by the binding of antibodies to these polypeptides. These approaches may be performed in accordance with conventional methods well known to persons skilled in the art. On the other hand, a method (RNAi; RNA interference) that is known to those skilled in the art may be used to interfere and degrade the targeted RNA using chemically synthesized double stranded short nucleic acid (about 23 nucleotides dsRNA) molecules (Montgomery et al. (1998) Proc Natl Acad Sci USA. 95:15502-7). According to the present invention, the double stranded short nucleic acid molecules containing the sequences of the "gene targets": nucleotides 2837-2838, nucleotides 3583-3584, or nucleotides 3725-3726 of Ron-V1; nucleotides 2717-2718, nucleotides 3463-3464, or nucleotides 3605-3606 of Ron-V2; nucleotides 2691-2692, nucleotides 3436-3437, or nucleotides 3578-3579 of Ron-V3, which may be used to specifically interfere and degrade Ron-V1, Ron-V2, and Ron-V3 mRNAs. On the other hand, the double stranded short nucleic acid molecules containing the sequence of the "gene targets": nucleotides 2678-2679 of Ron-V2 or Ron-V3, may be used to specifically interfere and degrade Ron-V2 and Ron-V3 mRNA, respectively. After RNAi approach was conducted, the decreased transcripts or polypeptides may be used to interpret the presence of Ron-V1, Ron-V2, and Ron-V3 mRNAs.

According to the present invention, the expression of these gene variant mRNAs in sample may be determined by, but not limited to, RT-PCR. Using TRIZOL™ reagents (LIFE TECHNOLOGY®), total RNA may be isolated from patient samples. Tissue samples (e.g., biopsy samples) are powdered under liquid nitrogen before homogenization. RNA purity and integrity are assessed by absorbance at 260/280 nm and by agarose gel electrophoresis. A set of primers can be designed to amplify the expected size of specific PCR fragments (gene targets) of Ron-V1, Ron-V2, and Ron-V3. For example, one of the primers is a fragment of the sequence (A fragment; forward primer) containing the gene targets: nucleotides 2837-2838, nucleotides 3583-3584, or nucleotides 3725-3726 of Ron-V1; nucleotides 2717-2718, nucleotides 3463-3464, or nucleotides 3605-3606 of Ron-V2; nucleotides 2691-2692, nucleotides 3436-3437, or nucleotides 3578-3579 of Ron-V3, and the other is a fragment (B fragment; reverse primer) designed from a reverse complementary strand of Ron-V1, Ron-V2, and Ron-V3 sequences at any location downstream of "A fragment". If "B fragment" is designed from a reverse complementary strand of the sequence containing the gene targets: nucleotides 2837-2838, nucleotides 3583-3584, or nucleotides 3725-3726 of Ron-V1; nucleotides 2717-2718, nucleotides 3463-3464, or nucleotides 3605-3606 of Ron-V2; nucleotides 2691-2692, nucleotides 3436-3437, or nucleotides 3578-3579 of Ron-V3, the "A fragment" is a fragment of the sequence at any location upstream of "B fragment". Alternatively, one primer (A fragment; forward primer) is at any location upstream of the sequence containing "gene targets" and the other is designed from a reverse complementary strand at any location downstream of the sequence containing "gene targets". PCR fragments are analyzed on a 1% agarose gel using five microliters (10%) of the amplified products. The intensity of the signals may be determined by using the Molecular Analyst program (version 1.4.1; Bio-Rad). Thus, the relative expression level for each amplified PCR product may be calculated based on the intensity of signals.

The RT-PCR experiment may be performed according to the manufacturer instructions (BOEHRINGER MANNHEIM®). A 50 µl reaction mixture containing 2 µl total RNA (0.1 µg/µl), 1 µl each primer (20 pM), 1 µl each dNTP (10 mM), 2.5 µl DTT solution (100 mM), 10 µl 5×RT-PCR buffer, 1 µl enzyme mixture, and 28.5 µl sterile distilled water may be subjected to the conditions such as reverse transcription at 60° C. for 30 minutes followed by 35 cycles of denaturation at 94° C. for 2 minutes, annealing at 60° C. for 2 minutes, and extension at 68° C. for 2 minutes. The RT-PCR analysis may be repeated twice to ensure reproducibility, for a total of three independent experiments.

The expression of gene variants can also be analyzed using Northern Blot hybridization approach. Specific fragments containing the sequences of the "gene targets" of the Ron-V1, Ron-V2, and Ron-V3 may be amplified by polymerase chain reaction (PCR) using primer set designed for RT-PCR. The amplified PCR fragment may be labeled and served as a probe to hybridize the membranes containing total RNAs extracted from the samples under the conditions of 55° C. in a suitable hybridization solution for 3 hours. Blots may be washed twice in 2×SSC, 0.1% SDS at room temperature for 15 minutes each, followed by two washes in 0.1×SSC and 0.1% SDS at 65° C. for 20 minutes each. After these washes, blot may be rinsed briefly in suitable washing buffer and incubated in blocking solution for 30 minutes, and then incubated in suitable antibody solution for 30 minutes. Blots may be washed in washing buffer for 30 minutes and equilibrated in suitable detection buffer before detecting the signals. Alternatively, the presence of the "gene targets" of the gene variants (cDNAs or PCR) can be detected using microarray approach. The cDNAs or PCR products corresponding to the nucleotide sequences of the present invention may be immobilized on a suitable substrate such as a glass slide. Hybridization can be preformed using the labeled mRNAs extracted from samples. After hybridization, nonhybridized mRNAs are removed. The relative abundance of each labeled transcript, hybridizing to a cDNA/PCR product immobilized on the microarray, can be determined by analyzing the scanned images.

According to the present invention, the presence of the polypeptide of Ron-V1, Ron-V2, and Ron-V3 in samples may be determined by, but not limited to, the immunoassay which uses the antibody that specifically binds to the polypeptide. The polypeptides of the gene variants may be expressed in prokaryotic cells by using suitable prokaryotic expression vectors. The cDNA fragments of Ron-V1, Ron-V2, and Ron-V3 genes encoding the amino acid sequences may be PCR amplified using primer set designed with restriction enzyme digestion sites incorporated in the 5' and 3' ends. The PCR products can then be enzyme digested, purified, and inserted into the corresponding sites of prokaryotic expression vector in-frame to generate recombinant plasmids. Sequence fidelity of this recombinant DNA can be verified by sequencing. The prokaryotic recombinant plasmids may be transformed into host cells (e.g., *E. coli* BL21 (DE3)). Recombinant protein synthesis may be stimulated by the addition of 0.4 mM isopropylthiogalactoside (IPTG) for 3 h. The bacterially-expressed proteins may be purified.

The polypeptide of the gene variant may be expressed in animal cells by using eukaryotic expression vectors. Cells may be maintained in Dulbecco's modified Eagle's medium (DMEM) supplemented with 10% fetal bovine serum (FBS; GIBCO® BRL) at 37° C. in a humidified 5% CO2 atmosphere. Before transfection, the nucleotide sequence of each of the gene variant may be amplified with PCR primers containing restriction enzyme digestion sites and ligated into the corresponding sites of eukaryotic expression vector in-frame. Sequence fidelity of this recombinant DNA can be verified by sequencing. The cells may be plated in 12-well plates one day before transfection at a density of 5×104 cells per well. Transfections may be carried out using Lipofectaminutese Plus transfection reagent according to the manufacturer's instructions (GIBCO® BRL). Three hours following transfection, medium containing the complexes may be replaced with fresh medium. Forty-eight hours after incubation, the cells may be scraped into lysis buffer (0.1 M Tris HCl, pH 8.0, 0.1% Triton X-100) for purification of expressed proteins. After these proteins are purified, monoclonal antibodies against these purified proteins (Ron-V1, Ron-V2, and Ron-V3) may be generated using hybridoma technique according to the conventional methods (de StGroth and Scheidegger, (1980) J Immunol Methods 35:1-21; Cote et al. (1983) Proc Natl Acad Sci USA 80: 2026-30; and Kozbor et al. (1985) J Immunol Methods 81:31-42).

According to the present invention, the presence of the polypeptides of Ron-V1, Ron-V2, and Ron-V3 in samples of the breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma may be determined by a Western blot analysis. Proteins extracted from samples may be separated by SDS-PAGE and transferred to suitable membranes such as polyvinylidene difluoride (PVDF) in transfer buffer (25 mM Tris-HCl, pH 8.3, 192 mM glycine, 20% methanol) with a Trans-Blot apparatus for 1 h at 100 V (e.g., Bio-Rad). The proteins can be immunoblotted with specific antibodies. For example, membrane blotted with extracted proteins may be blocked with suitable buffers such as 3% solution of BSA or 3% solution of nonfat milk powder in TBST buffer (10 mM Tris-HCl, pH 8.0, 150 mM NaCl, 0.1% Tween 20) and incubated with monoclonal antibody directed against the polypeptides of gene variants. Unbound antibody is removed by washing with TBST for 5×1 minutes. Bound antibody may be detected using commercial ECL Western blotting detecting reagents.

The following examples are provided for illustration, but not for limiting the invention.

EXAMPLES

Analysis of Human Colon Adenocarcinoma EST Database

Expressed sequence tags (ESTs) generated from the large-scale PCR-based sequencing of the 5'-end of human colon adenocarcinoma cDNA clones were compiled and served as EST databases. Sequence comparisons against the nonredundant nucleotide and protein databases were performed using BLASTN and BLASTX programs, at the National Center for Biotechnology Information (NCBI™) with a significance cutoff of p<10-10. ESTs representing putative Ron-V1, Ron-V2, and Ron-V3 genes were identified during the course of EST generation.

Isolation of cDNA Clones

Three cDNA clones exhibiting EST sequences similar to the Ron gene were isolated from the human colon adenocarcinoma cDNA library and named Ron-V1, Ron-V2, and Ron-V3. The inserts of these clones were subsequently excised in vivo from the λZAP Express vector using the EXASSIST™/ XLOLR helper phage system (STRATAGENE®). Phagemid particles were excised by coinfecting XL1-BLUE MRF' cells with EXASSIST™ helper phage. The excised pBluescript phagemids were used to infect *E. coli* XLOLR cells, which lack the amber suppressor necessary for EXASSIST™ phage replication. Infected XLOLR cells were selected using kanamycin resistance. Resultant colonies contained the double stranded phagemid vector with the cloned cDNA insert. A single colony was grown overnight in LB-kanamycin, and DNA was purified using a QIAGEN® plasmid purification kit.

Full Length Nucleotide Sequencing and Database Comparisons

Phagemid DNA was sequenced using the Taq dye-deoxy terminator cycle sequencing kit for the APPLIED BIOSYSTEMS 377™ sequencing system (PERKINELMER® Life Sciences). Using the primer-walking approach, full-length sequence was determined. Nucleotide and protein searches were performed using BLAST against the non-redundant database of NCBI™.

In Silico Sequence Similarity Analysis

The coding sequence for each cDNA clones was searched against the dbEST sequence database using the BLAST algorithm at the NCBI™ website. ESTs derived from dbEST sequence database were used as a source of information for transcript sequence similarity analysis. The accession numbers of the ESTs matching to the deleted sequence of Ron-V1, Ron-V2, and Ron-V3 were identified.

RT-PCR Expression Pattern Analysis

The expression patterns of Ron-V1, Ron-V2, and Ron-V3 were conducted in human cell lines using RT-PCR. The human cell lines were WI38 (Lung, fetus); A549 (Lung adenocarcinoma); H661 (Large cell carcinoma, lung); H520 (Squamous cell carcinoma, lung); H209 (Small cell carcinoma, lung); JHH-4 (Hepatoma); SUP-T1 (T-cell lymophoblastic lymphoma); Daudi (Burkitt's lymophoma); Ramos (Burkitt's lymophoma); RAJI (Burkitt's lymophoma); ZR75-1 (Breast carcinoma); MDA-MB-231 (Breast adenocarcinoma); Hs 578T (Breast carcinoma); G5T/VGH (Glioblastoma multiforme); TSGH9201 (Gastric carcinoma); Ca Ski (Cervix epidermoid carcinoma); Hela S3 (Cervical epitheloid carcinoma); COLO 320 HSR (Colon adenocarcinoma); SW620 (Colon adenocarcinoma); TSGH8301 (Urinary bladder carcinoma); ES-2 (Ovarian carcinoma); DU145 (Brain prostate carcinoma); MIA paca-2 (Pancreatic carcinoma); CE48T/VGH (Esophagus epidermoid carcinoma); CE81T/VGH (Esophagus carcinoma well differentiated aquamous); HL-CZ (Promonocytic leukemia); Hs 181.tes (Normal testis). The purity and integrity of total RNA extracted from each of the cell lines were assessed by absorbance at 260/280 nm and by agarose gel electrophoresis. The forward and reverse primers for Ron gene variants were: (SEQ ID NO: 9) 5'-GACTGAGTGTCTGCTAGCACGG-3' and (SEQ ID NO: 10) 5'-ATGGCAGGGAGTGCATC-TACGC-3'. The expected size of Ron-V1, Ron-V2, and Ron-V3 PCR fragments were 660 bp, 540 bp and 513 bp.

Glyceraldehyde-3-phosphate dehydrogenase (GAPDH; accession No. M33197) was used for internal control. The forward and reverse primers for GAPDH were: (SEQ ID NO: 11) 5'-TGGGTGTGAACCATGAGAAG-3' and (SEQ ID NO: 12) 5'-GTGTCGCTGTTGAAGTCAGA-3'. The expected size of GAPDH PCR fragment was 472 bp. Briefly, a 50 μl reaction mixture containing 2 μl total RNA (0.1 μg/μl), 1 μl each primer (20 pM), 1 μl each dNTP (10 mM), 2.5 μl DTT solution (100 mM), 10 μl 5×RT-PCR buffer, 1 μl enzyme mixture and 28.5 μl sterile redistilled water were subjected to reverse transcription at 60° C. for 30 min followed by 35 cycles of denaturation at 94° C. for 2 min, annealing at 60° C. for 2 min, and extension at 68° C. for 2 min. Five microliters (10%) of the amplified products mixed with 1 μl of loading buffer were separated on a 1% horizontal agarose gel stained with ethidium bromide in 0.5×TAE buffer. The gel was electrophoresed at 100 V for 45 min.

FIG. 7 showed that Ron-V1 (660 bp), Ron-V2 (540 bp), and Ron-V3 (513 bp) mRNAs were RT-PCR amplified using the primers described above. Shown on the left are 100 bp DNA ladder markers. The PCR fragments of Ron-V1 (660 bp), Ron-V2 (540 bp), and Ron-V3 (513 bp) were confirmed by sequencing. Ron-V1 mRNA was expressed in the cell lines of cervix epitheloid carcinoma, colon adenocarcinoma, urinary bladder carcinoma, prostate carcinoma, esophagus carcinoma, and esophagus epidermoid carcinoma; Ron-V2 mRNA was expressed in the cell lines of breast carcinoma, breast adenocarcinoma, cervix epidermoid carcinoma, colon adenocarcinoma, and urinary bladder carcinoma; Ron-V3 mRNA was expressed in the cell lines of breast carcinoma, colon adenocarcinoma, urinary bladder carcinoma, esophagus carcinoma, and esophagus epidermoid carcinoma. The differential expression pattern among Ron-V1, Ron-V2, and Ron-V3 implied that they may be functionally different and may be a suitable marker for diagnosing human breast carcinoma, breast adenocarcinoma, cervix epidermoid carcinoma, cervix epitheloid carcinoma, colon adenocarcinoma, urinary bladder carcinoma, prostate carcinoma, esophagus epidermoid carcinoma and esophagus carcinoma.

REFERENCES

All references are listed herein for the convenience of the reader. Each is incorporated by reference in its entirety.
1. Angeloni et al., The soluble sema domain of the RON receptor inhibits macrophage-stimulating protein-induced receptor activation. J. Biol. Chem. 279:3726-32, (2004).
2. Camp et al., RON, a tyrosine kinase receptor involved in tumor progression and metastasis. Ann Surg Oncol. 12:273-81, (2005).
3. Peace et al., Ron receptor signaling augments mammary tumor formation and metastasis in a murine model of breast cancer. Cancer Res. 65:1285-93, (2005).
4. Wang et al., Oncogenic and invasive potentials of human macrophage-stimulating protein receptor, the RON receptor tyrosine kinase. Carcinogenesis 24:1291-300, (2003).
5. Willett et al., Differential screening of a human chromosome 3 library identifies hepatocyte growth factor-like/macrophage-stimulating protein and its receptor in injured lung. Possible implications for neuroendocrine cell survival. J Clin Invest. 99:2979-91, (1997).

The invention claimed is:

1. An isolated nucleic acid encoding the amino acid sequence of SEQ ID NO: 8.

2. The isolated nucleic acid of claim 1, comprising the nucleotide sequence of SEQ ID NO: 7.

3. An expression vector comprising the nucleic acid of claim 1 or 2.

* * * * *

SEQUENCE LISTING

<160> NUMBER OF SEQ ID NOS: 12

<210> SEQ ID NO 1
<211> LENGTH: 4541
<212> TYPE: DNA
<213> ORGANISM: Homo sapiens

<400> SEQUENCE: 1
ggatcctcta gggtcccagc tcgcctcgat ggagctcctc ccgccgctgc ctcagtcctt      60

```
cctgttgctg ctgctgttgc ctgccaagcc cgcggcgggc gaggactggc agtgcccgcg    120 cacccccctac gcggcctctc gcgactttga cgtgaagtac gtggtgccca gcttctccgc    180
cggaggcctg gtacaggcca tggtgaccta cgagggcgac agaaatgaga gtgctgtgtt    240
tgtagccata cgcaatcgcc tgcatgtgct tgggcctgac ctgaagtctg tccagagcct    300
ggccacgggc cctgctggag accctggctg ccagacgtgt gcagcctgtg cccaggacc     360 ccacggccct cccggtgaca cagacacaaa ggtgctggtg ctggatcccg cgctgcctgc    420
gctggtcagt tgtggctcca gcctgcaggg ccgctgcttc ctgcatgacc tagagcccca    480
agggacagcc gtgcatctgg cagcgccagc ctgcctcttc tcagcccacc ataaccggcc    540
cgatgactgc cccgactgtg tggccagccc attgggcacc cgtgtaactg tggttgagca    600
aggccaggcc tcctatttct acgtggcatc ctcactggac gcagccgtgg ctggcagctt    660
cagcccacgc tcagtgtcta tcaggcgtct caaggctgac gcctcgggat tcgcaccggg    720
ctttgtggcg ttgtcagtgc tgcccaagca tcttgtctcc tacagtattg aatacgtgca    780
cagcttccac acgggagcct tcgtatactt cctgactgta cagccggcca gcgtgacaga    840
tgatcctagt gccctgcaca cacgcctggc acggcttagc gccactgagc cagagttggg    900
tgactatcgg gagctggtcc tcgactgcag atttgctcca aaacgcaggc gccggggggc    960
cccagaaggc ggacagccct accctgtgct gcaggtggcc cactccgctc cagtgggtgc    1020
ccaacttgcc actgagctga gcatcgccga gggccaggaa gtactatttg ggtctttgt     1080 gactggcaag gatggtggtc ctggcgtggg ccccaactct gtcgtctgtg ccttcccat     1140 tgacctgctg gacacactaa ttgatgaggg tgtggagcgc tgttgtgaat ccccagtcca    1200
tccaggcctc cggcgaggcc tcgacttctt ccagtcgccc agttttttgcc ccaacccgcc    1260 tggcctggaa gccctcagcc caacaccag ctgccgccac ttccctctgc tggtcagtag      1320
cagcttctca cgtgtggacc tattcaatgg gctgttggga ccagtacagg tcactgcatt    1380
gtatgtgaca cgccttgaca acgtcacagt ggcacacatg ggcacaatgg atgggcgtat    1440
cctgcaggtg gagctggtca ggtcactaaa ctacttgctg tatgtgtcca acttctcact    1500
gggtgacagt gggcagcccg tgcagcggga tgtcagtcgt cttggggacc acctactctt    1560
tgcctctggg gaccaggttt tccaggtacc tatccgaggc cctggctgcc gccacttcct    1620
gacctgtggg cgttgcctaa gggcatggca tttcatgggc tgtggctggt gtgggaacat    1680
gtgcggccag cagaaggagt gtcctggctc ctggcaacag gaccactgcc cacctaagct    1740
tactgagttc cacccccaca gtggacctct aaggggcagt acaaggctga ccctgtgtgg    1800
ctccaacttc taccttcacc cttctggtct ggtgcctgag ggaacccatc aggtcactgt    1860
gggccaaagt ccctgccggc cactgcccaa ggacagctca aaactcagac cagtgccccg    1920
gaaagacttt gtagaggagt ttgagtgtga actggagccc ttgggcaccc aggcagtggg    1980
gcctaccaac gtcagcctca ccgtgactaa catgccaccg ggcaagcact tccgggtaga    2040
cggcacctcc gtgctgagag gcttctcttt catggagcca gtgctgatag cagtgcaacc    2100 cctcttggc ccacgggcag gaggcacctg tctcactctt gaaggccaga gtctgtctgt      2160
aggcaccagc cgggctgtgc tggtcaatgg gactgagtgt ctgctagcac gggtcagtga    2220
ggggcagctt ttatgtgcca caccccctgg ggccacggtg gccagtgtcc cccttagcct    2280
gcaggtgggg ggtgcccagg tacctggttc ctggaccttc cagtacagag aagaccctgt    2340
cgtgctaagc atcagcccca actgtggcta catcaactcc cacatcacca tctgtggcca    2400
gcatctaact tcagcatggc acttagtgct gtcattccat gacgggctta gggcagtgga    2460
```

```
aagcaggtgt gagaggcagc ttccagagca gcagctgtgc cgccttcctg aatatgtggt    2520
ccgagacccc cagggatggg tggcagggaa tctgagtgcc cgaggggatg gagctgctgg    2580
ctttacactg cctggctttc gcttcctacc cccaccccat ccacccagtg ccaacctagt    2640
tccactgaag cctgaggagc atgccattaa gtttgagtat attgggctgg gcgctgtggc    2700
tgactgtgtg ggtatcaacg tgaccgtggg tggtgagagc tgccagcacg agttccgggg    2760
ggacatggtt gtctgccccc tgccccatc cctgcagctt ggccaggatg gtgcccatt    2820 gcaggtctgc gtagatggtg aatgtcatat cctgggtaga gtggtgcggc cagggccaga    2880
tggggtccca cagagcacgc tccttggtat cctgctgcct ttgctgctgc ttgtggctgc    2940
actggcgact gcactggtct tcagctactg gtggcggagg aagcagctag ttcttcctcc    3000
caacctgaat gacctggcat ccctggacca gactgctgga gccacacccc tgcctattct    3060
gtactcgggc tctgactaca gaagtggcct tgcactccct gccattgatg gtctggattc    3120
caccacttgt gtccatggag catccttctc cgatagtgaa gatgaatcct gtgtgccact    3180
gctgcggaaa gagtccatcc agctaaggga cctggactct cgctcttgg ctgaggtcaa    3240 ggatgtgctg attccccatg agcgggtggt cacccacagt gaccgagtca ttggcaaagg    3300
ccactttgga gttgtctacc acggagaata catagaccag gcccagaatc gaatccaatg    3360
tgccatcaag tcactaagtc gcatcacaga gatgcagcag gtggaggcct tcctgcgaga    3420
ggggctgctc atgcgtggcc tgaaccaccc gaatgtgctg gctctcattg gtatcatgtt    3480
gccacctgag ggcctgcccc atgtgctgct gccctatatg tgccacggtg acctgctcca    3540
gttcatccgc tcacctcagc ggaaccccac cgtgaaggac ctcatcagct ttggcctgca    3600
ggtagcccgc ggcatggagt acctggcaga gcagaagttt gtgcacaggg acctggctgc    3660
gcggaactgc atgctggacg agtcattcac agtcaaggtg gctgactttg gtttggcccg    3720
cgacatcctg gacagggagt actatagtgt tcaacagcat cgccacgctc gcctacctgt    3780
gaagtggatg gcgctggaga gcctgcagac ctatagattt accaccaagt ctgatgtgtg    3840
gtcatttggt gtgctgctgt gggaactgct gacacgggt gccccaccat accgccacat    3900
tgaccctttt gaccttaccc acttcctggc ccagggtcgg cgcctgcccc agcctgagta    3960
ttgccctgat tctctgtacc aagtgatgca gcaatgctgg gaggcagacc cagcagtgcg    4020
acccaccttc agagtactag tgggggaggt ggagcagata gtgtctgcac tgcttgggga    4080
ccattatgtg cagctgccag caacctacat gaacttgggc cccagcacct cgcatgagat    4140
gaatgtgcgt ccagaacagc cgcagttctc acccatgcca gggaatgtac gccggccccg    4200
gccactctca gagcctcctc ggcccacttg acttagttct tggctgtgac ctgcttagct    4260
gccttgagct aaccccaagg ctgcctctgg gccatgccag gccagagcag tggccctcca    4320
ccttgttcct gcccttaac tttcagaggc aataggtaaa tgggcccatt aggtccctca    4380
ctccacagag tgagccagtg agggcagtcc tgcaacatgt atttatggag tgcctgctgt    4440
ggaccctgtc ttctgggcac agtggactca gcagtgacca caccaacact gacccttgaa    4500
ccaataaagg aacaaatgac tattaaagca caaaaaaaaa a                         4541
```

<210> SEQ ID NO 2
<211> LENGTH: 1400
<212> TYPE: PRT
<213> ORGANISM: Homo sapiens

<400> SEQUENCE: 2

Met Glu Leu Leu Pro Pro Leu Pro Gln Ser Phe Leu Leu Leu Leu Leu

```
               1               5                  10                 15
Leu Pro Ala Lys Pro Ala Ala Gly Glu Asp Trp Gln Cys Pro Arg Thr
                20                 25                 30

Pro Tyr Ala Ala Ser Arg Asp Phe Asp Val Lys Tyr Val Val Pro Ser
                35                 40                 45

Phe Ser Ala Gly Gly Leu Val Gln Ala Met Val Thr Tyr Glu Gly Asp
 50                     55                  60

Arg Asn Glu Ser Ala Val Phe Val Ala Ile Arg Asn Arg Leu His Val
 65                     70                  75                  80

Leu Gly Pro Asp Leu Lys Ser Val Gln Ser Leu Ala Thr Gly Pro Ala
                85                 90                 95

Gly Asp Pro Gly Cys Gln Thr Cys Ala Ala Cys Gly Pro Gly Pro His
                100                105                110

Gly Pro Pro Gly Asp Thr Asp Thr Lys Val Leu Val Leu Asp Pro Ala
                115                120                125

Leu Pro Ala Leu Val Ser Cys Gly Ser Ser Leu Gln Gly Arg Cys Phe
                130                135                140

Leu His Asp Leu Glu Pro Gln Gly Thr Ala Val His Leu Ala Ala Pro
145                 150                155                 160

Ala Cys Leu Phe Ser Ala His His Asn Arg Pro Asp Asp Cys Pro Asp
                165                170                175

Cys Val Ala Ser Pro Leu Gly Thr Arg Val Thr Val Val Glu Gln Gly
                180                185                190

Gln Ala Ser Tyr Phe Tyr Val Ala Ser Ser Leu Asp Ala Ala Val Ala
                195                200                205

Gly Ser Phe Ser Pro Arg Ser Val Ser Ile Arg Arg Leu Lys Ala Asp
                210                215                220

Ala Ser Gly Phe Ala Pro Gly Phe Val Ala Leu Ser Val Leu Pro Lys
225                 230                235                 240

His Leu Val Ser Tyr Ser Ile Glu Tyr Val His Ser Phe His Thr Gly
                245                250                255

Ala Phe Val Tyr Phe Leu Thr Val Gln Pro Ala Ser Val Thr Asp Asp
                260                265                270

Pro Ser Ala Leu His Thr Arg Leu Ala Arg Leu Ser Ala Thr Glu Pro
                275                280                285

Glu Leu Gly Asp Tyr Arg Glu Leu Val Leu Asp Cys Arg Phe Ala Pro
                290                295                300

Lys Arg Arg Arg Arg Gly Ala Pro Glu Gly Gly Gln Pro Tyr Pro Val
305                 310                315                 320

Leu Gln Val Ala His Ser Ala Pro Val Gly Ala Gln Leu Ala Thr Glu
                325                330                335

Leu Ser Ile Ala Glu Gly Gln Glu Val Leu Phe Gly Val Phe Val Thr
                340                345                350

Gly Lys Asp Gly Gly Pro Gly Val Gly Pro Asn Ser Val Val Cys Ala
                355                360                365

Phe Pro Ile Asp Leu Leu Asp Thr Leu Ile Asp Glu Gly Val Glu Arg
                370                375                380

Cys Cys Glu Ser Pro Val His Pro Gly Leu Arg Arg Gly Leu Asp Phe
385                 390                395                 400

Phe Gln Ser Pro Ser Phe Cys Pro Asn Pro Pro Gly Leu Glu Ala Leu
                405                410                415

Ser Pro Asn Thr Ser Cys Arg His Phe Pro Leu Leu Val Ser Ser Ser
                420                425                430
```

```
Phe Ser Arg Val Asp Leu Phe Asn Gly Leu Gly Pro Val Gln Val
        435                 440                 445

Thr Ala Leu Tyr Val Thr Arg Leu Asp Asn Val Thr Val Ala His Met
450             455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510

Ser Gly Asp Gln Val Phe Gln Val Pro Ile Arg Gly Pro Gly Cys Arg
        515                 520                 525

His Phe Leu Thr Cys Gly Arg Cys Leu Arg Ala Trp His Phe Met Gly
    530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
                565                 570                 575

His Ser Gly Pro Leu Arg Gly Ser Thr Arg Leu Thr Leu Cys Gly Ser
            580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
    610                 615                 620

Lys Leu Arg Pro Val Pro Arg Lys Asp Phe Val Glu Phe Glu Cys
625                 630                 635                 640

Glu Leu Glu Pro Leu Gly Thr Gln Ala Val Gly Pro Thr Asn Val Ser
                645                 650                 655

Leu Thr Val Thr Asn Met Pro Pro Gly Lys His Phe Arg Val Asp Gly
            660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Gly Thr Cys Leu Thr Leu
    690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
                725                 730                 735

Ala Thr Pro Pro Gly Ala Thr Val Ala Ser Val Pro Leu Ser Leu Gln
            740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
    770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
            820                 825                 830

Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro Pro His
    850                 855                 860
```

```
Pro Pro Ser Ala Asn Leu Val Pro Leu Lys Pro Glu Glu His Ala Ile
865                 870                 875                 880

Lys Phe Glu Tyr Ile Gly Leu Gly Ala Val Ala Asp Cys Val Gly Ile
                885                 890                 895

Asn Val Thr Val Gly Gly Glu Ser Cys Gln His Glu Phe Arg Gly Asp
            900                 905                 910

Met Val Val Cys Pro Leu Pro Pro Ser Leu Gln Leu Gly Gln Asp Gly
        915                 920                 925

Ala Pro Leu Gln Val Cys Val Asp Gly Glu Cys His Ile Leu Gly Arg
    930                 935                 940

Val Val Arg Pro Gly Pro Asp Gly Val Pro Gln Ser Thr Leu Leu Gly
945                 950                 955                 960

Ile Leu Leu Pro Leu Leu Leu Leu Val Ala Ala Leu Ala Thr Ala Leu
                965                 970                 975

Val Phe Ser Tyr Trp Trp Arg Arg Lys Gln Leu Val Leu Pro Pro Asn
            980                 985                 990

Leu Asn Asp Leu Ala Ser Leu Asp Gln Thr Ala Gly Ala Thr Pro Leu
        995                 1000                1005

Pro Ile Leu Tyr Ser Gly Ser Asp Tyr Arg Ser Gly Leu Ala Leu
    1010                1015                1020

Pro Ala Ile Asp Gly Leu Asp Ser Thr Thr Cys Val His Gly Ala
    1025                1030                1035

Ser Phe Ser Asp Ser Glu Asp Glu Ser Cys Val Pro Leu Leu Arg
    1040                1045                1050

Lys Glu Ser Ile Gln Leu Arg Asp Leu Asp Ser Ala Leu Leu Ala
    1055                1060                1065

Glu Val Lys Asp Val Leu Ile Pro His Glu Arg Val Val Thr His
    1070                1075                1080

Ser Asp Arg Val Ile Gly Lys Gly His Phe Gly Val Val Tyr His
    1085                1090                1095

Gly Glu Tyr Ile Asp Gln Ala Gln Asn Arg Ile Gln Cys Ala Ile
    1100                1105                1110

Lys Ser Leu Ser Arg Ile Thr Glu Met Gln Gln Val Glu Ala Phe
    1115                1120                1125

Leu Arg Glu Gly Leu Leu Met Arg Gly Leu Asn His Pro Asn Val
    1130                1135                1140

Leu Ala Leu Ile Gly Ile Met Leu Pro Pro Glu Gly Leu Pro His
    1145                1150                1155

Val Leu Leu Pro Tyr Met Cys His Gly Asp Leu Leu Gln Phe Ile
    1160                1165                1170

Arg Ser Pro Gln Arg Asn Pro Thr Val Lys Asp Leu Ile Ser Phe
    1175                1180                1185

Gly Leu Gln Val Ala Arg Gly Met Glu Tyr Leu Ala Glu Gln Lys
    1190                1195                1200

Phe Val His Arg Asp Leu Ala Ala Arg Asn Cys Met Leu Asp Glu
    1205                1210                1215

Ser Phe Thr Val Lys Val Ala Asp Phe Gly Leu Ala Arg Asp Ile
    1220                1225                1230

Leu Asp Arg Glu Tyr Tyr Ser Val Gln Gln His Arg His Ala Arg
    1235                1240                1245

Leu Pro Val Lys Trp Met Ala Leu Glu Ser Leu Gln Thr Tyr Arg
    1250                1255                1260

Phe Thr Thr Lys Ser Asp Val Trp Ser Phe Gly Val Leu Leu Trp
```

| | | | | | | | | | |
|---|---|---|---|---|---|---|---|---|---|
| | | 1265 | | | 1270 | | | 1275 | |
| Glu | Leu | Leu | Thr | Arg | Gly | Ala | Pro | Pro | Tyr | Arg | His | Ile | Asp | Pro |
| | 1280 | | | | 1285 | | | | 1290 | |

Phe Asp Leu Thr His Phe Leu Ala Gln Gly Arg Arg Leu Pro Gln
 1295                1300                1305

Pro Glu Tyr Cys Pro Asp Ser Leu Tyr Gln Val Met Gln Gln Cys
 1310                1315                1320

Trp Glu Ala Asp Pro Ala Val Arg Pro Thr Phe Arg Val Leu Val
 1325                1330                1335

Gly Glu Val Glu Gln Ile Val Ser Ala Leu Leu Gly Asp His Tyr
 1340                1345                1350

Val Gln Leu Pro Ala Thr Tyr Met Asn Leu Gly Pro Ser Thr Ser
 1355                1360                1365

His Glu Met Asn Val Arg Pro Glu Gln Pro Gln Phe Ser Pro Met
 1370                1375                1380

Pro Gly Asn Val Arg Arg Pro Arg Pro Leu Ser Glu Pro Pro Arg
 1385                1390                1395

Pro Thr
 1400

<210> SEQ ID NO 3
<211> LENGTH: 4000
<212> TYPE: DNA
<213> ORGANISM: Homo sapiens

<400> SEQUENCE: 3

```
ggatcctcta gggtcccagc tcgcctcgat ggagctcctc ccgccgctgc ctcagtcctt      60
cctgttgctg ctgctgttgc ctgccaagcc cgcggcgggc gaggactggc agtgcccgcg     120
caccccctac gcggcctctc gcgactttga cgtgaagtac gtggtgccca gcttctccgc     180
cggaggcctg gtacaggcca tggtgaccta cgagggcgac agaaatgaga gtgctgtgtt     240
tgtagccata cgcaatcgcc tgcatgtgct tgggcctgac ctgaagtctg tccagagcct     300
ggccacgggc cctgctggag accctggctg ccagacgtgt gcagcctgtg cccaggacc     360
ccacggccct cccggtgaca cagacacaaa ggtgctggtg ctggatcccg cgctgcctgc     420
gctggtcagt tgtggctcca gcctgcaggg ccgctgcttc ctgcatgacc tagagcccca     480
agggacagcc gtgcatctgg cagcgccagc ctgcctcttc tcagcccacc ataaccggcc     540
cgatgactgc cccgactgtg tggccagccc attgggcacc cgtgtaactg tggttgagca     600
aggccaggcc tcctatttct acgtggcatc ctcactggac gcagccgtgg ctggcagctt     660
cagcccacgc tcagtgtcta tcaggcgtct caaggctgac gcctcgggat cgcaccggg      720
ctttgtggcg ttgtcagtgc tgcccaagca tcttgtctcc tacagtattg aatacgtgca     780
cagcttccac acgggagcct tcgtatactc cctgactgta cagccggcca gcgtgacaga     840
tgatcctagt gccctgcaca cacgcctggc acggcttagc gccactgagc cagagttggg     900
tgactatcgg gagctggtcc tcgactgcag atttgctcca aaacgcaggc gccgggggc      960
cccagaaggc ggacagccct accctgtgct gcaggtggcc cactccgctc cagtgggtgc    1020
ccaacttgcc actgagctga gcatcgccga gggccaggaa gtactatttg gggtctttgt    1080
gactggcaag gatggtggtc ctggcgtggg ccccaactct gtcgtctgtg ccttccccat    1140
tgacctgctg gacacactaa ttgatgaggg tgtggagcgc tgttgtgaat cccccagtcca    1200
tccaggcctc cggcgaggcc tcgacttctt ccagtcgccc agttttttgcc ccaacccgcc    1260
tggcctggaa gccctcagcc ccaacaccag ctgccgccac ttccctctgc tggtcagtag    1320
```

```
cagcttctca cgtgtggacc tattcaatgg gctgttggga ccagtacagg tcactgcatt    1380
gtatgtgaca cgccttgaca acgtcacagt ggcacacatg ggcacaatgg atgggcgtat    1440
cctgcaggtg gagctggtca ggtcactaaa ctacttgctg tatgtgtcca acttctcact    1500
gggtgacagt gggcagcccg tgcagcggga tgtcagtcgt cttggggacc acctactctt    1560
tgcctctggg gaccaggttt tccaggtacc tatccgaggc cctggctgcc gccacttcct    1620
gacctgtggg cgttgcctaa gggcatggca tttcatgggc tgtggctggt gtgggaacat    1680
gtgcggccag cagaaggagt gtcctggctc ctggcaacag gaccactgcc cacctaagct    1740
tactgagttc cacccccaca gtggacctct aaggggcagt acaaggctga ccctgtgtgg    1800
ctccaacttc taccttcacc cttctggtct ggtgcctgag ggaacccatc aggtcactgt    1860
gggccaaagt ccctgccggc cactgcccaa ggacagctca aaactcagac cagtgccccg    1920
gaaagacttt gtagaggagt ttgagtgtga actggagccc ttgggcaccc aggcagtggg    1980
gcctaccaac gtcagcctca ccgtgactaa catgccaccg gcaagcact tccgggtaga    2040 cggcacctcc gtgctgagag gcttctcttt catggagcca gtgctgatag cagtgcaacc    2100
cctctttggc ccacgggcag gaggcacctg tctcactctt gaaggccaga gtctgtctgt    2160
aggcaccagc cgggctgtgc tggtcaatgg gactgagtgt ctgctagcac gggtcagtga    2220
ggggcagctt ttatgtgcca cacccccctgg gccacggtg gccagtgtcc cccttagcct    2280
gcaggtgggg ggtgcccagg tacctggttc ctggaccttc cagtacagag aagaccctgt    2340
cgtgctaagc atcagcccca actgtggcta catcaactcc cacatcacca tctgtggcca    2400
gcatctaact tcagcatggc acttagtgct gtcattccat gacgggctta gggcagtgga    2460
aagcaggtgt gagaggcagc ttccagagca gcagctgtgc cgccttcctg aatatgtggt    2520
ccgagacccc cagggatggg tggcagggaa tctgagtgcc cgaggggatg gagctgctgg    2580
ctttacactg cctggctttc gcttcctacc cccacccat ccaccagtg ccaacctagt    2640 tccactgaag cctgaggagc atgccattaa gtttgagtat attgggctgg gcgctgtggc    2700
tgactgtgtg ggtatcaacg tgaccgtggg tggtgagagc tgccagcacg agttccgggg    2760
ggacatggtt gtctgccccc tgccccatc cctgcagctt ggccaggatg gtgccccatt    2820
gcaggtctgc gtagatgcac tccctgccat tgatggtctg gattccacca cttgtgtcca    2880
tggagcatcc ttctccgata gtgaagatga atcctgtgtg ccactgctgc ggaaagagtc    2940
catccagcta agggacctgg actctgcgct cttggctgag gtcaaggatg tgctgattcc    3000
ccatgagcgg gtggtcaccc acagtgaccg agtcattggc aaaggccact ttggagttgt    3060
ctaccacgga gaatacatag accaggccca gaatcgaatc caatgtgcca tcaagtcact    3120
aagtcgcatc acagagatgc agcaggtgga ggccttcctg cgagaggggc tgctcatgcg    3180
tggcctgaac cacccgaatg tgctggctct cattggtatc atgttgccac ctgagggcct    3240
gccccatgtg ctgctgccct atatgtgcca cggtgacctg ctccagttca tccgctcacc    3300
tcagcggaac cccaccgtga aggacctcat cagctttggc ctgcaggtag cccgcggcat    3360
ggagtacctg gcagagcaga gtttgtgca cagggacctg gctgcgcgga actgcatgct    3420
ggacgagtca ttcacagtca aggtggctga ctttggtttg gcccgcgaca tcctggacag    3480
ggagtactat agtgttcaac agcatcgcca cgctcgccta cctgtgaagt ggatggcgct    3540
ggagagcctg cagacctata gatttaccac caagtctgat gtggtaccaa gtgatgcagc    3600
aatgctggga ggcagaccca gcagtgcgac ccaccttcag agtactagtg ggggaggtgg    3660
agcagatagt gtctgcactg cttggggacc attatgtgca gctgccagca acctacatga    3720
```

```
acttgagcta accccaaggc tgcctctggg ccatgccagg ccagagcagt ggccctccac    3780
cttgttcctg ccctttaact ttcagaggca ataggtaaat gggcccatta ggtccctcac    3840
tccacagagt gagccagtga gggcagtcct gcaacatgta tttatggagt gcctgctgtg    3900
gaccctgtct tctgggcaca gtggactcag cagtgaccac accaacactg acccttgaac    3960
caataaagga acaaatgact attaaagcac aaaaaaaaa                           4000
```

<210> SEQ ID NO 4
<211> LENGTH: 1261
<212> TYPE: PRT
<213> ORGANISM: Homo sapiens

<400> SEQUENCE: 4

```
Met Glu Leu Leu Pro Pro Leu Pro Gln Ser Phe Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
```

-continued

```
                325                 330                 335
Leu Ser Ile Ala Glu Gly Gln Glu Val Leu Phe Gly Val Phe Val Thr
                340                 345                 350
Gly Lys Asp Gly Gly Pro Gly Val Gly Pro Asn Ser Val Val Cys Ala
                355                 360                 365
Phe Pro Ile Asp Leu Leu Asp Thr Leu Ile Asp Glu Gly Val Glu Arg
                370                 375                 380
Cys Cys Glu Ser Pro Val His Pro Gly Leu Arg Arg Gly Leu Asp Phe
385                 390                 395                 400
Phe Gln Ser Pro Ser Phe Cys Pro Asn Pro Pro Gly Leu Glu Ala Leu
                405                 410                 415
Ser Pro Asn Thr Ser Cys Arg His Phe Pro Leu Leu Val Ser Ser Ser
                420                 425                 430
Phe Ser Arg Val Asp Leu Phe Asn Gly Leu Leu Gly Pro Val Gln Val
                435                 440                 445
Thr Ala Leu Tyr Val Thr Arg Leu Asp Asn Val Thr Val Ala His Met
                450                 455                 460
Gly Thr Met Asp Gly Arg Ile Leu Gln Val Glu Leu Val Arg Ser Leu
465                 470                 475                 480
Asn Tyr Leu Leu Tyr Val Ser Asn Phe Ser Leu Gly Asp Ser Gly Gln
                485                 490                 495
Pro Val Gln Arg Asp Val Ser Arg Leu Gly Asp His Leu Leu Phe Ala
                500                 505                 510
Ser Gly Asp Gln Val Phe Gln Val Pro Ile Arg Gly Pro Gly Cys Arg
                515                 520                 525
His Phe Leu Thr Cys Gly Arg Cys Leu Arg Ala Trp His Phe Met Gly
                530                 535                 540
Cys Gly Trp Cys Gly Asn Met Cys Gly Gln Gln Lys Glu Cys Pro Gly
545                 550                 555                 560
Ser Trp Gln Gln Asp His Cys Pro Pro Lys Leu Thr Glu Phe His Pro
                565                 570                 575
His Ser Gly Pro Leu Arg Gly Ser Thr Arg Leu Thr Leu Cys Gly Ser
                580                 585                 590
Asn Phe Tyr Leu His Pro Ser Gly Leu Val Pro Glu Gly Thr His Gln
                595                 600                 605
Val Thr Val Gly Gln Ser Pro Cys Arg Pro Leu Pro Lys Asp Ser Ser
                610                 615                 620
Lys Leu Arg Pro Val Pro Arg Lys Asp Phe Val Glu Glu Phe Glu Cys
625                 630                 635                 640
Glu Leu Glu Pro Leu Gly Thr Gln Ala Val Gly Pro Thr Asn Val Ser
                645                 650                 655
Leu Thr Val Thr Asn Met Pro Pro Gly Lys His Phe Arg Val Asp Gly
                660                 665                 670
Thr Ser Val Leu Arg Gly Phe Ser Phe Met Glu Pro Val Leu Ile Ala
                675                 680                 685
Val Gln Pro Leu Phe Gly Pro Arg Ala Gly Gly Thr Cys Leu Thr Leu
                690                 695                 700
Glu Gly Gln Ser Leu Ser Val Gly Thr Ser Arg Ala Val Leu Val Asn
705                 710                 715                 720
Gly Thr Glu Cys Leu Leu Ala Arg Val Ser Glu Gly Gln Leu Leu Cys
                725                 730                 735
Ala Thr Pro Pro Gly Ala Thr Val Ala Ser Val Pro Leu Ser Leu Gln
                740                 745                 750
```

-continued

```
Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
        770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
                805                 810                 815

Gln Leu Pro Glu Gln Gln Leu Cys Arg Leu Pro Glu Tyr Val Val Arg
                820                 825                 830

Asp Pro Gln Gly Trp Val Ala Gly Asn Leu Ser Ala Arg Gly Asp Gly
                835                 840                 845

Ala Ala Gly Phe Thr Leu Pro Gly Phe Arg Phe Leu Pro Pro His
850                 855                 860

Pro Pro Ser Ala Asn Leu Val Pro Leu Lys Pro Glu His Ala Ile
865                 870                 875                 880

Lys Phe Glu Tyr Ile Gly Leu Gly Ala Val Ala Asp Cys Val Gly Ile
                885                 890                 895

Asn Val Thr Val Gly Gly Glu Ser Cys Gln His Glu Phe Arg Gly Asp
            900                 905                 910

Met Val Val Cys Pro Leu Pro Pro Ser Leu Gln Leu Gly Gln Asp Gly
            915                 920                 925

Ala Pro Leu Gln Val Cys Val Asp Ala Leu Pro Ala Ile Asp Gly Leu
930                 935                 940

Asp Ser Thr Thr Cys Val His Gly Ala Ser Phe Ser Asp Ser Glu Asp
945                 950                 955                 960

Glu Ser Cys Val Pro Leu Leu Arg Lys Glu Ser Ile Gln Leu Arg Asp
                965                 970                 975

Leu Asp Ser Ala Leu Leu Ala Glu Val Lys Asp Val Leu Ile Pro His
                980                 985                 990

Glu Arg Val Val Thr His Ser Asp Arg Val Ile Gly Lys Gly His Phe
                995                 1000                1005

Gly Val Val Tyr His Gly Glu Tyr Ile Asp Gln Ala Gln Asn Arg
    1010                1015                1020

Ile Gln Cys Ala Ile Lys Ser Leu Ser Arg Ile Thr Glu Met Gln
    1025                1030                1035

Gln Val Glu Ala Phe Leu Arg Glu Gly Leu Leu Met Arg Gly Leu
    1040                1045                1050

Asn His Pro Asn Val Leu Ala Leu Ile Gly Ile Met Leu Pro Pro
    1055                1060                1065

Glu Gly Leu Pro His Val Leu Pro Tyr Met Cys His Gly Asp
    1070                1075                1080

Leu Leu Gln Phe Ile Arg Ser Pro Gln Arg Asn Pro Thr Val Lys
    1085                1090                1095

Asp Leu Ile Ser Phe Gly Leu Gln Val Ala Arg Gly Met Glu Tyr
    1100                1105                1110

Leu Ala Glu Gln Lys Phe Val His Arg Asp Leu Ala Ala Arg Asn
    1115                1120                1125

Cys Met Leu Asp Glu Ser Phe Thr Val Lys Val Ala Asp Phe Gly
    1130                1135                1140

Leu Ala Arg Asp Ile Leu Asp Arg Glu Tyr Tyr Ser Val Gln Gln
    1145                1150                1155

His Arg His Ala Arg Leu Pro Val Lys Trp Met Ala Leu Glu Ser
    1160                1165                1170
```

| | | | | | | | | | | |
|---|---|---|---|---|---|---|---|---|---|---|
|Leu|Gln|Thr|Tyr|Arg|Phe|Thr|Lys|Ser|Asp|Val|Val|Pro|Ser|
| |1175| | | |1180| | | |1185| | | | |

Leu Gln Thr Tyr Arg Phe Thr Lys Ser Asp Val Val Pro Ser
    1175                1180            1185

Asp Ala Ala Met Leu Gly Gly Arg Pro Ser Ser Ala Thr His Leu
    1190                1195            1200

Gln Ser Thr Ser Gly Gly Gly Gly Ala Asp Ser Val Cys Thr Ala
    1205                1210            1215

Trp Gly Pro Leu Cys Ala Ala Ala Ser Asn Leu His Glu Leu Glu
    1220                1225            1230

Leu Thr Pro Arg Leu Pro Leu Gly His Ala Arg Pro Glu Gln Trp
    1235                1240            1245

Pro Ser Thr Leu Phe Leu Pro Phe Asn Phe Gln Arg Gln
    1250                1255            1260

<210> SEQ ID NO 5
<211> LENGTH: 3880
<212> TYPE: DNA
<213> ORGANISM: Homo sapiens

<400> SEQUENCE: 5

```
ggatcctcta gggtcccagc tcgcctcgat ggagctcctc ccgccgctgc ctcagtcctt     60
cctgttgctg ctgctgttgc ctgccaagcc cgcggcgggc gaggactggc agtgcccgcg    120
cacccccta  cgcggcctctc gcgactttga cgtgaagtac gtggtgccca gcttctccgc    180
cggaggcctg gtacaggcca tggtgaccta cgagggcgac agaaatgaga gtgctgtgtt    240
tgtagccata cgcaatcgcc tgcatgtgct tgggcctgac ctgaagtctg tccagagcct    300
ggccacgggc cctgctggag accctggctg ccagacgtgt gcagcctgtg cccaggacc     360
ccacggccct cccggtgaca cagacacaaa ggtgctggtg ctggatcccg cgctgcctgc    420
gctggtcagt tgtggctcca gcctgcaggg ccgctgcttc ctgcatgacc tagagcccca    480
agggacagcc gtgcatctgg cagcgccagc ctgcctcttc tcagcccacc ataaccggcc    540
cgatgactgc cccgactgtg tggccagccc attgggcacc cgtgtaactg tggttgagca    600
aggccaggcc tcctatttct acgtggcatc ctcactggac gcagccgtgg ctggcagctt    660
cagcccacgc tcagtgtcta tcaggcgtct caaggctgac gcctcgggat cgcaccggg    720
ctttgtggcg ttgtcagtgc tgcccaagca tcttgtctcc tacagtattg aatacgtgca    780
cagcttccac acgggagcct tcgtatactt cctgactgta cagccggcca gcgtgacaga    840
tgatcctagt gccctgcaca cacgcctggc acggcttagc gccactgagc cagagttggg    900
tgactatcgg gagctggtcc tcgactgcag atttgctcca aaacgcaggc gccgggggc    960
cccagaaggc ggacagccct accctgtgct gcaggtggcc cactccgctc cagtgggtgc   1020
ccaacttgcc actgagctga gcatcgccga gggccaggaa gtactatttg gggtctttgt   1080
gactggcaag gatggtggtc ctggcgtggg ccccaactct gtcgtctgtg ccttcccat   1140
tgacctgctg gacacactaa ttgatgaggg tgtggagcgc tgttgtgaat ccccagtcca   1200
tccaggcctc cggcgaggcc tcgacttctt ccagtcgccc agttttttgcc ccaacccgcc   1260
tggcctggaa gccctcagcc ccaacaccag ctgccgccac ttccctctgc tggtcagtag   1320
cagcttctca cgtgtggacc tattcaatgg gctgttggga ccagtacagg tcactgcatt   1380
gtatgtgaca cgccttgaca acgtcacagt ggcacacatg gcacaatgg atgggcgtat   1440
cctgcaggtg gagctggtca ggtcactaaa ctacttgctg tatgtgtcca acttctcact   1500
gggtgacagt gggcagcccg tgcagcggga tgtcagtcgt cttggggacc acctactctt   1560
tgcctctggg gaccaggttt tccaggtacc tatccgaggc cctggctgcc gccacttcct   1620
```

```
gacctgtggg cgttgcctaa gggcatggca tttcatgggc tgtggctggt gtgggaacat    1680
gtgcggccag cagaaggagt gtcctggctc ctggcaacag gaccactgcc cacctaagct    1740
tactgagttc cacccccaca gtggacctct aagggcagt acaaggctga ccctgtgtgg     1800
ctccaacttc taccttcacc cttctggtct ggtgcctgag ggaacccatc aggtcactgt    1860
gggccaaagt ccctgccggc cactgccaa ggacagctca aaactcagac cagtgccccg     1920
gaaagacttt gtagaggagt ttgagtgtga actggagccc ttgggcaccc aggcagtggg    1980
gcctaccaac gtcagcctca ccgtgactaa catgccaccg gcaagcact tccgggtaga     2040
cggcacctcc gtgctgagag cttctctttt catggagcca gtgctgatag cagtgcaacc    2100
cctctttggc ccacgggcag gaggcacctg tctcactctt gaaggccaga gtctgtctgt    2160
aggcaccagc cgggctgtgc tggtcaatgg gactgagtgt ctgctagcac gggtcagtga    2220
ggggcagctt ttatgtgcca cacccctgg ggccacggtg gccagtgtcc cccttagcct     2280
gcaggtgggg ggtgcccagg tacctggttc ctggaccttc cagtacagag aagaccctgt    2340
cgtgctaagc atcagcccca actgtggcta catcaactcc cacatcacca tctgtggcca    2400
gcatctaact tcagcatggc acttagtgct gtcattccat gacgggctta gggcagtgga    2460
aagcaggtgt gagaggcagc ttccagagca gcagctgtgc cgccttcctg aatatgtggt    2520
ccgagacccc cagggatggg tggcaggaa tctgagtgcc cgaggggatg gagctgctgg     2580
ctttacactg cctggctttc gcttcctacc cccaccccat ccacccagtg ccaacctagt    2640
tccactgaag cctgaggagc atgccattaa gtttgagctt ggccaggatg gtgccccatt    2700
gcaggtctgc gtagatgcac tccctgccat tgatggtctg gattccacca cttgtgtcca    2760
tggagcatcc ttctccgata gtgaagatga atcctgtgtg ccactgctgc ggaaagagtc    2820
catccagcta agggacctgg actctgcgct cttggctgag gtcaaggatg tgctgattcc    2880
ccatgagcgg gtggtcaccc acagtgaccg agtcattggc aaaggccact ttggagttgt    2940
ctaccacgga gaatacatag accaggccca gaatcgaatc caatgtgcca tcaagtcact    3000
aagtcgcatc acagagatgc agcaggtgga ggccttcctg cgagaggggc tgctcatgcg    3060
tggcctgaac cacccgaatg tgctggctct cattggtatc atgttgccac ctgagggcct    3120
gccccatgtg ctgctgccct atatgtgcca cggtgacctg ctccagttca tccgctcacc    3180
tcagcggaac cccaccgtga aggacctcat cagctttggc ctgcaggtag cccgcggcat    3240
ggagtacctg gcagagcaga gtttgtgca cagggacctg gctgcgcgga actgcatgct     3300
ggacgagtca ttcacagtca aggtggctga ctttggtttg gcccgcgaca tcctggacag    3360
ggagtactat agtgttcaac agcatcgcca cgctcgccta cctgtgaagt ggatggcgct    3420
ggagagcctg cagacctata gatttaccac caagtctgat gtggtaccaa gtgatgcagc    3480
aatgctggga ggcagaccca gcagtgcgac ccaccttcag agtactagtg ggggaggtgg    3540
agcagatagt gtctgcactg cttggggacc attatgtgca gctgccagca acctacatga    3600
acttgagcta accccaaggc tgcctctggg ccatgccagg ccagagcagt ggccctccac    3660
cttgttcctg ccctttaact ttcagaggca ataggtaaat gggcccatta ggtccctcac    3720
tccacagagt gagccagtga gggcagtcct gcaacatgta tttatggagt gcctgctgtg    3780
gaccctgtct tctgggcaca gtggactcag cagtgaccac accaacactg acccttgaac    3840
caataaagga acaaatgact attaaagcac aaaaaaaaaa                          3880
```

<210> SEQ ID NO 6
<211> LENGTH: 1221

<212> TYPE: PRT
<213> ORGANISM: Homo sapiens

<400> SEQUENCE: 6

```
Met Glu Leu Leu Pro Pro Leu Gln Ser Phe Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80

Leu Gly Pro Asp Leu Lys Ser Val Gln Ser Leu Ala Thr Gly Pro Ala
                85                  90                  95

Gly Asp Pro Gly Cys Gln Thr Cys Ala Ala Cys Gly Pro Gly Pro His
            100                 105                 110

Gly Pro Pro Gly Asp Thr Asp Thr Lys Val Leu Val Leu Asp Pro Ala
        115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400
```

```
Phe Gln Ser Pro Ser Phe Cys Pro Asn Pro Pro Gly Leu Glu Ala Leu
                405                 410                 415
Ser Pro Asn Thr Ser Cys Arg His Phe Pro Leu Leu Val Ser Ser Ser
            420                 425                 430
Phe Ser Arg Val Asp Leu Phe Asn Gly Leu Leu Gly Pro Val Gln Val
        435                 440                 445
Thr Ala Leu Tyr Val Thr Arg Leu Asp Asn Val Thr Val Ala His Met
    450                 455                 460
Gly Thr Met Asp Gly Arg Ile Leu Gln Val Glu Leu Val Arg Ser Leu
465                 470                 475                 480
Asn Tyr Leu Leu Tyr Val Ser Asn Phe Ser Leu Gly Asp Ser Gly Gln
                485                 490                 495
Pro Val Gln Arg Asp Val Ser Arg Leu Gly Asp His Leu Leu Phe Ala
            500                 505                 510
Ser Gly Asp Gln Val Phe Gln Val Pro Ile Arg Gly Pro Gly Cys Arg
        515                 520                 525
His Phe Leu Thr Cys Gly Arg Cys Leu Arg Ala Trp His Phe Met Gly
    530                 535                 540
Cys Gly Trp Cys Gly Asn Met Cys Gly Gln Gln Lys Glu Cys Pro Gly
545                 550                 555                 560
Ser Trp Gln Gln Asp His Cys Pro Pro Lys Leu Thr Glu Phe His Pro
                565                 570                 575
His Ser Gly Pro Leu Arg Gly Ser Thr Arg Leu Thr Leu Cys Gly Ser
            580                 585                 590
Asn Phe Tyr Leu His Pro Ser Gly Leu Val Pro Glu Gly Thr His Gln
        595                 600                 605
Val Thr Val Gly Gln Ser Pro Cys Arg Pro Leu Pro Lys Asp Ser Ser
    610                 615                 620
Lys Leu Arg Pro Val Pro Arg Lys Asp Phe Val Glu Glu Phe Glu Cys
625                 630                 635                 640
Glu Leu Glu Pro Leu Gly Thr Gln Ala Val Gly Pro Thr Asn Val Ser
                645                 650                 655
Leu Thr Val Thr Asn Met Pro Pro Gly Lys His Phe Arg Val Asp Gly
            660                 665                 670
Thr Ser Val Leu Arg Gly Phe Ser Phe Met Glu Pro Val Leu Ile Ala
        675                 680                 685
Val Gln Pro Leu Phe Gly Pro Arg Ala Gly Gly Thr Cys Leu Thr Leu
    690                 695                 700
Glu Gly Gln Ser Leu Ser Val Gly Thr Ser Arg Ala Val Leu Val Asn
705                 710                 715                 720
Gly Thr Glu Cys Leu Leu Ala Arg Val Ser Glu Gly Gln Leu Leu Cys
                725                 730                 735
Ala Thr Pro Pro Gly Ala Thr Val Ala Ser Val Pro Leu Ser Leu Gln
            740                 745                 750
Val Gly Gly Ala Gln Val Pro Gly Ser Trp Thr Phe Gln Tyr Arg Glu
        755                 760                 765
Asp Pro Val Val Leu Ser Ile Ser Pro Asn Cys Gly Tyr Ile Asn Ser
    770                 775                 780
His Ile Thr Ile Cys Gly Gln His Leu Thr Ser Ala Trp His Leu Val
785                 790                 795                 800
Leu Ser Phe His Asp Gly Leu Arg Ala Val Glu Ser Arg Cys Glu Arg
                805                 810                 815
Gln Leu Pro Glu Gln Gln Leu Cys Arg Leu Pro Glu Tyr Val Val Arg
            820                 825                 830
```

```
Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro His
850                 855                 860

Pro Pro Ser Ala Asn Leu Val Pro Leu Lys Pro Glu Glu His Ala Ile
865                 870                 875                 880

Lys Phe Glu Leu Gly Gln Asp Gly Ala Pro Leu Gln Val Cys Val Asp
                885                 890                 895

Ala Leu Pro Ala Ile Asp Gly Leu Asp Ser Thr Thr Cys Val His Gly
                900                 905                 910

Ala Ser Phe Ser Asp Ser Glu Asp Glu Ser Cys Val Pro Leu Leu Arg
                915                 920                 925

Lys Glu Ser Ile Gln Leu Arg Asp Leu Asp Ser Ala Leu Leu Ala Glu
                930                 935                 940

Val Lys Asp Val Leu Ile Pro His Glu Arg Val Val Thr His Ser Asp
945                 950                 955                 960

Arg Val Ile Gly Lys Gly His Phe Gly Val Val Tyr His Gly Glu Tyr
                965                 970                 975

Ile Asp Gln Ala Gln Asn Arg Ile Gln Cys Ala Ile Lys Ser Leu Ser
                980                 985                 990

Arg Ile Thr Glu Met Gln Gln Val Glu Ala Phe Leu Arg Glu Gly Leu
                995                 1000                1005

Leu Met Arg Gly Leu Asn His Pro Asn Val Leu Ala Leu Ile Gly
        1010                1015                1020

Ile Met Leu Pro Pro Glu Gly Leu Pro His Val Leu Leu Pro Tyr
        1025                1030                1035

Met Cys His Gly Asp Leu Leu Gln Phe Ile Arg Ser Pro Gln Arg
        1040                1045                1050

Asn Pro Thr Val Lys Asp Leu Ile Ser Phe Gly Leu Gln Val Ala
        1055                1060                1065

Arg Gly Met Glu Tyr Leu Ala Glu Gln Lys Phe Val His Arg Asp
        1070                1075                1080

Leu Ala Ala Arg Asn Cys Met Leu Asp Glu Ser Phe Thr Val Lys
        1085                1090                1095

Val Ala Asp Phe Gly Leu Ala Arg Asp Ile Leu Asp Arg Glu Tyr
        1100                1105                1110

Tyr Ser Val Gln Gln His Arg His Ala Arg Leu Pro Val Lys Trp
        1115                1120                1125

Met Ala Leu Glu Ser Leu Gln Thr Tyr Arg Phe Thr Thr Lys Ser
        1130                1135                1140

Asp Val Val Pro Ser Asp Ala Ala Met Leu Gly Gly Arg Pro Ser
        1145                1150                1155

Ser Ala Thr His Leu Gln Ser Thr Ser Gly Gly Gly Gly Ala Asp
        1160                1165                1170

Ser Val Cys Thr Ala Trp Gly Pro Leu Cys Ala Ala Ala Ser Asn
        1175                1180                1185

Leu His Glu Leu Glu Leu Thr Pro Arg Leu Pro Leu Gly His Ala
        1190                1195                1200

Arg Pro Glu Gln Trp Pro Ser Thr Leu Phe Leu Pro Phe Asn Phe
        1205                1210                1215

Gln Arg Gln
        1220
```

<210> SEQ ID NO 7
<211> LENGTH: 3853
<212> TYPE: DNA
<213> ORGANISM: Homo sapiens

<400> SEQUENCE: 7

| | | | | | | |
|---|---|---|---|---|---|---|
| ggatcctcta | gggtcccagc | tcgcctcgat | ggagctcctc | ccgccgctgc | ctcagtcctt | 60 |
| cctgttgctg | ctgctgttgc | ctgccaagcc | cgcggcgggc | gaggactggc | agtgcccgcg | 120 |
| cacccctac | gcggcctctc | gcgactttga | cgtgaagtac | gtggtgccca | gcttctccgc | 180 |
| cggaggcctg | gtacaggcca | tggtgaccta | cgagggcgac | agaaatgaga | gtgctgtgtt | 240 |
| tgtagccata | cgcaatcgcc | tgcatgtgct | gggcctgac | ctgaagtctg | tccagagcct | 300 |
| ggccacgggc | cctgctggag | accctggctg | ccagacgtgt | gcagcctgtg | gcccaggacc | 360 |
| ccacggccct | cccggtgaca | cagacacaaa | ggtgctggtg | ctggatcccg | cgctgcctgc | 420 |
| gctggtcagt | tgtggctcca | gcctgcaggg | ccgctgcttc | ctgcatgacc | tagagcccca | 480 |
| agggacagcc | gtgcatctgg | cagcgccagc | ctgcctcttc | tcagcccacc | ataaccggcc | 540 |
| cgatgactgc | cccgactgtg | tggccagccc | attgggcacc | cgtgtaactg | tggttgagca | 600 |
| aggccaggcc | tcctatttct | acgtggcatc | ctcactggac | gcagccgtgg | ctggcagctt | 660 |
| cagcccacgc | tcagtgtcta | tcaggcgtct | caaggctgac | gcctcgggat | tcgcaccggg | 720 |
| ctttgtggcg | ttgtcagtgc | tgcccaagca | tcttgtctcc | tacagtattg | aatacgtgca | 780 |
| cagcttccac | acgggagcct | tcgtatactt | cctgactgta | cagccggcca | gcgtgacaga | 840 |
| tgatcctagt | gccctgcaca | cacgcctggc | acggcttagc | gccactgagc | cagagttggg | 900 |
| tgactatcgg | gagctggtcc | tcgactgcag | atttgctcca | aaacgcaggc | gccggggggc | 960 |
| cccagaaggc | ggacagccct | accctgtgct | gcaggtggcc | cactccgctc | cagtgggtgc | 1020 |
| ccaacttgcc | actgagctga | gcatcgccga | gggccaggaa | gtactatttg | gggtctttgt | 1080 |
| gactggcaag | gatggtggtc | ctggcgtggg | ccccaactct | gtcgtctgtg | ccttccccat | 1140 |
| tgacctgctg | gacacactaa | ttgatgaggg | tgtggagcgc | tgttgtgaat | ccccagtcca | 1200 |
| tccaggcctc | cggcgaggcc | tcgacttctt | ccagtcgccc | agtttttgcc | ccaacccgcc | 1260 |
| tggcctggaa | gccctcagcc | caacaccag | ctgccgccac | ttccctctgc | tggtcagtag | 1320 |
| cagcttctca | cgtgtggacc | tattcaatgg | gctgttggga | ccagtacagg | tcactgcatt | 1380 |
| gtatgtgaca | cgccttgaca | acgtcacagt | ggcacacatg | ggcacaatgg | atgggcgtat | 1440 |
| cctgcaggtg | gagctggtca | ggtcactaaa | ctacttgctg | tatgtgtcca | acttctcact | 1500 |
| gggtgacagt | gggcagcccg | tgcagcggga | tgtcagtcgt | cttggggacc | acctactctt | 1560 |
| tgcctctggg | gaccaggttt | tccaggtacc | tatccgaggc | cctggctgcc | gccacttcct | 1620 |
| gacctgtggg | cgttgcctaa | gggcatggca | tttcatgggc | tgtggctggt | gtgggaacat | 1680 |
| gtgcggccag | cagaaggagt | gtcctggctc | ctggcaacag | gaccactgcc | cacctaagct | 1740 |
| tactgagttc | cacccccaca | gtggacctct | aagggcagt | acaaggctga | ccctgtgtgg | 1800 |
| ctccaacttc | taccttcacc | cttctggtct | ggtgcctgag | ggaacccatc | aggtcactgt | 1860 |
| gggccaaagt | ccctgccggc | cactgcccaa | ggacagctca | aaactcagac | cagtgccccg | 1920 |
| gaaagacttt | gtagaggagt | ttgagtgtga | actggagccc | ttgggcaccc | aggcagtggg | 1980 |
| gcctaccaac | gtcagcctca | ccgtgactaa | catgccaccg | gcaagcact | tccgggtaga | 2040 |
| cggcacctcc | gtgctgagag | gcttctcttt | catggagcca | gtgctgatag | cagtgcaacc | 2100 |
| cctctttggc | ccacgggcag | gaggcacctg | tctcactctt | gaaggccaga | gtctgtctgt | 2160 |
| aggcaccagc | cgggctgtgc | tggtcaatgg | gactgagtgt | ctgctagcac | gggtcagtga | 2220 |

```
ggggcagctt ttatgtgcca caccccctgg ggccacggtg gccagtgtcc cccttagcct    2280
gcaggtgggg ggtgcccagg tacctggttc ctggaccttc cagtacagag aagaccctgt    2340
cgtgctaagc atcagcccca actgtggcta catcaactcc cacatcacca tctgtggcca    2400
gcatctaact tcagcatggc acttagtgct gtcattccat gacgggctta gggcagtgga    2460
aagcaggtgt gagaggcagc ttccagagca gcagctgtgc cgccttcctg aatatgtggt    2520
ccgagacccc cagggatggg tggcagggaa tctgagtgcc cgaggggatg gagctgctgg    2580 cttttacactg cctggctttc gcttcctacc cccaccccat ccacccagtg ccaacctagt    2640
tccactgaag cctgaggagc atgccattaa gtttgaggtc tgcgtagatg cactccctgc    2700
cattgatggt ctggattcca ccacttgtgt ccatggagca tccttctccg atagtgaaga    2760
tgaatcctgt gtgccactgc tgcggaaaga gtccatccag ctaagggacc tggactctgc    2820
gctcttggct gaggtcaagg atgtgctgat tccccatgag cgggtggtca cccacagtga    2880
ccgagtcatt ggcaaaggcc actttggagt tgtctaccac ggagaataca tagaccaggc    2940
ccagaatcga atccaatgtg ccatcaagtc actaagtcgc atcacagaga tgcagcaggt    3000
ggaggccttc ctgcgagagg ggctgctcat gcgtggcctg aaccacccga atgtgctggc    3060
tctcattggt atcatgttgc cacctgaggg cctgccccat gtgctgctgc cctatatgtg    3120
ccacggtgac ctgctccagt tcatccgctc acctcagcgg aaccccaccg tgaaggacct    3180
catcagcttt ggcctgcagg tagcccgcgg catggagtac ctggcagagc agaagtttgt    3240
gcacagggac ctggctgcgc ggaactgcat gctggacgag tcattcacag tcaaggtggc    3300
tgactttggt ttggcccgcg acatcctgga cagggagtac tatagtgttc aacagcatcg    3360
ccacgctcgc ctacctgtga agtggatggc gctgagagc ctgcagacct atagatttac    3420
caccaagtct gatgtggtac aagtgatgc agcaatgctg ggaggcagac ccagcagtgc    3480
gacccacctt cagagtacta gtgggggagg tggagcagat agtgtctgca ctgcttgggg    3540
accattatgt gcagctgcca gcaacctaca tgaacttgag ctaaccccaa ggctgcctct    3600
gggccatgcc aggccagagc agtggccctc caccttgttc ctgcccttta actttcagag    3660
gcaataggta aatgggccca ttaggtccct cactccacag agtgagccag tgagggcagt    3720
cctgcaacat gtatttatgg agtgcctgct gtggaccctg tcttctgggc acagtggact    3780
cagcagtgac cacaccaaca ctgacccttg aaccaataaa ggaacaaatg actattaaag    3840
cacaaaaaaa aaa                                                       3853

<210> SEQ ID NO 8
<211> LENGTH: 1212
<212> TYPE: PRT
<213> ORGANISM: Homo sapiens

<400> SEQUENCE: 8

Met Glu Leu Leu Pro Pro Leu Pro Gln Ser Phe Leu Leu Leu Leu Leu
1               5                   10                  15

Leu Pro Ala Lys Pro Ala Ala Gly Glu Asp Trp Gln Cys Pro Arg Thr
            20                  25                  30

Pro Tyr Ala Ala Ser Arg Asp Phe Asp Val Lys Tyr Val Val Pro Ser
        35                  40                  45

Phe Ser Ala Gly Gly Leu Val Gln Ala Met Val Thr Tyr Glu Gly Asp
    50                  55                  60

Arg Asn Glu Ser Ala Val Phe Val Ala Ile Arg Asn Arg Leu His Val
65                  70                  75                  80
```

```
Leu Gly Pro Asp Leu Lys Ser Val Gln Ser Leu Ala Thr Gly Pro Ala
            85                  90                  95

Gly Asp Pro Gly Cys Gln Thr Cys Ala Ala Cys Gly Pro Gly Pro His
           100                 105                 110

Gly Pro Pro Gly Asp Thr Asp Thr Lys Val Leu Val Leu Asp Pro Ala
           115                 120                 125

Leu Pro Ala Leu Val Ser Cys Gly Ser Ser Leu Gln Gly Arg Cys Phe
    130                 135                 140

Leu His Asp Leu Glu Pro Gln Gly Thr Ala Val His Leu Ala Ala Pro
145                 150                 155                 160

Ala Cys Leu Phe Ser Ala His His Asn Arg Pro Asp Asp Cys Pro Asp
                165                 170                 175

Cys Val Ala Ser Pro Leu Gly Thr Arg Val Thr Val Val Glu Gln Gly
            180                 185                 190

Gln Ala Ser Tyr Phe Tyr Val Ala Ser Ser Leu Asp Ala Ala Val Ala
        195                 200                 205

Gly Ser Phe Ser Pro Arg Ser Val Ser Ile Arg Arg Leu Lys Ala Asp
    210                 215                 220

Ala Ser Gly Phe Ala Pro Gly Phe Val Ala Leu Ser Val Leu Pro Lys
225                 230                 235                 240

His Leu Val Ser Tyr Ser Ile Glu Tyr Val His Ser Phe His Thr Gly
                245                 250                 255

Ala Phe Val Tyr Phe Leu Thr Val Gln Pro Ala Ser Val Thr Asp Asp
            260                 265                 270

Pro Ser Ala Leu His Thr Arg Leu Ala Arg Leu Ser Ala Thr Glu Pro
        275                 280                 285

Glu Leu Gly Asp Tyr Arg Glu Leu Val Leu Asp Cys Arg Phe Ala Pro
    290                 295                 300

Lys Arg Arg Arg Arg Gly Ala Pro Glu Gly Gly Gln Pro Tyr Pro Val
305                 310                 315                 320

Leu Gln Val Ala His Ser Ala Pro Val Gly Ala Gln Leu Ala Thr Glu
                325                 330                 335

Leu Ser Ile Ala Glu Gly Gln Glu Val Leu Phe Gly Val Phe Val Thr
            340                 345                 350

Gly Lys Asp Gly Gly Pro Gly Val Gly Pro Asn Ser Val Val Cys Ala
        355                 360                 365

Phe Pro Ile Asp Leu Leu Asp Thr Leu Ile Asp Glu Gly Val Glu Arg
    370                 375                 380

Cys Cys Glu Ser Pro Val His Pro Gly Leu Arg Arg Gly Leu Asp Phe
385                 390                 395                 400

Phe Gln Ser Pro Ser Phe Cys Pro Asn Pro Pro Gly Leu Glu Ala Leu
                405                 410                 415

Ser Pro Asn Thr Ser Cys Arg His Phe Pro Leu Leu Val Ser Ser Ser
            420                 425                 430

Phe Ser Arg Val Asp Leu Phe Asn Gly Leu Leu Gly Pro Val Gln Val
        435                 440                 445

Thr Ala Leu Tyr Val Thr Arg Leu Asp Asn Val Thr Val Ala His Met
    450                 455                 460

Gly Thr Met Asp Gly Arg Ile Leu Gln Val Glu Leu Val Arg Ser Leu
465                 470                 475                 480

Asn Tyr Leu Leu Tyr Val Ser Asn Phe Ser Leu Gly Asp Ser Gly Gln
                485                 490                 495

Pro Val Gln Arg Asp Val Ser Arg Leu Gly Asp His Leu Leu Phe Ala
            500                 505                 510
```

-continued

Ser Gly Asp Gln Val Phe Gln Val Pro Ile Arg Gly Pro Gly Cys Arg
        515                 520                 525

His Phe Leu Thr Cys Gly Arg Cys Leu Arg Ala Trp His Phe Met Gly
        530                 535                 540

Cys Gly Trp Cys Gly Asn Met Cys Gly Gln Gln Lys Glu Cys Pro Gly
545                 550                 555                 560

Ser Trp Gln Gln Asp His Cys Pro Pro Lys Leu Thr Glu Phe His Pro
        565                 570                 575

His Ser Gly Pro Leu Arg Gly Ser Thr Arg Leu Thr Leu Cys Gly Ser
        580                 585                 590

Asn Phe Tyr Leu His Pro Ser Gly Leu Val Pro Glu Gly Thr His Gln
        595                 600                 605

Val Thr Val Gly Gln Ser Pro Cys Arg Pro Leu Pro Lys Asp Ser Ser
        610                 615                 620

Lys Leu Arg Pro Val Pro Arg Lys Asp Phe Val Glu Glu Phe Glu Cys
625                 630                 635                 640

Glu Leu Glu Pro Leu Gly Thr Gln Ala Val Gly Pro Thr Asn Val Ser
        645                 650                 655

Leu Thr Val Thr Asn Met Pro Pro Gly Lys His Phe Arg Val Asp Gly
        660                 665                 670

Thr Ser Val Leu Arg Gly Phe Ser Phe Met Glu Pro Val Leu Ile Ala
        675                 680                 685

Val Gln Pro Leu Phe Gly Pro Arg Ala Gly Gly Thr Cys Leu Thr Leu
        690                 695                 700

Glu Gly Gln Ser Leu Ser Val Gly Thr Ser Arg Ala Val Leu Val Asn
705                 710                 715                 720

Gly Thr Glu Cys Leu Leu Ala Arg Val Ser Glu Gly Gln Leu Leu Cys
        725                 730                 735

Ala Thr Pro Pro Gly Ala Thr Val Ala Ser Val Pro Leu Ser Leu Gln
        740                 745                 750

Val Gly Gly Ala Gln Val Pro Gly Ser Trp Thr Phe Gln Tyr Arg Glu
        755                 760                 765

Asp Pro Val Val Leu Ser Ile Ser Pro Asn Cys Gly Tyr Ile Asn Ser
        770                 775                 780

His Ile Thr Ile Cys Gly Gln His Leu Thr Ser Ala Trp His Leu Val
785                 790                 795                 800

Leu Ser Phe His Asp Gly Leu Arg Ala Val Glu Ser Arg Cys Glu Arg
        805                 810                 815

Gln Leu Pro Glu Gln Gln Leu Cys Arg Leu Pro Glu Tyr Val Val Arg
        820                 825                 830

Asp Pro Gln Gly Trp Val Ala Gly Asn Leu Ser Ala Arg Gly Asp Gly
        835                 840                 845

Ala Ala Gly Phe Thr Leu Pro Gly Phe Arg Phe Leu Pro Pro Pro His
        850                 855                 860

Pro Pro Ser Ala Asn Leu Val Pro Leu Lys Pro Glu Glu His Ala Ile
865                 870                 875                 880

Lys Phe Glu Val Cys Val Asp Ala Leu Pro Ala Ile Asp Gly Leu Asp
        885                 890                 895

Ser Thr Thr Cys Val His Gly Ala Ser Phe Ser Asp Ser Glu Asp Glu
        900                 905                 910

Ser Cys Val Pro Leu Leu Arg Lys Glu Ser Ile Gln Leu Arg Asp Leu
        915                 920                 925

Asp Ser Ala Leu Leu Ala Glu Val Lys Asp Val Leu Ile Pro His Glu

```
                    930             935             940
Arg Val Val Thr His Ser Asp Arg Val Ile Gly Lys Gly His Phe Gly
945                 950             955             960

Val Val Tyr His Gly Glu Tyr Ile Asp Gln Ala Gln Asn Arg Ile Gln
                965             970             975

Cys Ala Ile Lys Ser Leu Ser Arg Ile Thr Glu Met Gln Gln Val Glu
            980             985             990

Ala Phe Leu Arg Glu Gly Leu Leu Met Arg Gly Leu Asn His Pro Asn
        995             1000            1005

Val Leu Ala Leu Ile Gly Ile Met Leu Pro Pro Glu Gly Leu Pro
    1010            1015            1020

His Val Leu Leu Pro Tyr Met Cys His Gly Asp Leu Leu Gln Phe
    1025            1030            1035

Ile Arg Ser Pro Gln Arg Asn Pro Thr Val Lys Asp Leu Ile Ser
    1040            1045            1050

Phe Gly Leu Gln Val Ala Arg Gly Met Glu Tyr Leu Ala Glu Gln
    1055            1060            1065

Lys Phe Val His Arg Asp Leu Ala Ala Arg Asn Cys Met Leu Asp
    1070            1075            1080

Glu Ser Phe Thr Val Lys Val Ala Asp Phe Gly Leu Ala Arg Asp
    1085            1090            1095

Ile Leu Asp Arg Glu Tyr Tyr Ser Val Gln Gln His Arg His Ala
    1100            1105            1110

Arg Leu Pro Val Lys Trp Met Ala Leu Glu Ser Leu Gln Thr Tyr
    1115            1120            1125

Arg Phe Thr Thr Lys Ser Asp Val Val Pro Ser Asp Ala Ala Met
    1130            1135            1140

Leu Gly Gly Arg Pro Ser Ser Ala Thr His Leu Gln Ser Thr Ser
    1145            1150            1155

Gly Gly Gly Gly Ala Asp Ser Val Cys Thr Ala Trp Gly Pro Leu
    1160            1165            1170

Cys Ala Ala Ala Ser Asn Leu His Glu Leu Glu Leu Thr Pro Arg
    1175            1180            1185

Leu Pro Leu Gly His Ala Arg Pro Glu Gln Trp Pro Ser Thr Leu
    1190            1195            1200

Phe Leu Pro Phe Asn Phe Gln Arg Gln
    1205            1210

<210> SEQ ID NO 9
<211> LENGTH: 22
<212> TYPE: DNA
<213> ORGANISM: Artificial
<220> FEATURE:
<223> OTHER INFORMATION: forward primer for Ron gene variants

<400> SEQUENCE: 9
gactgagtgt ctgctagcac gg                                              22

<210> SEQ ID NO 10
<211> LENGTH: 22
<212> TYPE: DNA
<213> ORGANISM: Artificial
<220> FEATURE:
<223> OTHER INFORMATION: reverse primer for Ron gene variants

<400> SEQUENCE: 10
atggcaggga gtgcatctac gc                                              22
```

```
<210> SEQ ID NO 11
<211> LENGTH: 20
<212> TYPE: DNA
<213> ORGANISM: Artificial
<220> FEATURE:
<223> OTHER INFORMATION: forward primer for GAPDH

<400> SEQUENCE: 11
tgggtgtgaa ccatgagaag                                               20

<210> SEQ ID NO 12
<211> LENGTH: 20
<212> TYPE: DNA
<213> ORGANISM: Artificial
<220> FEATURE:
<223> OTHER INFORMATION: reverse primer for GAPDH

<400> SEQUENCE: 12
gtgtcgctgt tgaagtcaga                                               20
```